United States Patent
Garoff et al.

(10) Patent No.: US 6,770,283 B1
(45) Date of Patent: *Aug. 3, 2004

(54) DNA EXPRESSION SYSTEMS BASED ON ALPHAVIRUSES

(75) Inventors: Henrik Garoff, Hägersten (SE); Peter Liljeström, Tullinge (SE)

(73) Assignee: Bioption AB, Tullinge (SE)

(*) Notice: Subject to any disclaimer, the term of this patent is extended or adjusted under 35 U.S.C. 154(b) by 0 days.

This patent is subject to a terminal disclaimer.

(21) Appl. No.: 09/688,842

(22) Filed: Oct. 17, 2000

Related U.S. Application Data

(63) Continuation of application No. 08/466,277, filed on Jun. 6, 1995, now Pat. No. 6,190,666, which is a continuation of application No. 07/920,281, filed as application No. PCT/SE91/00855 on Dec. 12, 1991, now Pat. No. 5,739,026.

(30) Foreign Application Priority Data

Dec. 13, 1990 (SE) ............................................. 9003978

(51) Int. Cl.$^7$ ........................ C12N 15/86; A61K 48/00; A61K 39/00

(52) U.S. Cl. .................. 424/199.1; 424/93.1; 424/93.2; 424/93.6; 424/204.1; 435/320.1; 435/455; 435/456

(58) Field of Search .......................... 435/320.1, 235.1, 435/455, 456; 424/93.1, 93.2, 93.6, 188.1, 199.1, 204.1

(56) References Cited

U.S. PATENT DOCUMENTS

| | | | |
|---|---|---|---|
| 4,943,628 A | 7/1990 | Rosen et al. | |
| 5,217,879 A | 6/1993 | Huang et al. | |
| 5,792,462 A | 8/1998 | Johnston et al. | |
| 6,190,666 B1 * | 2/2001 | Garoff et al. | ............ 424/208.1 |

FOREIGN PATENT DOCUMENTS

| | | |
|---|---|---|
| EP | 0194809 | 9/1986 |
| WO | WO8912095 | 12/1989 |

OTHER PUBLICATIONS

Barry Bloom, Bumps on the Vaccine Road, vol. 265, Sep. 1994.*
V. Glaser, Biotech Firms Shift Focus Toward Therapeutic HIV Vaccine Development, Jan. 1, 1996.*
N. Regina Rabinovich et al, Vaccine Technologies: View to the Future, vol. 265, Sep. 1994.*
Phillip R. Pittman et al., "Long–term duration of detectable neutralizing antibodies after administration of live–attenuated VEE vaccine and following booster vaccination with inactivated VEE vaccine," Vaccine, vol. 14, pp. 337–343, 1996.

David J. McClain et al., "Immunologic Interference from Sequential Administration of Live Attenuated Alphavirus Vaccines," The Journal of Infectious Diseases, vol. 177, pp. 634–641, 1998.
Weiss et al. (1989) *J. Virol.*, vol. 63, pp. 5310–5318.
Hahn et al. (1988) *Proc. Natl. Acad. Sci. USA*, vol. 85, pp. 5997–6001.
Ou et al. (1983) *J. Mol. Biol.*, vol. 168, pp. 1–15.
Ou et al. (1981) *Virology*, vol. 109, pp. 281–289.
Ou et al. (1982) *J. Mol. Biol.*, vol. 156, pp. 719–730.
Strauss et al., pp. 205–234 in *Virus Structure and Assembly* S. Casjens, ed., c. 1985 by Jones and Bartlett, Boston, MA.
Jalanko et al. (1985), *Virology*, vol. 141, pp. 257–266.
Kaarlainen et al. (1981), *Virology*, vol. 113, pp. 686–697.
Kuhn et al. (1990) *J. Virol.*, vol. 64, pp. 1465–1476.
Kuhn et al. (1991) *Virology*, vol. 182, pp. 430–441.
Niesters et al. (1990) *J. Virol.*, vol. 64, pp. 4162–4168, 1639–1649.
Rabinovich, et al., *Science* (1994), vol. 265, pp. 1401–1404.
Zhou et al., (Mar. 1995), *Proc. Natl. Acad. Sci. USA*, vol. 92, pp. 3009–3013.
Zhou et al., (1994), *Vaccine*, vol. 12, No. 16, pp. 1510–1514.
Berglund et al., (1999), *Vaccine*, vol. 17, pp. 497–507.
Berglund et al., (1998), *Nature Biotechnology*, vol. 16, pp. 562–565.
Mossman et al., (Mar. 1996), *Journal of Virology*, vol. 70, No. 3, pp. 1953–1960.
Wang et al., (Oct. 16, 1998), *Science*, vol. 282, pp. 476–480.
WHO Technical Report Series, WHO Expert Committee on Rabies, 8$^{th}$ Report (excerpt), World Health Organization (Geneva, 1992).
M. Roumiantzeff et al., (1984), *Applied Virology*, pp. 252–253.
New Generation Vaccines, Second Edition, Levine et al. ed., "Vaccines Based on Molecular Biology" pp. 610–611.
Cohen, J., *Science* (1994), vol. 265, pp. 1371–1373.
Rouse et al. (1988), *Rev. Infect. Dis.*, vol. 10, No. 1, pp. 16–33.
Klavinskis et al., (1989), *J. Virol.*, vol. 63, No. 10, pp. 4311–4316.
Ellis et al., (1990) *J. Med. Virol.*, vol. 31, pp. 54–58.
Jaenicke, (1987), *Prog. Biophys. Molec. Biol.*, vol. 49, pp. 117–237.
E. G. Strauss et al., Structure and Replication of the Alphavirus Genome, pp. 35–90 in *The Togaviridae and Flaviviridae*, Schleschinger S., et al. eds., c. 1986 by Plenum Press, NY.

(List continued on next page.)

*Primary Examiner*—David Guzo
(74) *Attorney, Agent, or Firm*—Birch, Stewart, Kolasch & Birch, LLP

(57) ABSTRACT

The disclosure describes recombinant alphavirus RNA molecules and expression of heterologous proteins therefrom in animal cells. Recombinant alphaviruses of the present invention, when made to express an antigenic protein, can be administered as vaccines.

17 Claims, 33 Drawing Sheets-

OTHER PUBLICATIONS

Alphaviruses, 33(4),—"A new vector expressing heterologous genes", in *Vopr. Virusol.,* pp. 502–504, Jul.–Aug. 1988.

Levis et al., (1987), *Proc. Nat'l Academy of Science,* vol. 84, pp. 4811–4815.

Xiong, et al., (Mar. 3, 1989), *Science,* vol. 243, pp. 1188–1191.

K. Takkinen, (1986), *Nucleic Acids Research,* vol. 14, No. 14, pp. 5667–5682.

Garoff et al., in Cooper et al., (1982), eds., *Current Topic in Microbiology and Immunology,* Springer–Verlag, New York, pp. 1–50.

* cited by examiner

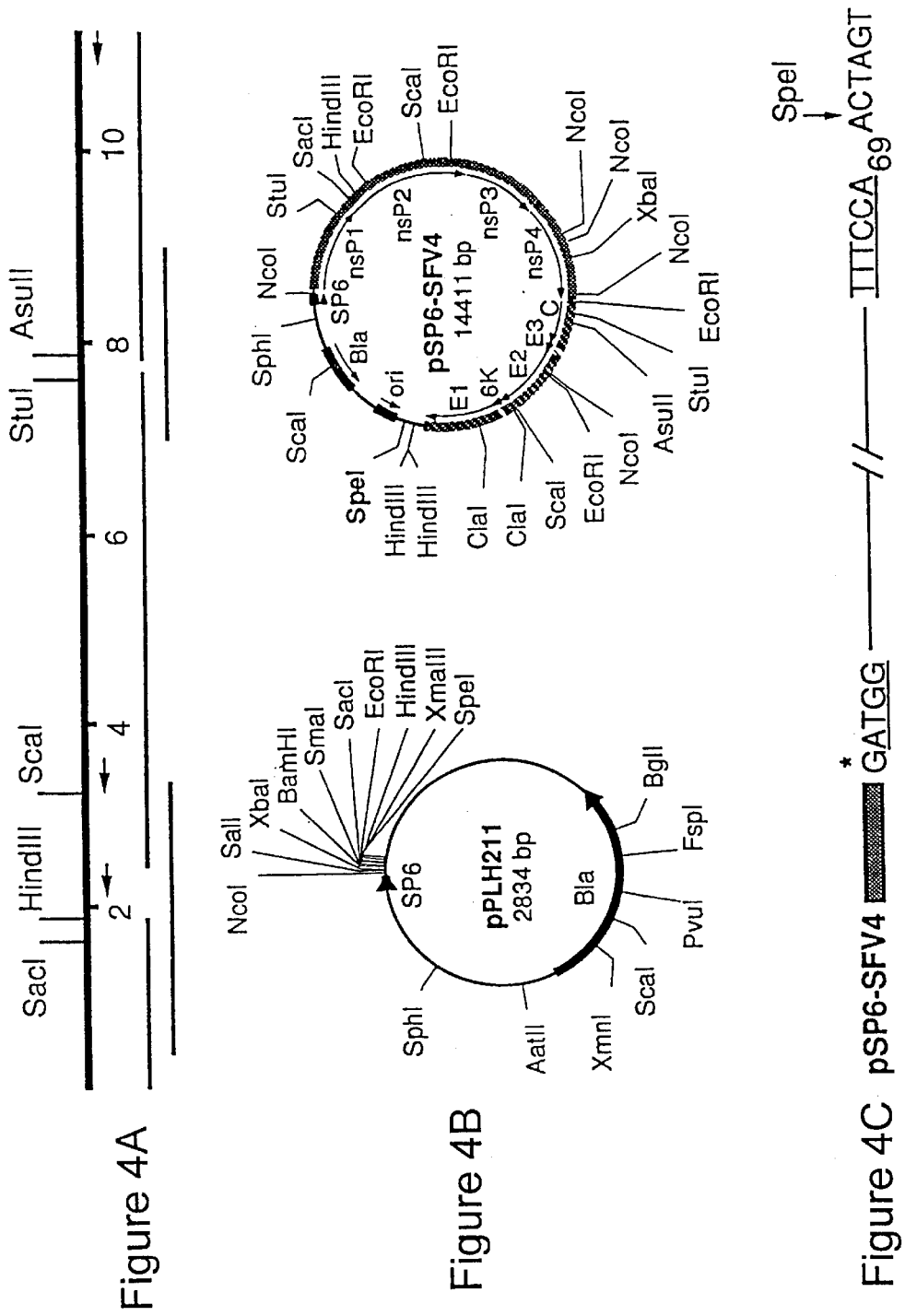

Figure 5A

```
GATGGCGGAT GTGTGACATA CACGACGCCA AAAGATTTTG TTCCAGCTCC TGCCACCTCC    60

GCTACGCGAG AGATTAACCA CCCACG ATG GCC GCC AAA GTG CAT GTT GAT ATT   113
                             Met Ala Ala Lys Val His Val Asp Ile
                                                              5

GAG GCT GAC AGC CCA TTC ATC AAG TCT TTG CAG AAG GCA TTT CCG        158
Glu Ala Asp Ser Pro Phe Ile Lys Ser Leu Gln Lys Ala Phe Pro
 10              15                  20

TCG TTC GAG GTG GAG TCA TTG CAG GTC ACA CCA AAT GAC CAT GCA        203
Ser Phe Glu Val Glu Ser Leu Gln Val Thr Pro Asn Asp His Ala
 25              30                  35

AAT GCC AGA GCA TTT TCG CAC CTG GCT ACC AAA TTG ATC GAG CAG        248
Asn Ala Arg Ala Phe Ser His Leu Ala Thr Lys Leu Ile Glu Gln
 40              45                  50

GAG ACT GAC AAA GAC ACA CTC ATC TTG GAT ATC GGC AGT GCG CCT        293
Glu Thr Asp Lys Asp Thr Leu Ile Leu Asp Ile Gly Ser Ala Pro
 55              60                  65

TCC AGG AGA ATG ATG TCT ACG CAC AAA TAC CAC TGC GTA TGC CCT        338
Ser Arg Arg Met Met Ser Thr His Lys Tyr His Cys Val Cys Pro
 70              75                  80

ATG CGC AGC GCA GAA GAC CCC GAA AGG CTC GAT AGC TAC GCA AAG        383
Met Arg Ser Ala Glu Asp Pro Glu Arg Leu Asp Ser Tyr Ala Lys
 85              90                  95

AAA CTG GCA GCG GCC TCC GGG AAG GTG CTG GAT AGA GAG ATC GCA        428
Lys Leu Ala Ala Ala Ser Gly Lys Val Leu Asp Arg Glu Ile Ala
100             105                 110

GGA AAA ATC ACC GAC CTG CAG ACC GTC ATG GCT ACG CCA GAC GCT        473
Gly Lys Ile Thr Asp Leu Gln Thr Val Met Ala Thr Pro Asp Ala
115             120                 125

GAA TCT CCT ACC TTT TGC CTG CAT ACA GAC GTC ACG TGT CGT ACG        518
Glu Ser Pro Thr Phe Cys Leu His Thr Asp Val Thr Cys Arg Thr
130             135                 140

GCA GCC GAA GTG GCC GTA TAC CAG GAC GTG TAT GCT GTA CAT GCA        563
Ala Ala Glu Val Ala Val Tyr Gln Asp Val Tyr Ala Val His Ala
145             150                 155

CCA ACA TCG CTG TAC CAT CAG GCG ATG AAA GGT GTC AGA ACG GCG        608
Pro Thr Ser Leu Tyr His Gln Ala Met Lys Gly Val Arg Thr Ala
160             165                 170

TAT TGG ATT GGG TTT GAC ACC ACC CCG TTT ATG TTT GAC GCG CTA        653
Tyr Trp Ile Gly Phe Asp Thr Thr Pro Phe Met Phe Asp Ala Leu
175             180                 185
```

Figure 5B

```
GCA GGC GCG TAT CCA ACC TAC GCC ACA AAC TGG GCC GAC GAG CAG    698
Ala Gly Ala Tyr Pro Thr Tyr Ala Thr Asn Trp Ala Asp Glu Gln
190             195             200

GTG TTA CAG GCC AGG AAC ATA GGA CTG TGT GCA GCA TCC TTG ACT    743
Val Leu Gln Ala Arg Asn Ile Gly Leu Cys Ala Ala Ser Leu Thr
205             210             215

GAG GGA AGA CTC GGC AAA CTG TCC ATT CTC CGC AAG AAG CAA TTG    788
Glu Gly Arg Leu Gly Lys Leu Ser Ile Leu Arg Lys Lys Gln Leu
220             225             230

AAA CCT TGC GAC ACA GTC ATG TTC TCG GTA GGA TCT ACA TTG TAC    833
Lys Pro Cys Asp Thr Val Met Phe Ser Val Gly Ser Thr Leu Tyr
235             240             245

ACT GAG AGC AGA AAG CTA CTG AGG AGC TGG CAC TTA CCC TCC GTA    878
Thr Glu Ser Arg Lys Leu Leu Arg Ser Trp His Leu Pro Ser Val
250             255             260

TTC CAC CTG AAA GGT AAA CAA TCC TTT ACC TGT AGG TGC GAT ACC    923
Phe His Leu Lys Gly Lys Gln Ser Phe Thr Cys Arg Cys Asp Thr
265             270             275

ATC GTA TCA TGT GAA GGG TAC GTA GTT AAG AAA ATC ACT ATG TGC    968
Ile Val Ser Cys Glu Gly Tyr Val Val Lys Lys Ile Thr Met Cys
280             285             290

CCC GGC CTG TAC GGT AAA ACG GTA GGG TAC GCC GTG ACG TAT CAC   1013
Pro Gly Leu Tyr Gly Lys Thr Val Gly Tyr Ala Val Thr Tyr His
295             300             305

GCG GAG GGA TTC CTA GTG TGC AAG ACC ACA GAC ACT GTC AAA GGA   1058
Ala Glu Gly Phe Leu Val Cys Lys Thr Thr Asp Thr Val Lys Gly
310             315             320

GAA AGA GTC TCA TTC CCT GTA TGC ACC TAC GTC CCC TCA ACC ATC   1103
Glu Arg Val Ser Phe Pro Val Cys Thr Tyr Val Pro Ser Thr Ile
325             330             335

TGT GAT CAA ATG ACT GGC ATA CTA GCG ACC GAC GTC ACA CCG GAG   1148
Cys Asp Gln Met Thr Gly Ile Leu Ala Thr Asp Val Thr Pro Glu
340             345             350

GAC GCA CAG AAG TTG TTA GTG GGA TTG AAT CAG AGG ATA GTT GTG   1193
Asp Ala Gln Lys Leu Leu Val Gly Leu Asn Gln Arg Ile Val Val
355             360             365

AAC GGA AGA ACA CAG CGA AAC ACT AAC ACG ATG AAG AAC TAT CTG   1238
Asn Gly Arg Thr Gln Arg Asn Thr Asn Thr Met Lys Asn Tyr Leu
370             375             380

CTT CCG ATT GTG GCC GTC GCA TTT AGC AAG TGG GCG AGG GAA TAC   1283
Leu Pro Ile Val Ala Val Ala Phe Ser Lys Trp Ala Arg Glu Tyr
385             390             395
```

Figure 5C

```
AAG GCA GAC CTT GAT GAT GAA AAA CCT CTG GGT GTC CGA GAG AGG   1328
Lys Ala Asp Leu Asp Asp Glu Lys Pro Leu Gly Val Arg Glu Arg
400             405                 410

TCA CTT ACT TGC TGC TGC TTG TGG GCA TTT AAA ACG AGG AAG ATG   1373
Ser Leu Thr Cys Cys Cys Leu Trp Ala Phe Lys Thr Arg Lys Met
415             420                 425

CAC ACC ATG TAC AAG AAA CCA GAC ACC CAG ACA ATA GTG AAG GTG   1418
His Thr Met Tyr Lys Lys Pro Asp Thr Gln Thr Ile Val Lys Val
430             435                 440

CCT TCA GAG TTT AAC TCG TTC GTC ATC CCG AGC CTA TGG TCT ACA   1463
Pro Ser Glu Phe Asn Ser Phe Val Ile Pro Ser Leu Trp Ser Thr
445             450                 455

GGC CTC GCA ATC CCA GTC AGA TCA CGC ATT AAG ATG CTT TTG GCC   1508
Gly Leu Ala Ile Pro Val Arg Ser Arg Ile Lys Met Leu Leu Ala
460             465                 470

AAG AAG ACC AAG CGA GAG TTA ATA CCT GTT CTC GAC GCG TCG TCA   1553
Lys Lys Thr Lys Arg Glu Leu Ile Pro Val Leu Asp Ala Ser Ser
475             480                 485

GCC AGG GAT GCT GAA CAA GAG GAG AAG GAG AGG TTG GAG GCC GAG   1598
Ala Arg Asp Ala Glu Gln Glu Glu Lys Glu Arg Leu Glu Ala Glu
490             495                 500

CTG ACT AGA GAA GCC TTA CCA CCC CTC GTC CCC ATC GCG CCG GCG   1643
Leu Thr Arg Glu Ala Leu Pro Pro Leu Val Pro Ile Ala Pro Ala
505             510                 515

GAG ACG GGA GTC GTC GAC GTC GAC GTT GAA GAA CTA GAG TAT CAC   1688
Glu Thr Gly Val Val Asp Val Asp Val Glu Glu Leu Glu Tyr His
520             525                 530

GCA GGT GCA GGG GTC GTG GAA ACA CCT CGC AGC GCG TTG AAA GTC   1733
Ala Gly Ala Gly Val Val Glu Thr Pro Arg Ser Ala Leu Lys Val
535             540                 545

ACC GCA CAG CCG AAC GAC GTA CTA CTA GGA AAT TAC GTA GTT CTG   1778
Thr Ala Gln Pro Asn Asp Val Leu Leu Gly Asn Tyr Val Val Leu
550             555                 560

TCC CCG CAG ACC GTG CTC AAG AGC TCC AAG TTG GCC CCC GTG CAC   1823
Ser Pro Gln Thr Val Leu Lys Ser Ser Lys Leu Ala Pro Val His
565             570                 575

CCT CTA GCA GAG CAG GTG AAA ATA ATA ACA CAT AAC GGG AGG GCC   1868
Pro Leu Ala Glu Gln Val Lys Ile Ile Thr His Asn Gly Arg Ala
580             585                 590

GGC GGT TAC CAG GTC GAC GGA TAT GAC GGC AGG GTC CTA CTA CCA   1913
Gly Gly Tyr Gln Val Asp Gly Tyr Asp Gly Arg Val Leu Leu Pro
595             600                 605
```

Figure 5D

```
TGT GGA TCG GCC ATT CCG GTC CCT GAG TTT CAA GCT TTG AGC GAG   1958
Cys Gly Ser Ala Ile Pro Val Pro Glu Phe Gln Ala Leu Ser Glu
610                 615                 620

AGC GCC ACT ATG GTG TAC AAC GAA AGG GAG TTC GTC AAC AGG AAA   2003
Ser Ala Thr Met Val Tyr Asn Glu Arg Glu Phe Val Asn Arg Lys
625                 630                 635

CTA TAC CAT ATT GCC GTT CAC GGA CCG TCG CTG AAC ACC GAC GAG   2048
Leu Tyr His Ile Ala Val His Gly Pro Ser Leu Asn Thr Asp Glu
640                 645                 650

GAG AAC TAC GAG AAA GTC AGA GCT GAA AGA ACT GAC GCC GAG TAC   2093
Glu Asn Tyr Glu Lys Val Arg Ala Glu Arg Thr Asp Ala Glu Tyr
655                 660                 665

GTG TTC GAC GTA GAT AAA AAA TGC TGC GTC AAG AGA GAG GAA GCG   2138
Val Phe Asp Val Asp Lys Lys Cys Cys Val Lys Arg Glu Glu Ala
670                 675                 680

TCG GGT TTG GTG TTG GTG GGA GAG CTA ACC AAC CCC CCG TTC CAT   2183
Ser Gly Leu Val Leu Val Gly Glu Leu Thr Asn Pro Pro Phe His
685                 690                 695

GAA TTC GCC TAC GAA GGG CTG AAG ATC AGG CCG TCG GCA CCA TAT   2228
Glu Phe Ala Tyr Glu Gly Leu Lys Ile Arg Pro Ser Ala Pro Tyr
700                 705                 710

AAG ACT ACA GTA GTA GGA GTC TTT GGG GTT CCG GGA TCA GGC AAG   2273
Lys Thr Thr Val Val Gly Val Phe Gly Val Pro Gly Ser Gly Lys
715                 720                 725

TCT GCT ATT ATT AAG AGC CTC GTG ACC AAA CAC GAT CTG GTC ACC   2318
Ser Ala Ile Ile Lys Ser Leu Val Thr Lys His Asp Leu Val Thr
730                 735                 740

AGC GGC AAG AAG GAG AAC TGC CAG GAA ATA GTT AAC GAC GTG AAG   2363
Ser Gly Lys Lys Glu Asn Cys Gln Glu Ile Val Asn Asp Val Lys
745                 750                 755

AAG CAC CGC GGG AAG GGG ACA AGT AGG GAA AAC AGT GAC TCC ATC   2408
Lys His Arg Gly Lys Gly Thr Ser Arg Glu Asn Ser Asp Ser Ile
760                 765                 770

CTG CTA AAC GGG TGT CGT CGT GCC GTG GAC ATC CTA TAT GTG GAC   2453
Leu Leu Asn Gly Cys Arg Arg Ala Val Asp Ile Leu Tyr Val Asp
775                 780                 785

GAG GCT TTC GCT TGC CAT TCC GGT ACT CTG CTG GCC CTA ATT GCT   2498
Glu Ala Phe Ala Cys His Ser Gly Thr Leu Leu Ala Leu Ile Ala
790                 795                 800

CTT GTT AAA CCT CGG AGC AAA GTG GTG TTA TGC GGA GAC CCC AAG   2543
Leu Val Lys Pro Arg Ser Lys Val Val Leu Cys Gly Asp Pro Lys
805                 810                 815
```

Figure 5E

```
CAA TGC GGA TTC TTC AAT ATG ATG CAG CTT AAG GTG AAC TTC AAC    2588
Gln Cys Gly Phe Phe Asn Met Met Gln Leu Lys Val Asn Phe Asn
820                 825                 830

CAC AAC ATC TGC ACT GAA GTA TGT CAT AAA AGT ATA TCC AGA CGT    2633
His Asn Ile Cys Thr Glu Val Cys His Lys Ser Ile Ser Arg Arg
835                 840                 845

TGC ACG CGT CCA GTC ACG GCC ATC GTG TCT ACG TTG CAC TAC GGA    2678
Cys Thr Arg Pro Val Thr Ala Ile Val Ser Thr Leu His Tyr Gly
850                 855                 860

GGC AAG ATG CGC ACG ACC AAC CCG TGC AAC AAA CCC ATA ATC ATA    2723
Gly Lys Met Arg Thr Thr Asn Pro Cys Asn Lys Pro Ile Ile Ile
865                 870                 875

GAC ACC ACA GGA CAG ACC AAG CCC AAG CCA GGA GAC ATC GTG TTA    2768
Asp Thr Thr Gly Gln Thr Lys Pro Lys Pro Gly Asp Ile Val Leu
880                 885                 890

ACA TGC TTC CGA GGC TGG GCA AAG CAG CTG CAG TTG GAC TAC CGT    2813
Thr Cys Phe Arg Gly Trp Ala Lys Gln Leu Gln Leu Asp Tyr Arg
895                 900                 905

GGA CAC GAA GTC ATG ACA GCA GCA GCA TCT CAG GGC CTC ACC CGC    2858
Gly His Glu Val Met Thr Ala Ala Ala Ser Gln Gly Leu Thr Arg
910                 915                 920

AAA GGG GTA TAC GCC GTA AGG CAG AAG GTG AAT GAA AAT CCC TTG    2903
Lys Gly Val Tyr Ala Val Arg Gln Lys Val Asn Glu Asn Pro Leu
925                 930                 935

TAT GCC CCT GCG TCG GAG CAC GTG AAT GTA CTG CTG ACG CGC ACT    2948
Tyr Ala Pro Ala Ser Glu His Val Asn Val Leu Leu Thr Arg Thr
940                 945                 950

GAG GAT AGG CTG GTG TGG AAA ACG CTG GCC GGC GAT CCC TGG ATT    2993
Glu Asp Arg Leu Val Trp Lys Thr Leu Ala Gly Asp Pro Trp Ile
955                 960                 965

AAG GTC CTA TCA AAC ATT CCA CAG GGT AAC TTT ACG GCC ACA TTG    3038
Lys Val Leu Ser Asn Ile Pro Gln Gly Asn Phe Thr Ala Thr Leu
970                 975                 980

GAA GAA TGG CAA GAA GAA CAC GAC AAA ATA ATG AAG GTG ATT GAA    3083
Glu Glu Trp Gln Glu Glu His Asp Lys Ile Met Lys Val Ile Glu
985                 990                 995

GGA CCG GCT GCG CCT GTG GAC GCG TTC CAG AAC AAA GCG AAC GTG    3128
Gly Pro Ala Ala Pro Val Asp Ala Phe Gln Asn Lys Ala Asn Val
1000                1005                1010

TGT TGG GCG AAA AGC CTG GTG CCT GTC CTG GAC ACT GCC GGA ATC    3173
Cys Trp Ala Lys Ser Leu Val Pro Val Leu Asp Thr Ala Gly Ile
1015                1020                1025
```

Figure 5F

```
AGA TTG ACA GCA GAG GAG TGG AGC ACC ATA ATT ACA GCA TTT AAG    3218
Arg Leu Thr Ala Glu Glu Trp Ser Thr Ile Ile Thr Ala Phe Lys
1030                1035                1040

GAG GAC AGA GCT TAC TCT CCA GTG GTG GCC TTG AAT GAA ATT TGC    3263
Glu Asp Arg Ala Tyr Ser Pro Val Val Ala Leu Asn Glu Ile Cys
1045                1050                1055

ACC AAG TAC TAT GGA GTT GAC CTG GAC AGT GGC CTG TTT TCT GCC    3308
Thr Lys Tyr Tyr Gly Val Asp Leu Asp Ser Gly Leu Phe Ser Ala
1060                1065                1070

CCG AAG GTG TCC CTG TAT TAC GAG AAC AAC CAC TGG GAT AAC AGA    3353
Pro Lys Val Ser Leu Tyr Tyr Glu Asn Asn His Trp Asp Asn Arg
1075                1080                1085

CCT GGT GGA AGG ATG TAT GGA TTC AAT GCC GCA ACA GCT GCC AGG    3398
Pro Gly Gly Arg Met Tyr Gly Phe Asn Ala Ala Thr Ala Ala Arg
1090                1095                1100

CTG GAA GCT AGA CAT ACC TTC CTG AAG GGG CAG TGG CAT ACG GGC    3443
Leu Glu Ala Arg His Thr Phe Leu Lys Gly Gln Trp His Thr Gly
1105                1110                1115

AAG CAG GCA GTT ATC GCA GAA AGA AAA ATC CAA CCG CTT TCT GTG    3488
Lys Gln Ala Val Ile-Ala Glu Arg Lys Ile Gln Pro Leu Ser Val
1120                1125                1130

CTG GAC AAT GTA ATT CCT ATC AAC CGC AGG CTG CCG CAC GCC CTG    3533
Leu Asp Asn Val Ile Pro Ile Asn Arg Arg Leu Pro His Ala Leu
1135                1140                1145

GTG GCT GAG TAC AAG ACG GTT AAA GGC AGT AGG GTT GAG TGG CTG    3578
Val Ala Glu Tyr Lys Thr Val Lys Gly Ser Arg Val Glu Trp Leu
1150                1155                1160

GTC AAT AAA GTA AGA GGG TAC CAC GTC CTG CTG GTG AGT GAG TAC    3623
Val Asn Lys Val Arg Gly Tyr His Val Leu Leu Val Ser Glu Tyr
1165                1170                1175

AAC CTG GCT TTG CCT CGA CGC AGG GTC ACT TGG TTG TCA CCG CTG    3668
Asn Leu Ala Leu Pro Arg Arg Arg Val Thr Trp Leu Ser Pro Leu
1180                1185                1190

AAT GTC ACA GGC GCC GAT AGG TGC TAC GAC CTA AGT TTA GGA CTG    3713
Asn Val Thr Gly Ala Asp Arg Cys Tyr Asp Leu Ser Leu Gly Leu
1195                1200                1205

CCG GCT GAC GCC GGC AGG TTC GAC TTG GTC TTT GTG AAC ATT CAC    3758
Pro Ala Asp Ala Gly Arg Phe Asp Leu Val Phe Val Asn Ile His
1210                1215                1220

ACG GAA TTC AGA ATC CAC CAC TAC CAG CAG TGT GTC GAC CAC GCC    3803
Thr Glu Phe Arg Ile His His Tyr Gln Gln Cys Val Asp His Ala
1225                1230                1235
```

Figure 5G

```
ATG AAG CTG CAG ATG CTT GGG GGA GAT GCG CTA CGA CTG CTA AAA    3848
Met Lys Leu Gln Met Leu Gly Gly Asp Ala Leu Arg Leu Leu Lys
1240            1245                1250

CCC GGC GGC ATC TTG ATG AGA GCT TAC GGA TAC GCC GAT AAA ATC    3893
Pro Gly Gly Ile Leu Met Arg Ala Tyr Gly Tyr Ala Asp Lys Ile
1255            1260                1265

AGC GAA GCC GTT GTT TCC TCC TTA AGC AGA AAG TTC TCG TCT GCA    3938
Ser Glu Ala Val Val Ser Ser Leu Ser Arg Lys Phe Ser Ser Ala
1270            1275                1280

AGA GTG TTG CGC CCG GAT TGT GTC ACC AGC AAT ACA GAA GTG TTC    3983
Arg Val Leu Arg Pro Asp Cys Val Thr Ser Asn Thr Glu Val Phe
1285            1290                1295

TTG CTG TTC TCC AAC TTT GAC AAC GGA AAG AGA CCC TCT ACG CTA    4028
Leu Leu Phe Ser Asn Phe Asp Asn Gly Lys Arg Pro Ser Thr Leu
1300            1305                1310

CAC CAG ATG AAT ACC AAG CTG AGT GCC GTG TAT GCC GGA GAA GCC    4073
His Gln Met Asn Thr Lys Leu Ser Ala Val Tyr Ala Gly Glu Ala
1315            1320                1325

ATG CAC ACG GCC GGG TGT GCA CCA TCC TAC AGA GTT AAG AGA GCA    4118
Met His Thr Ala Gly Cys Ala Pro Ser Tyr Arg Val Lys Arg Ala
1330            1335                1340

GAC ATA GCC ACG TGC ACA GAA GCG GCT GTG GTT AAC GCA GCT AAC    4163
Asp Ile Ala Thr Cys Thr Glu Ala Ala Val Val Asn Ala Ala Asn
1345            1350                1355

GCC CGT GGA ACT GTA GGG GAT GGC GTA TGC AGG GCC GTG GCG AAG    4208
Ala Arg Gly Thr Val Gly Asp Gly Val Cys Arg Ala Val Ala Lys
1360            1365                1370

AAA TGG CCG TCA GCC TTT AAG GGA GCA GCA ACA CCA GTG GGC ACA    4253
Lys Trp Pro Ser Ala Phe Lys Gly Ala Ala Thr Pro Val Gly Thr
1375            1380                1385

ATT AAA ACA GTC ATG TGC GGC TCG TAC CCC GTC ATC CAC GCT GTA    4298
Ile Lys Thr Val Met Cys Gly Ser Tyr Pro Val Ile His Ala Val
1390            1395                1400

GCG CCT AAT TTC TCT GCC ACG ACT GAA GCG GAA GGG GAC CGC GAA    4343
Ala Pro Asn Phe Ser Ala Thr Thr Glu Ala Glu Gly Asp Arg Glu
1405            1410                1415

TTG GCC GCT GTC TAC CGG GCA GTG GCC GCC GAA GTA AAC AGA CTG    4388
Leu Ala Ala Val Tyr Arg Ala Val Ala Ala Glu Val Asn Arg Leu
1420            1425                1430

TCA CTG AGC AGC GTA GCC ATC CCG CTG CTG TCC ACA GGA GTG TTC    4433
Ser Leu Ser Ser Val Ala Ile Pro Leu Leu Ser Thr Gly Val Phe
1435            1440                1445
```

Figure 5H

```
AGC GGC GGA AGA GAT AGG CTG CAG CAA TCC CTC AAC CAT CTA TTC    4478
Ser Gly Gly Arg Asp Arg Leu Gln Gln Ser Leu Asn His Leu Phe
1450            1455                1460

ACA GCA ATG GAC GCC ACG GAC GCT GAC GTG ACC ATC TAC TGC AGA    4523
Thr Ala Met Asp Ala Thr Asp Ala Asp Val Thr Ile Tyr Cys Arg
1465            1470                1475

GAC AAA AGT TGG GAG AAG AAA ATC CAG GAA GCC ATT GAC ATG AGG    4568
Asp Lys Ser Trp Glu Lys Lys Ile Gln Glu Ala Ile Asp Met Arg
1480            1485                1490

ACG GCT GTG GAG TTG CTC AAT GAT GAC GTG GAG CTG ACC ACA GAC    4613
Thr Ala Val Glu Leu Leu Asn Asp Asp Val Glu Leu Thr Thr Asp
1495            1500                1505

TTG GTG AGA GTG CAC CCG GAC AGC AGC CTG GTG GGT CGT AAG GGC    4658
Leu Val Arg Val His Pro Asp Ser Ser Leu Val Gly Arg Lys Gly
1510            1515                1520

TAC AGT ACC ACT GAC GGG TCG CTG TAC TCG TAC TTT GAA GGT ACG    4703
Tyr Ser Thr Thr Asp Gly Ser Leu Tyr Ser Tyr Phe Glu Gly Thr
1525            1530                1535

AAA TTC AAC CAG GCT GCT ATT GAT ATG GCA GAG ATA CTG ACG TTG    4748
Lys Phe Asn Gln Ala Ala Ile Asp Met Ala Glu Ile Leu Thr Leu
1540            1545                1550

TGG CCC AGA CTG CAA GAG GCA AAC GAA CAG ATA TGC CTA TAC GCG    4793
Trp Pro Arg Leu Gln Glu Ala Asn Glu Gln Ile Cys Leu Tyr Ala
1555            1560                1565

CTG GGC GAA ACA ATG GAC AAC ATC AGA TCC AAA TGT CCG GTG AAC    4838
Leu Gly Glu Thr Met Asp Asn Ile Arg Ser Lys Cys Pro Val Asn
1570            1757                1580

GAT TCC GAT TCA TCA ACA CCT CCC AGG ACA GTG CCC TGC CTG TGC    4883
Asp Ser Asp Ser Ser Thr Pro Pro Arg Thr Val Pro Cys Leu Cys
1585            1590                1595

CGC TAC GCA ATG ACA GCA GAA CGG ATC GCC CGC CTT AGG TCA CAC    4928
Arg Tyr Ala Met Thr Ala Glu Arg Ile Ala Arg Leu Arg Ser His
1600            1605                1610

CAA GTT AAA AGC ATG GTG GTT TGC TCA TCT TTT CCC CTC CCG AAA    4973
Gln Val Lys Ser Met Val Val Cys Ser Ser Phe Pro Leu Pro Lys
1615            1620                1625

TAC CAT GTA GAT GGG GTG CAG AAG GTA AAG TGC GAG AAG GTT CTC    5018
Tyr His Val Asp Gly Val Gln Lys Val Lys Cys Glu Lys Val Leu
1630            1635                1640

CTG TTC GAC CCG ACG GTA CCT TCA GTG GTT AGT CCG CGG AAG TAT    5063
Leu Phe Asp Pro Thr Val Pro Ser Val Val Ser Pro Arg Lys Tyr
1645            1650                1655
```

Figure 5I

```
GCC GCA TCT ACG ACG GAC CAC TCA GAT CGG TCG TTA CGA GGG TTT    5108
Ala Ala Ser Thr Thr Asp His Ser Asp Arg Ser Leu Arg Gly Phe
1660            1665                1670

GAC TTG GAC TGG ACC ACC GAC TCG TCT TCC ACT GCC AGC GAT ACC    5153
Asp Leu Asp Trp Thr Thr Asp Ser Ser Ser Thr Ala Ser Asp Thr
1675            1680                1685

ATG TCG CTA CCC AGT TTG CAG TCG TGT GAC ATC GAC TCG ATC TAC    5198
Met Ser Leu Pro Ser Leu Gln Ser Cys Asp Ile Asp Ser Ile Tyr
1690            1695                1700

GAG CCA ATG GCT CCC ATA GTA GTG ACG GCT GAC GTA CAC CCT GAA    5243
Glu Pro Met Ala Pro Ile Val Val Thr Ala Asp Val His Pro Glu
1705            1710                1715

CCC GCA GGC ATC GCG GAC CTG GCG GCA GAT GTG CAC CCT GAA CCC    5288
Pro Ala Gly Ile Ala Asp Leu Ala Ala Asp Val His Pro Glu Pro
1720            1725                1730

GCA GAC CAT GTG GAC CTC GAG AAC CCG ATT CCT CCA CCG CGC CCG    5333
Ala Asp His Val Asp Leu Glu Asn Pro Ile Pro Pro Pro Arg Pro
1735            1740                1745

AAG AGA GCT GCA TAC CTT GCC TCC CGC GCG GCG GAG CGA CCG GTG    5378
Lys Arg Ala Ala Tyr Leu Ala Ser Arg Ala Ala Glu Arg Pro Val
1750            1755                1760

CCG GCG CCG AGA AAG CCG ACG CCT GCC CCA AGG ACT GCG TTT AGG    5423
Pro Ala Pro Arg Lys Pro Thr Pro Ala Pro Arg Thr Ala Phe Arg
1765            1770                1775

AAC AAG CTG CCT TTG ACG TTC G.. .AC TTT GAC GAG CAC GAG GTC    5468
Asn Lys Leu Pro Leu Thr Phe Gly Asp Phe Asp Glu His Glu Val
1780            1785                1790

GAT GCG TTG GCC TCC GGG ATT ACT TTC GGA GAC TTC GAC GAC GTC    5513
Asp Ala Leu Ala Ser Gly Ile Thr Phe Gly Asp Phe Asp Asp Val
1795            1800                1805

CTG CGA CTA GGC CGC GCG GGT GCA TAT ATT TTC TCC TCG GAC ACT    5558
Leu Arg Leu Gly Arg Ala Gly Ala Tyr Ile Phe Ser Ser Asp Thr
1810            1815                1820

GGC AGC GGA CAT TTA CAA CAA AAA TCC GTT AGG CAG CAC AAT CTC    5603
Gly Ser Gly His Leu Gln Gln Lys Ser Val Arg Gln His Asn Leu
1825            1830                1835

CAG TGC GCA CAA CTG GAT GCG GTC CAG GAG GAG AAA ATG TAC CCG    5648
Gln Cys Ala Gln Leu Asp Ala Val Gln Glu Glu Lys Met Tyr Pro
1840            1845                1850

CCA AAA TTG GAT ACT GAG AGG GAG AAG CTG TTG CTG CTG AAA ATG    5693
Pro Lys Leu Asp Thr Glu Arg Glu Lys Leu Leu Leu Leu Lys Met
1855            1860                1865
```

Figure 5J

```
CAG ATG CAC CCA TCG GAG GCT AAT AAG AGT CGA TAC CAG TCT CGC    5738
Gln Met His Pro Ser Glu Ala Asn Lys Ser Arg Tyr Gln Ser Arg
1870            1875                1880

AAA GTG GAG AAC ATG AAA GCC ACG GTG GTG GAC AGG CTC ACA TCG    5783
Lys Val Glu Asn Met Lys Ala Thr Val Val Asp Arg Leu Thr Ser
1885            1890                1895

GGG GCC AGA TTG TAC ACG GGA GCG GAC GTA GGC CGC ATA CCA ACA    5828
Gly Ala Arg Leu Tyr Thr Gly Ala Asp Val Gly Arg Ile Pro Thr
1900            1905                1910

TAC GCG GTT CGG TAC CCC CGC CCC GTG TAC TCC CCT ACC GTG ATC    5873
Tyr Ala Val Arg Tyr Pro Arg Pro Val Tyr Ser Pro Thr Val Ile
1915            1920                1925

GAA AGA TTC TCA AGC CCC GAT GTA GCA ATC GCA GCG TGC AAC GAA    5918
Glu Arg Phe Ser Ser Pro Asp Val Ala Ile Ala Ala Cys Asn Glu
1930            1935                1940

TAC CTA TCC AGA AAT TAC CCA ACA GTG GCG TCG TAC CAG ATA ACA    5963
Tyr Leu Ser Arg Asn Tyr Pro Thr Val Ala Ser Tyr Gln Ile Thr
1945            1950                1955

GAT GAA TAC GAC GCA TAC TTG GAC ATG GTT GAC GGG TCG GAT AGT    6008
Asp Glu Tyr Asp Ala Tyr Leu Asp Met Val Asp Gly Ser Asp Ser
1960            1965                1970

TGC TTG GAC AGA GCG ACA TTC TGC CCG GCG AAG CTC CGG TGC TAC    6053
Cys Leu Asp Arg Ala Thr Phe Cys Pro Ala Lys Leu Arg Cys Tyr
1975            1980                1985

CCG AAA CAT CAT GCG TAC CAC CAG CCG ACT GTA CGC AGT GCC GTC    6098
Pro Lys His His Ala Tyr His Gln Pro Thr Val Arg Ser Ala Val
1990            1995                2000

CCG TCA CCC TTT CAG AAC ACA CTA CAG AAC GTG CTA GCG GCC GCC    6143
Pro Ser Pro Phe Gln Asn Thr Leu Gln Asn Val Leu Ala Ala Ala
2005            2010                2015

ACC AAG AGA AAC TGC AAC GTC ACG CAA ATG CGA GAA CTA CCC ACC    6188
Thr Lys Arg Asn Cys Asn Val Thr Gln Met Arg Glu Leu Pro Thr
2020            2025                2030

ATG GAC TCG GCA GTG TTC AAC GTG GAG TGC TTC AAG CGC TAT GCC    6233
Met Asp Ser Ala Val Phe Asn Val Glu Cys Phe Lys Arg Tyr Ala
2035            2040                2045

TGC TCC GGA GAA TAT TGG GAA GAA TAT GCT AAA CAA CCT ATC CGG    6278
Cys Ser Gly Glu Tyr Trp Glu Glu Tyr Ala Lys Gln Pro Ile Arg
2050            2055                2060

ATA ACC ACT GAG AAC ATC ACT ACC TAT GTG ACC AAA TTG AAA GGC    6323
Ile Thr Thr Glu Asn Ile Thr Thr Tyr Val Thr Lys Leu Lys Gly
2065            2070                2075
```

Figure 5K

```
CCG AAA GCT GCT GCC TTG TTC GCT AAG ACC CAC AAC TTG GTT CCG   6368
Pro Lys Ala Ala Ala Leu Phe Ala Lys Thr His Asn Leu Val Pro
2080            2085                2090

CTG CAG GAG GTT CCC ATG GAC AGA TTC ACG GTC GAC ATG AAA CGA   6413
Leu Gln Glu Val Pro Met Asp Arg Phe Thr Val Asp Met Lys Arg
2095            2100                2105

GAT GTC AAA GTC ACT CCA GGG ACG AAA CAC ACA GAG GAA AGA CCC   6458
Asp Val Lys Val Thr Pro Gly Thr Lys His Thr Glu Glu Arg Pro
2110            2115                2120

AAA GTC CAG GTA ATT CAA GCA GCG GAG CCA TTG GCG ACC GCT TAC   6503
Lys Val Gln Val Ile Gln Ala Ala Glu Pro Leu Ala Thr Ala Tyr
2125            2130                2135

CTG TGC GGC ATC CAC AGG GAA TTA GTA AGG AGA CTA AAT GCT GTG   6548
Leu Cys Gly Ile His Arg Glu Leu Val Arg Arg Leu Asn Ala Val
2140            2145                2150

TTA CGC CCT AAC GTG CAC ACA TTG TTT GAT ATG TCG GCC GAA GAC   6593
Leu Arg Pro Asn Val His Thr Leu Phe Asp Met Ser Ala Glu Asp
2155            2160                2165

TTT GAC GCG ATC ATC GCC TCT CAC TTC CAC CCA GGA GAC CCG GTT   6638
Phe Asp Ala Ile Ile Ala Ser His Phe His Pro Gly Asp Pro Val
2170            2175                2180

CTA GAG ACG GAC ATT GCA TCA TTC GAC AAA AGC CAG GAC GAC TCC   6683
Leu Glu Thr Asp Ile Ala Ser Phe Asp Lys Ser Gln Asp Asp Ser
2185            2190                2195

TTG GCT CTT ACA GGT TTA ATG ATC CTC GAA GAT CTA GGG GTG GAT   6728
Leu Ala Leu Thr Gly Leu Met Ile Leu Glu Asp Leu Gly Val Asp
2200            2205                2210

CAG TAC CTG CTG GAC TTG ATC GAG GCA GCC TTT GGG GAA ATA TCC   6773
Gln Tyr Leu Leu Asp Leu Ile Glu Ala Ala Phe Gly Glu Ile Ser
2215            2220                2225

AGC TGT CAC CTA CCA ACT GGC ACG CGC TTC AAG TTC GGA GCT ATG   6818
Ser Cys His Leu Pro Thr Gly Thr Arg Phe Lys Phe Gly Ala Met
2230            2235                2240

ATG AAA TCG GGC ATG TTT CTG ACT TTG TTT ATT AAC ACT GTT TTG   6863
Met Lys Ser Gly Met Phe Leu Thr Leu Phe Ile Asn Thr Val Leu
2245            2250                2255

AAC ATC ACC ATA GCA AGC AGG GTA CTG GAG CAG AGA CTC ACT GAC   6908
Asn Ile Thr Ile Ala Ser Arg Val Leu Glu Gln Arg Leu Thr Asp
2260            2265                2270

TCC GCC TGT GCG GCC TTC ATC GGC GAC GAC AAC ATC GTT CAC GGA   6953
Ser Ala Cys Ala Ala Phe Ile Gly Asp Asp Asn Ile Val His Gly
2275            2280                2285
```

Figure 5L

```
GTG ATC TCC GAC AAG CTG ATG GCG GAG AGG TGC GCG TCG TGG GTC   6998
Val Ile Ser Asp Lys Leu Met Ala Glu Arg Cys Ala Ser Trp Val
2290            2295            2300

AAC ATG GAG GTG AAG ATC ATT GAC GCT GTC ATG GGC GAA AAA CCC   7043
Asn Met Glu Val Lys Ile Ile Asp Ala Val Met Gly Glu Lys Pro
2305            2310            2315

CCA TAT TTT TGT GGG GGA TTC ATA GTT TTT GAC AGC GTC ACA CAG   7088
Pro Tyr Phe Cys Gly Gly Phe Ile Val Phe Asp Ser Val Thr Gln
2320            2325            2330

ACC GCC TGC CGT GTT TCA GAC CCA CTT AAG CGC CTG TTC AAG TTG   7133
Thr Ala Cys Arg Val Ser Asp Pro Leu Lys Arg Leu Phe Lys Leu
2335            2340            2345

GGT AAG CCG CTA ACA GCT GAA GAC AAG CAG GAC GAA GAC AGG CGA   7178
Gly Lys Pro Leu Thr Ala Glu Asp Lys Gln Asp Glu Asp Arg Arg
2350            2355            2360

CGA GCA CTG AGT GAC GAG GTT AGC AAG TGG TTC CGG ACA GGC TTG   7223
Arg Ala Leu Ser Asp Glu Val Ser Lys Trp Phe Arg Thr Gly Leu
2365            2370            2375

GGG GCC GAA CTG GAG GTG GCA CTA ACA TCT AGG TAT GAG GTA GAG   7268
Gly Ala Glu Leu Glu Val Ala Leu Thr Ser Arg Tyr Glu Val Glu
2380            2385            2390

GGC TGC AAA AGT ATC CTC ATA GCC ATG ACC ACC TTG GCG AGG GAC   7313
Gly Cys Lys Ser Ile Leu Ile Ala Met Thr Thr Leu Ala Arg Asp
2395            2400            2405

ATT AAG GCG TTT AAG AAA TTG AGA GGA CCT GTT ATA CAC CTC TAC   7358
Ile Lys Ala Phe Lys Lys Leu Arg Gly Pro Val Ile His Leu Tyr
2410            2415            2420

GGC GGT CCT AGA TTG GTG CGT TAA TACACAGAAT TCTGATTATA GCGCACTATT   7412
Gly Gly Pro Arg Leu Val Arg
2425            2430

ATAGCACC ATG AAT TAC ATC CCT ACG CAA ACG TTT TAC GGC CGC CGG   7459
         Met Asn Tyr Ile Pro Thr Gln Thr Phe Tyr Gly Arg Arg
                        5                      10

TGG CGC CCG CGC CCG GCG GCC CGT CCT TGG CCG TTG CAG GCC ACT   7504
Trp Arg Pro Arg Pro Ala Ala Arg Pro Trp Pro Leu Gln Ala Thr
         15              20              25

CCG GTG GCT CCC GTC GTC CCC GAC TTC CAG GCC CAG CAG ATG CAG   7549
Pro Val Ala Pro Val Val Pro Asp Phe Gln Ala Gln Gln Met Gln
         30              35              40

CAA CTC ATC AGC GCC GTA AAT GCG CTG ACA ATG AGA CAG AAC GCA   7594
Gln Leu Ile Ser Ala Val Asn Ala Leu Thr Met Arg Gln Asn Ala
         45              50              55
```

Figure 5M

```
ATT GCT CCT GCT AGG CCT CCC AAA CCA AAG AAG AAG AAG ACA ACC    7639
Ile Ala Pro Ala Arg Pro Pro Lys Pro Lys Lys Lys Lys Thr Thr
        60                  65                  70

AAA CCA AAG CCG AAA ACG CAG CCC AAG AAG ATC AAC GGA AAA ACG    7684
Lys Pro Lys Pro Lys Thr Gln Pro Lys Lys Ile Asn Gly Lys Thr
        75                  80                  85

CAG CAG CAA AAG AAG AAA GAC AAG CAA GCC GAC AAG AAG AAG AAG    7729
Gln Gln Gln Lys Lys Lys Asp Lys Gln Ala Asp Lys Lys Lys Lys
        90                  95                 100

AAA CCC GGA AAA AGA GAA AGA ATG TGC ATG AAG ATT GAA AAT GAC    7774
Lys Pro Gly Lys Arg Glu Arg Met Cys Met Lys Ile Glu Asn Asp
       105                 110                 115

TGT ATC TTC GAA GTC AAA CAC GAA GGA AAG GTC ACT GGG TAC GCC    7819
Cys Ile Phe Glu Val Lys His Glu Gly Lys Val Thr Gly Tyr Ala
       120                 125                 130

TGC CTG GTG GGC GAC AAA GTC ATG AAA CCT GCC CAC GTG AAA GGA    7864
Cys Leu Val Gly Asp Lys Val Met Lys Pro Ala His Val Lys Gly
       135                 140                 145

GTC ATC GAC AAC GCG GAC CTG GCA AAG CTA GCT TTC AAG AAA TCG    7909
Val Ile Asp Asn Ala Asp Leu Ala Lys Leu Ala Phe Lys Lys Ser
       150                 155                 160

AGC AAG TAT GAC CTT GAG TGT GCC CAG ATA CCA GTT CAC ATG AGG    7954
Ser Lys Tyr Asp Leu Glu Cys Ala Gln Ile Pro Val His Met Arg
       165                 170                 175

TCG GAT GCC TCA AAG TAC ACG CAT GAG AAG CCC GAG GGA CAC TAT    7999
Ser Asp Ala Ser Lys Tyr Thr His Glu Lys Pro Glu Gly His Tyr
       180                 185                 190

AAC TGG CAC CAC GGG GCT GTT CAG TAC AGC GGA GGT AGG TTC ACT    8044
Asn Trp His His Gly Ala Val Gln Tyr Ser Gly Gly Arg Phe Thr
       195                 200                 205

ATA CCG ACA GGA GCG GGC AAA CCG GGA GAC AGT GGC CGG CCC ATC    8089
Ile Pro Thr Gly Ala Gly Lys Pro Gly Asp Ser Gly Arg Pro Ile
       210                 215                 220

TTT GAC AAC AAG GGG AGG GTA GTC GCT ATC GTC CTG GGC GGG GCC    8134
Phe Asp Asn Lys Gly Arg Val Val Ala Ile Val Leu Gly Gly Ala
       225                 230                 235

AAC GAG GGC TCA CGC ACA GCA CTG TCG GTG GTC ACC TGG AAC AAA    8179
Asn Glu Gly Ser Arg Thr Ala Leu Ser Val Val Thr Trp Asn Lys
       240                 245                 250

GAT ATG GTG ACT AGA GTG ACC CCC GAG GGG TCC GAA GAG TGG TCC    8224
Asp Met Val Thr Arg Val Thr Pro Glu Gly Ser Glu Glu Trp Ser
       255                 260                 265
```

Figure 5N

```
GCC CCG CTG ATT ACT GCC ATG TGT GTC CTT GCC AAT GCT ACC TTC   8269
Ala Pro Leu Ile Thr Ala Met Cys Val Leu Ala Asn Ala Thr Phe
    270             275                 280

CCG TGC TTC CAG CCC CCG TGT GTA CCT TGC TGC TAT GAA AAC AAC   8314
Pro Cys Phe Gln Pro Pro Cys Val Pro Cys Cys Tyr Glu Asn Asn
    285             290                 295

GCA GAG GCC ACA CTA CGG ATG CTC GAG GAT AAC GTG GAT AGG CCA   8359
Ala Glu Ala Thr Leu Arg Met Leu Glu Asp Asn Val Asp Arg Pro
    300             305                 310

GGG TAC TAC GAC CTC CTT CAG GCA GCC TTG ACG TGC CGA AAC GGA   8404
Gly Tyr Tyr Asp Leu Leu Gln Ala Ala Leu Thr Cys Arg Asn Gly
    315             320                 325

ACA AGA CAC CGG CGC AGC GTG TCG CAA CAC TTC AAC GTG TAT AAG   8449
Thr Arg His Arg Arg Ser Val Ser Gln His Phe Asn Val Tyr Lys
    330             335                 340

GCT ACA CGC CCT TAC ATC GCG TAC TGC GCC GAC TGC GGA GCA GGG   8494
Ala Thr Arg Pro Tyr Ile Ala Tyr Cys Ala Asp Cys Gly Ala Gly
    345             350                 355

CAC TCG TGT CAT AGC CCC GTA GCA ATT GAA GCG GTC AGG TCC GAA   8539
His Ser Cys His Ser Pro Val Ala Ile Glu Ala Val Arg Ser Glu
    360             365                 370

GCT ACC GAC GGG ATG CTG AAG ATT CAG TTC TCG GCA CAA ATT GGC   8584
Ala Thr Asp Gly Met Leu Lys Ile Gln Phe Ser Ala Gln Ile Gly
    375             380                 385

ATA GAT AAG AGT GAC AAT CAT GAC TAC ACG AAG ATA AGG TAC GCA   8629
Ile Asp Lys Ser Asp Asn His Asp Tyr Thr Lys Ile Arg Tyr Ala
    390             395                 400

GAC GGG CAC GCC ATT GAG AAT GCC GTC CGG TCA TCT TTG AAG GTA   8674
Asp Gly His Ala Ile Glu Asn Ala Val Arg Ser Ser Leu Lys Val
    405             410                 415

GCC ACC TCC GGA GAC TGT TTC GTC CAT GGC ACA ATG GGA CAT TTC   8719
Ala Thr Ser Gly Asp Cys Phe Val His Gly Thr Met Gly His Phe
    420             425                 430

ATA CTG GCA AAG TGC CCA CCG GGT GAA TTC CTG CAG GTC TCG ATC   8764
Ile Leu Ala Lys Cys Pro Pro Gly Glu Phe Leu Gln Val Ser Ile
    435             440                 445

CAG GAC ACC AGA AAC GCG GTC CGT GCC TGC AGA ATA CAA TAT CAT   8809
Gln Asp Thr Arg Asn Ala Val Arg Ala Cys Arg Ile Gln Tyr His
    450             455                 460

CAT GAC CCT CAA CCG GTG GGT AGA GAA AAA TTT ACA ATT AGA CCA   8854
His Asp Pro Gln Pro Val Gly Arg Glu Lys Phe Thr Ile Arg Pro
    465             470                 475
```

Figure 5O

```
CAC TAT GGA AAA GAG ATC CCT TGC ACC ACT TAT CAA CAG ACC ACA   8899
His Tyr Gly Lys Glu Ile Pro Cys Thr Thr Tyr Gln Gln Thr Thr
    480             485                 490

GCG AAG ACC GTG GAG GAA ATC GAC ATG CAT ATG CCG CCA GAT ACG   8944
Ala Lys Thr Val Glu Glu Ile Asp Met His Met Pro Pro Asp Thr
    495             500                 505

CCG GAC AGG ACG TTG CTA TCA CAG CAA TCT GGC AAT GTA AAG ATC   8989
Pro Asp Arg Thr Leu Leu Ser Gln Gln Ser Gly Asn Val Lys Ile
    510             515                 520

ACA GTC GGA GGA AAG AAG GTG AAA TAC AAC TGC ACC TGT GGA ACC   9034
Thr Val Gly Gly Lys Lys Val Lys Tyr Asn Cys Thr Cys Gly Thr
    525             530                 535

GGA AAC GTT GGC ACT ACT AAT TCG GAC ATG ACG ATC AAC ACG TGT   9079
Gly Asn Val Gly Thr Thr Asn Ser Asp Met Thr Ile Asn Thr Cys
    540             545                 550

CTA ATA GAG CAG TGC CAC GTC TCA GTG ACG GAC CAT AAG AAA TGG   9124
Leu Ile Glu Gln Cys His Val Ser Val Thr Asp His Lys Lys Trp
    555             560                 565

CAG TTC AAC TCA CCT TTC GTC CCG AGA GCC GAC GAA CCG GCT AGA   9169
Gln Phe Asn Ser Pro Phe Val Pro Arg Ala Asp Glu Pro Ala Arg
    570             575                 580

AAA GGC AAA GTC CAT ATC CCA TTC CCG TTG GAC AAC ATC ACA TGC   9214
Lys Gly Lys Val His Ile Pro Phe Pro Leu Asp Asn Ile Thr Cys
    585             590                 595

AGA GTT CCA ATG GCG CGC GAA CCA ACC GTC ATC CAC GGC AAA AGA   9259
Arg Val Pro Met Ala Arg Glu Pro Thr Val Ile His Gly Lys Arg
    600             605                 610

GAA GTG ACA CTG CAC CTT CAC CCA GAT CAT CCC ACG CTC TTT TCC   9304
Glu Val Thr Leu His Leu His Pro Asp His Pro Thr Leu Phe Ser
    615             620                 625

TAC CGC ACA CTG GGT GAG GAC CCG CAG TAT CAC GAG GAA TGG GTG   9349
Tyr Arg Thr Leu Gly Glu Asp Pro Gln Tyr His Glu Glu Trp Val
    630             635                 640

ACA GCG GCG GTG GAA CGG ACC ATA CCC GTA CCA GTG GAC GGG ATG   9394
Thr Ala Ala Val Glu Arg Thr Ile Pro Val Pro Val Asp Gly Met
    645             650                 655

GAG TAC CAC TGG GGA AAC AAC GAC CCA GTG AGG CTT TGG TCT CAA   9439
Glu Tyr His Trp Gly Asn Asn Asp Pro Val Arg Leu Trp Ser Gln
    660             665                 670

CTC ACC ACT GAA GGG AAA CCG CAC GGC TGG CCG CAT CAG ATC GTA   9484
Leu Thr Thr Glu Gly Lys Pro His Gly Trp Pro His Gln Ile Val
    675             680                 685
```

Figure 5P

| | | | | | | | | | | | | | |
|---|---|---|---|---|---|---|---|---|---|---|---|---|---|
| CAG | TAC | TAC | TAT | GGG | CTT | TAC | CCG | GCC | GCT | ACA | GTA | TCC | GCG | GTC | 9529 |
| Gln | Tyr | Tyr | Tyr | Gly | Leu | Tyr | Pro | Ala | Ala | Thr | Val | Ser | Ala | Val | |
| | 690 | | | | 695 | | | | | 700 | | | | | |

```
CAG TAC TAC TAT GGG CTT TAC CCG GCC GCT ACA GTA TCC GCG GTC   9529
Gln Tyr Tyr Tyr Gly Leu Tyr Pro Ala Ala Thr Val Ser Ala Val
    690             695                 700

GTC GGG ATG AGC TTA CTG GCG TTG ATA TCG ATC TTC GCG TCG TGC   9574
Val Gly Met Ser Leu Leu Ala Leu Ile Ser Ile Phe Ala Ser Cys
    705             710                 715

TAC ATG CTG GTT GCG GCC CGC AGT AAG TGC TTG ACC CCT TAT GCT   9619
Tyr Met Leu Val Ala Ala Arg Ser Lys Cys Leu Thr Pro Tyr Ala
    720             725                 730

TTA ACA CCA GGA GCT GCA GTT CCG TGG ACG CTG GGG ATA CTC TGC   9664
Leu Thr Pro Gly Ala Ala Val Pro Trp Thr Leu Gly Ile Leu Cys
    735             740                 745

TGC GCC CCG CGG GCG CAC GCA GCT AGT GTG GCA GAG ACT ATG GCC   9709
Cys Ala Pro Arg Ala His Ala Ala Ser Val Ala Glu Thr Met Ala
    750             755                 760

TAC TTG TGG GAC CAA AAC CAA GCG TTG TTC TGG TTG GAG TTT GCG   9754
Tyr Leu Trp Asp Gln Asn Gln Ala Leu Phe Trp Leu Glu Phe Ala
    765             770                 775

GCC CCT GTT GCC TGC ATC CTC ATC ATC ACG TAT TGC CTC AGA AAC   9799
Ala Pro Val Ala Cys Ile Leu Ile Ile Thr Tyr Cys Leu Arg Asn
    780             785                 790

GTG CTG TGT TGC TGT AAG AGC CTT TCT TTT TTA GTG CTA CTG AGC   9844
Val Leu Cys Cys Cys Lys Ser Leu Ser Phe Leu Val Leu Leu Ser
    795             800                 805

CTC GGG GCA ACC GCC AGA GCT TAC GAA CAT TCG ACA GTA ATG CCG   9889
Leu Gly Ala Thr Ala Arg Ala Tyr Glu His Ser Thr Val Met Pro
    810             815                 820

AAC GTG GTG GGG TTC CCG TAT AAG GCT CAC ATT GAA AGG CCA GGA   9934
Asn Val Val Gly Phe Pro Tyr Lys Ala His Ile Glu Arg Pro Gly
    825             830                 835

TAT AGC CCC CTC ACT TTG CAG ATG CAG GTT GTT GAA ACC AGC CTC   9979
Tyr Ser Pro Leu Thr Leu Gln Met Gln Val Val Glu Thr Ser Leu
    840             845                 850

GAA CCA ACC CTT AAT TTG GAA TAC ATA ACC TGT GAG TAC AAG ACG   10024
Glu Pro Thr Leu Asn Leu Glu Tyr Ile Thr Cys Glu Tyr Lys Thr
    855             860                 865

GTC GTC CCG TCG CCG TAC GTG AAG TGC TGC GGC GCC TCA GAG TGC   10069
Val Val Pro Ser Pro Tyr Val Lys Cys Cys Gly Ala Ser Glu Cys
    870             875                 880

TCC ACT AAA GAG AAG CCT GAC TAC CAA TGC AAG GTT TAC ACA GGC   10114
Ser Thr Lys Glu Lys Pro Asp Tyr Gln Cys Lys Val Tyr Thr Gly
    885             890                 895
```

Figure 5Q

```
GTG TAC CCG TTC ATG TGG GGA GGG GCA TAT TGC TTC TGC GAC TCA    10159
Val Tyr Pro Phe Met Trp Gly Gly Ala Tyr Cys Phe Cys Asp Ser
    900             905             910

GAA AAC ACG CAA CTC AGC GAG GCG TAC GTC GAT CGA TCG GAC GTA    10204
Glu Asn Thr Gln Leu Ser Glu Ala Tyr Val Asp Arg Ser Asp Val
    915             920             925

TGC AGG CAT GAT CAC GCA TCT GCT TAC AAA GCC CAT ACA GCA TCG    10249
Cys Arg His Asp His Ala Ser Ala Tyr Lys Ala His Thr Ala Ser
    930             935             940

CTG AAG GCC AAA GTG AGG GTT ATG TAC GGC AAC GTA AAC CAG ACT    10294
Leu Lys Ala Lys Val Arg Val Met Tyr Gly Asn Val Asn Gln Thr
    945             950             955

GTG GAT GTT TAC GTG AAC GGA GAC CAT GCC GTC ACG ATA GGG GGT    10339
Val Asp Val Tyr Val Asn Gly Asp His Ala Val Thr Ile Gly Gly
    960             965             970

ACT CAG TTC ATA TTC GGG CCG CTG TCA TCG GCC TGG ACC CCG TTC    10384
Thr Gln Phe Ile Phe Gly Pro Leu Ser Ser Ala Trp Thr Pro Phe
    975             980             985

GAC AAC AAG ATA GTC GTG TAC AAA GAC GAA GTG TTC AAT CAG GAC    10429
Asp Asn Lys Ile Val Val Tyr Lys Asp Glu Val Phe Asn Gln Asp
    990             995             1000

TTC CCG CCG TAC GGA TCT GGG CAA CCA GGG CGC TTC GGC GAC ATC    10474
Phe Pro Pro Tyr Gly Ser Gly Gln Pro Gly Arg Phe Gly Asp Ile
    1005            1010            1015

CAA AGC AGA ACA GTG GAG AGT AAC GAC CTG TAC GCG AAC ACG GCA    10519
Gln Ser Arg Thr Val Glu Ser Asn Asp Leu Tyr Ala Asn Thr Ala
    1020            1025            1030

CTG AAG CTG GCA CGC CCT TCA CCC GGC ATG GTC CAT GTA CCG TAC    10564
Leu Lys Leu Ala Arg Pro Ser Pro Gly Met Val His Val Pro Tyr
    1035            1040            1045

ACA CAG ACA CCT TCA GGG TTC AAA TAT TGG CTA AAG GAA AAA GGG    10609
Thr Gln Thr Pro Ser Gly Phe Lys Tyr Trp Leu Lys Glu Lys Gly
    1050            1055            1060

ACA GCC CTA AAT ACG AAG GCT CCT TTT GGC TGC CAA ATC AAA ACG    10654
Thr Ala Leu Asn Thr Lys Ala Pro Phe Gly Cys Gln Ile Lys Thr
    1065            1070            1075

AAC CCT GTC AGG GCC ATG AAC TGC GCC GTG GGA AAC ATC CCT GTC    10699
Asn Pro Val Arg Ala Met Asn Cys Ala Val Gly Asn Ile Pro Val
    1080            1085            1090

TCC ATG AAT TTG CCT GAC AGC GCC TTT ACC CGC ATT GTC GAG GCG    10744
Ser Met Asn Leu Pro Asp Ser Ala Phe Thr Arg Ile Val Glu Ala
    1095            1100            1105
```

Figure 5R

```
CCG ACC ATC ATT GAC CTG ACT TGC ACA GTG GCT ACC TGT ACG CAC    10789
Pro Thr Ile Ile Asp Leu Thr Cys Thr Val Ala Thr Cys Thr His
   1110            1115                1120

TCC TCG GAT TTC GGC GGC GTC TTG ACA CTG ACG TAC AAG ACC AAC    10834
Ser Ser Asp Phe Gly Gly Val Leu Thr Leu Thr Tyr Lys Thr Asn
   1125            1130                1135

AAG AAC GGG GAC TGC TCT GTA CAC TCG CAC TCT AAC GTA GCT ACT    10879
Lys Asn Gly Asp Cys Ser Val His Ser His Ser Asn Val Ala Thr
   1140            1145                1150

CTA CAG GAG GCC ACA GCA AAA GTG AAG ACA GCA GGT AAG GTG ACC    10924
Leu Gln Glu Ala Thr Ala Lys Val Lys Thr Ala Gly Lys Val Thr
   1155            1160                1165

TTA CAC TTC TCC ACG GCA AGC GCA TCA CCT TCT TTT GTG GTG TCG    10969
Leu His Phe Ser Thr Ala Ser Ala Ser Pro Ser Phe Val Val Ser
   1170            1175                1180

CTA TGC AGT GCT AGG GCC ACC TGT TCA GCG TCG TGT GAG CCC CCG    11014
Leu Cys Ser Ala Arg Ala Thr Cys Ser Ala Ser Cys Glu Pro Pro
   1185            1190                1195

AAA GAC CAC ATA GTC CCA TAT GCG GCT AGC CAC AGT AAC GTA GTG    11059
Lys Asp His Ile Val Pro Tyr Ala Ala Ser His Ser Asn Val Val
   1200            1205                1210

TTT CCA GAC ATG TCG GGC ACC GCA CTA TCA TGG GTG CAG AAA ATC    11104
Phe Pro Asp Met Ser Gly Thr Ala Leu Ser Trp Val Gln Lys Ile
   1215            1220                1225

TCG GGT GGT CTG GGG GCC TTC GCA ATC GGC GCT ATC CTG GTG CTG    11149
Ser Gly Gly Leu Gly Ala Phe Ala Ile Gly Ala Ile Leu Val Leu
   1230            1235                1240

GTT GTG GTC ACT TGC ATT GGG CTC CGC AGA TAA GTTAGGGTAG         11192
Val Val Val Thr Cys Ile Gly Leu Arg Arg
   1245            1250

GCAATGGCAT TGATATAGCA AGAAAATTGA AAACAGAAAA AGTTAGGGTA AGCAATGGCA    11252

TATAACCATA ACTGTATAAC TTGTAACAAA GCGCAACAAG ACCTGCGCAA TTGGCCCCGT    11312

GGTCCGCCTC ACGGAAACTC GGGGCAACTC ATATTGACAC ATTAATTGGC AATAATTGGA    11372

AGCTTACATA AGCTTAATTC GACGAATAAT TGGATTTTTA TTTTATTTTG CAATTGGTTT    11432

TTAATATTTC CAAAAAAAAA AAAAAAAAAA AAAAAAAAAA AAAAAAAAAA AAAAAAAAAA    11492

AAAAAAAAAA AAAAAAAAAA ACTAG                                           11517
```

```
                                                     BamH1
--- --- --- --- --- --- --- --- --- --- --G GAT CC- --- --- --- --- --- ---            SFV vector E2
AAC TCA CCT TTC GTC CCG AGA GCC GAC GAA CCG GAC GCT AGA AAA GGC AAA GTC CAT             SFV E2
Asn Ser Pro Phe Val Pro Arg Ala Asp Glu Pro Asp Ala Arg Lys Gly Lys Val His             SFV E2
--- --- --- --- --- --- --- --- --- --- --- Glu Asp --- --- --- --- --- ---            SFV vector E2
                                             246 247
```

```
GAT CCG CGT ATC CAG AGA GGA CCA GGA AGA GCA TTT GTT GAG                                 HIV-gp120
GC GCA TAG GTC TCT CCT GGT CCT TCT CGT AAA CAA CTC CTA G                                HIV epitope
Asp Pro Arg Ile Gln Arg Gly Pro Gly Arg Ala Phe Val Glu Asp
                                                  313
```

Cut with BamH1
Insert HIV oligo

➡

```
GAG GAT CCG CGT ATC CAG AGA GGA CCA GGA AGA GCA TTT GTT GAG GAT CCG                     SFV-HIV chimera
CTC CTA GGC GCA TAG GTC TCT CCT GGT CCT TCT CGT AAA CAA CTC CTA GGC
Glu Asp Pro Arg Ile Gln Arg Gly Pro Gly Arg Ala Phe Val Glu Asp Pro
```

DNA EXPRESSION SYSTEMS BASED ON ALPHAVIRUSES

This application is a continuation of application Ser. No. 08/466,277, filed on Jun. 6, 1995 now U.S. Pat. No. 6,190,666 which in turn is a continuation application of application Ser. No. 07/920,281, filed Aug. 13, 1992 (now U.S. Pat. 5,739,026). Application Ser. No. 07/920,281 is the national phase of PCT International Application No. PCT/SE91/00855 filed on Dec. 12, 1991 under 35 U.S.C. § 371. The entire contents of each of the above-identified applications are hereby incorporated by reference.

The present invention is related to DNA expression systems based on alphaviruses, which systems can be used to transform animal cells for use in the production of desired products, such as proteins and vaccines, in high yields.

The rapid development of biotechnology is to a large extent due to the introduction of recombinant DNA technique, which has revolutionized cellbiological and medical research by opening new approaches to elucidate the molecular mechanisms of the cell. With the aid of the techniques of cDNA cloning, large numbers of interesting protein molecules are characterized each year. Therefore, a lot of research activity is today directed to elucidate the relationship between structure and function of these molecules. Eventually this knowledge will increase our possibilities to preserve healthiness and combat diseases in both humans and animals. Indeed, there is today a growing list of new "cloned" protein products that are already used as pharmaceuticals or diagnostics.

In the recombinant DNA approaches to study biological questions, DNA expression systems are crucial elements. Thus, efficient DNA expression systems, which are simple and safe to use, give high yields of the desired product and can be used in a variety of host cells, especially also in mammalian cells, are in great demand.

Many attempts have been made to develop DNA expression systems, which fulfill these requirements. Often, viruses have been used as a source of such systems. However, up to date none of the existing viral expression systems fulfill all these requirements in a satisfying way. For instance, the Baculovirus expression system for cDNA is extremely efficient but can be used only in insect cells (see Reference 1 of the list of cited references; for the sake of convenience, in the following the cited references are only identified by the number they have on said list). As many important molecules will have to be produced and processed in cells of mammalian origin in order for them to become active, this system cannot be used in such cases. Furthermore, the Baculovirus cDNA expression system is not practically convenient for analysis of the relationship between structure and function of a protein because this involves in general the analysis of whole series of mutant variants. Today it takes about 6–8 weeks to construct a single Baculo recombinant virus for phenotype analyses. This latter problem is also true for the rather efficient Vaccinia recombinant virus and other contemporary recombinant virus cDNA expression systems (2,3). The procedure to establish stably transformed cell lines is also a very laborious procedure, and in addition, often combined with very low levels of protein expression.

Hitherto, most attempts to develop viral DNA expression systems have been based on viruses having DNA genomes or retroviruses, the replicative intermediate of the latter being double stranded DNA.

Recently, however, also viruses comprising RNA genomes have been used to develop DNA expression systems.

In EP 0 194 809 RNA transformation vectors derived from (+) strand RNA viruses are disclosed which comprise capped viral RNA that has been modified by insertion of exogenous RNA into a region non-essential for replication of said virus RNA genome. These vectors are used for expression of the function of said exogenous RNA in cells transformed therewith. The RNA can be used in solution or packaged into capsids. Furthermore, this RNA can be used to generate new cells having new functions, i.e. protein expression. The invention of said reference is generally claimed as regards host cells, (+) strand RNA viruses and the like. Nevertheless, it is obvious from the experimental support provided therein that only plant cells have been transformed and in addition only Bromo Mosaic virus, a plant virus, has been used as transformation vector.

Although it is stated in said reference that it is readily apparent to those skilled in the art to convert any RNA virus-cell system to a useful expression system for exogenous DNA using principals described in the reference, this has not been proven to be true in at least the case of animal cell RNA viruses. The reasons for this seem to be several. These include:

1) Inefficiencies in transfecting animal cells with in vitro transcribed RNA;
2) Inefficiency of apparently replication competent RNA transcripts to start RNA replication after commonly used transfection procedures;
3) The inability to produce high titre stocks of recombinant virus that does not contain any helper virus;
4) The inability to establish stable traits of transformed cells expressing the function of the exogenous RNA.

In Proc. Natl. Acad. Sci. USA, Vol 84, 1987, pp 4811–4815 a gene expression system based on a member of the Alphavirus genus, viz. Sindbis virus, is disclosed which is used to express the bacterial CAT (chloramphenicol acetyltransferase) gene in avian cells, such as chicken embryo fibroblasts.

Xiong et al., Science, Vol 243, 1989, 1188–119; also disclose a gene expression system based on Sindbis virus. This system is said to be efficient in a broad range of animal cells. Expression of the bacterial CAT gene in insect, avian and mammalian cells inclusive of human cells is disclosed therein.

Even though it is known from prior art that one member of the Alphavirus genus, the Sindbis virus, can tolerate insertion and direct the expression of at least one foreign gene, the bacterial chloramfenicol acetyl transferase (CAT) gene, it is evident from the results described that both systems described above are both ineffective in terms of exogenous gene expression and also very cumbersome to use. Hence, neither system has found any usage in the field of DNA expression in animal cells today.

In the first example a cDNA copy of a defective interfering (DI) virus variant of Sindbis virus was used to carry the CAT gene. RNA was transcribed in vitro and used to transfect avian cells and some CAT protein production could be demonstrated after infecting cells with wild-type Sindbis virus. The latter virus provided the viral replicase for expression of the CAT construct. The inefficiency of this system depends on 1) low level of initial DI-CAT RNA transfection (0.05–0.5% of cells) and 2) inefficient usage of the DI-CAT RNA for protein translation because of unnatural and suboptimal protein intitation translation signals. This same system also results in packaging of some of the recombinant DI-CAT genomes into virus particles. However, this occurs simultaneously with a very large excess of wild-type Sindbis virus production. Therefore, the usage of this mixed virus stock for CAT expression will be much hampered by the fact that most of the replication and translation activity of the cells infected with such a stock will deal with the wild-type and not with recombinant gene expression.

Much of the same problems are inherent to the other Sindbis expression system described. In this an RNA replication competent Sindbis DNA vector is used to carry the CAT gene. RNA produced in vitro is shown to replicate in animal cells and CAT activity is found. However, as only a very low number of cells are transfected the overall CAT production remains low. Another possible explanation for this is that the Sindbis construct used is not optimal for replication. Wild-type Sindbis virus can be used to rescue the recombinant genome into particles together with an excess of wild-type genomes and this mixed stock can then be used to express a CAT protein via infection. However, this stock has the same problems as described above for the recombinant DI system. The latter paper shows also that if virus is amplified by several passages increased titres of the recombinant virus particles can be obtained. However, one should remember that the titre of the wild-type virus will increase correspondingly and the original problem of mostly wild-type virus production remains. There are also several potential problems when using several passages to produce a mixed virus stock. As there is no selected pressure for preservation of the recombinant genomes these might easily 1) undergo rearrangements and 2) become outnumbered by wild-type genomes as a consequence of less efficient replication and/or packaging properties.

Another important aspect of viral DNA expression vectors is use thereof to express antigens of unrelated pathogens and thus they can be used as vaccines against such pathogens.

Development of safe and effective vaccines against viral diseases has proven to be quite a difficult task. Although many existing vaccines have helped to combat the worldwide spread of many infectious diseases, there is still a large number of infectious agents against which effective vaccines are missing. The current procedures of preparing vaccines present several problems: (1) it is often difficult to prepare sufficiently large amounts of antigenic material; (2) In many cases there is the additional hazard that the vaccine preparation is not killed or sufficiently attenuated; (3) Effective vaccines are often hard to produce since there is a major difficulty in presenting the antigenic epitope in an immunologically active form; (4) In the case of many viruses, genetic variations in the antigenic components results in the evolution of new strains with new serological specificities, which again creates a need for the development of new vaccines.

Two types of viral DNA vectors have been developed in order to overcome many of these problems in vaccine production. These either provide recombinant viruses or provide chimaeric viruses. The recombinant viruses contain a wild-type virus package around a recombinant genome. These particles can be used to infect cells which then produce the antigenic protein from the recombinant genome. The chimaeric viruses also contain a recombinant genome but this specifies the production of an antigen, usually as part of a normal virus structural protein, which then will be packaged in progeny particles and e.g. exposed on the surface of the viral spike proteins. The major advantages of these kind of virus preparations for the purpose of being used as a vaccine are 1) that they can be produced in large scale and 2) that they provide antigen in a natural form to the immunological system of the organism. Cells, which have been infected with recombinant viruses, will synthesize the exogenous antigen product, process it into peptides that then present them to T cells in the normal way. In the case of the chimaeric virus there is, in addition, an exposition of the antigen in the context of the subunits of the virus particle itself. Therefore, the chimaeric virus is also-called an epitope carrier.

The major difficulty with these kind of vaccine preparations are, how to ensure a safe and limited replication of the particles in the host without side effects. So far, some success has been obtained with vaccinia virus as an example of the recombinant virus approach (69) and of polio virus as an example of a chimaeric particle (70–72). As both virus variants are based on commonly used vaccine strains one might argue that they could be useful vaccine candidates also as recombinant respectively chimaeric particles (69–72). However, both virus vaccines are combined with the risk for side effects, even severe ones, and in addition these virus strains have already been used as vaccines in large parts of the population in many countries.

As is clear from the afore mentioned discussion there is much need to develop improved DNA expression systems both for an easy production of important proteins or polypeptides in high yields in various kinds of animal cells and for the production of recombinant viruses or chimaeric viruses to be used as safe and efficient vaccines against various pathogenes.

Thus, an object of the present invention is to provide an improved DNA expression system based on virus vectors which can be used both to produce proteins and polypeptides and as recombinant virus or chimaeric virus, which system offers many advantages over prior art.

To that end, according to the present invention there is provided an RNA molecule derived from an alphavirus RNA genome and capable of efficient infection of animal host cells, which RNA molecule comprises the complete alphavirus RNA genome regions, which are essential to replication of the said alphavirus RNA, and further comprises an exogenous RNA sequence capable of expressing its function in said host cell, said exogenous RNA sequence being inserted into a region of the RNA molecule which is non-essential to replication thereof.

Alphavirus is a genus belonging to the family Togaviridae having single stranded RNA genomes of positive polarity enclosed in a nucleocapsid surrounded by an evelope containing viral spike proteins.

The Alphavirus genus comprises among others the Sindbis virus, the Semliki Forest virus (SFV) and the Ross River virus, which are all closely related. According to a preferred embodiment of the invention, the Semliki Forest virus (SFV) is used as the basis of the DNA expression system.

The exogenous RNA sequence encodes a desired genetic trait, which is to be conferred on the virus or the host cell, and said sequence is usually complementary to a DNA or cDNA sequence encoding said genetic trait. Said DNA sequence may be comprised of an isolated natural gene, such as a bacterial or mammalian gene, or may constitute a synthetic DNA sequence coding for the desired genetic trait i.e. expression of a desired product, such as an enzyme, hormone, etc. or expression of a peptide sequence defining an exogenous antigenic epitope or determinant.

If the exogenous RNA sequence codes for a product, such as a protein or polypeptide, it is inserted into the viral RNA genome replacing deleted structural protein encoding region (s) thereof, whereas a viral epitope encoding RNA sequence may be inserted into structural protein encoding regions of the viral RNA genome, which essentially do not comprise deletions or only have a few nucleosides deleted.

The RNA molecule can be used per se, e.g. in solution to transform animal cells by conventional transfection, e.g. the DEAE-Dextran method or the calcium phosphate precipitation method. However, the rate of transformation of cells, and, thus the expression rate can be expected to increase substantially if the cells are transformed by infection with infectious viral particles. Thus, a suitable embodiment of the invention is related to an RNA virus expression vector comprising the RNA molecule of this invention packaged into infectious particles comprising the said RNA within the alphavirus nucleocapsid and surrounded by the membrane including the alphavirus spike proteins.

The RNA molecule of the present invention can be packaged into such particles without restraints provided that it has a total size corresponding to the wild type alphavirus RNA genome or deviating therefrom to an extent compatible with package of the said RNA into the said infectious particles.

These infectious particles, which include recombinant genomes packaged to produce a pure, high titre recombinant virus stock, provides a means for exogenous genes or DNA sequences to be expressed by normal virus particle infection, which as regards transformation degree, is much more efficient than RNA transfection.

According to a suitable embodiment of the invention such infectious particles are produced by cotransfection of animal host cells with the present RNA which lacks part of or the complete region(s) encoding the structural viral proteins together with a helper RNA molecule transcribed in vitro from a helper DNA vector comprising the SP6 promoter region, those 5' and 3' regions of the alphavirus cDNA which encode cis acting signals needed for RNA replication and the region encoding the viral structural proteins but lacking essentially all of the nonstructural virus proteins encoding regions including sequences encoding RNA signals for packaging of RNA into nucleocapsid particles, and culturing the host cells.

According to another aspect of the invention efficient introduction of the present RNA into animal host cells can be achieved by electroporation. For example, in the case of Baby Hamster Kidney (BHK) cells a transformation degree of almost 100% has been obtained for the introduction of an RNA transcript derived from SFV cDNA of the present invention. This makes it possible to reach so high levels of exogenous protein production in every cell that the proteins can be followed in total cell lysates without the need of prior concentration by antibody precipitation.

By electroporation, it is also possible to obtain a high degree of cotransfection in the above process for production of infectious particles comprising packaged RNA of the present invention. Essentially all animal cells will contain both the present RNA molecule and the helper RNA molecule, which leads to a very efficient trans complementation and formation of infectious partcles. A pure recombinant virus stock, consisting of up to $10^9$–$10^{10}$ infectious particles, can be obtained from $5 \times 10^6$ cotransfected cells after only a 24 h incubation. Furthermore, the so obtained virus stock is very safe to use, since it is comprised of viruses containing only the desired recombinant genome, which can infect host cells but can not produce new progeny virus.

Theoretically, a regeneration of a wild-type virus genome could take place when producing the recombinant virus in the contransfected cells. However, the possibility to avoid spread of such virus can be eliminated by incorporating a conditionally lethal mutation into the structural part of the helper genome. Such a mutation is described in the experimental part of this application. Thus, the virus produced with such a helper will be noninfectious if not treated in vitro under special conditions.

The technique of electroporation is well known within the field of biotechnology and optimal conditions can be established by the man skilled in the art. For instance, a BioRad Gene pulser apparatus (BioRad, Richmond, Calif., USA) can be used to perform said process.

The RNA molecule of the present invention is derived by in vivo or in vitro transcription of a cDNA clone, originally produced from an alphavirus RNA and comprising an inserted exogenous DNA fragment encoding a desired genetic trait.

Accordingly, the present invention is also related to a DNA expression vector comprising a full-length or partial cDNA complementary to alphavirus RNA or parts thereof and located immediately downstream of the SP6 RNA polymerase promoter and having a 5'ATGG, a 5'GATGG or any other 5' terminus and a TTTCCA$_{69}$ACTAGT (SEQ ID NO: 25) or any other 3' terminus.

According to one aspect of the present invention portions of the viral cDNA are deleted, the deletions comprising the complete or part of the region(s) encoding the virus structural proteins, and the vector further comprises an integrated polylinker region, which may correspond to BamHI-SmaI-XmaI, inserted at a location which enables an exogenous DNA fragment encoding a foreign polypeptide or protein to be inserted into the vector cDNA for subsequent expression in an animal host cell.

According to another aspect of this invention, the vector is comprised of full-length cDNA wherein an exogenous DNA fragment encoding a foreign epitopic peptide sequence can be inserted into a region coding for the viral structural proteins.

It is appreciated that this cDNA clone with its exogenous DNA insert is very efficiently replicated after having been introduced into animal cells by transfection.

A very important aspect of the present invention is that it is applicable to a broad range of host cells of animal origin. These host cells can be selected from avian, mammalian, reptilian, amphibian, insect and fish cells. Illustrative of mammalian cells are human, monkey, hamster, mouse and porcine cells. Suitable avian cells are chicken cells, and as reptilian cells viper cells can be used. Cells from frogs and from mosquitoes and flies (Drosophilal) are illustrative of amphibian and insecticidal cells, respectively. A very efficient virus vector/host cell system according to the invention is based on SFV/BHK cells, which will be discussed more in detail further below.

However, even though a very important advantage of the present DNA expression vector is that it is very efficient in a broad variety of animal cells it can also be used in other eucaryotic cells and in procaryotic cells.

The present invention is also related to a method to produce transformed animal host cells comprising transfection of the cells with the present RNA molecule or with the present transcription vector comprised of cDNA and carrying an exogenous DNA fragment. According to a suitable embodiment of the invention, transfection is produced by the above mentioned electroporation method, a very high transfection rate being obtained.

A further suitable transformation process is based on infection of the animal host cells with the above mentioned infectious viral particles comprising the present RNA molecule.

The transformed cells of the present invention can be used for different purposes.

One important aspect of the invention is related to use of the present transformed cells to produce a polypeptide or a protein by culturing the transformed cells to express the exogenous RNA and subsequent isolation and purification of the product formed by said exepression. The transformed cells can be produced by infection with the present viral particles comprising exogenous RNA encoding the polypeptide or protein as mentioned above, or by transfection with an RNA transcript obtained by in vitro transcription of the present DNA vector comprised of cDNA and carrying an exogenous DNA fragment coding for the polypeptide or the protein.

Another important aspect of the invention is related to use of the present transformed cells for the production of antigens comprised of chimaeric virus particles for use as immunizing component in vaccines or for immunization purposes for in vivo production of immunizing components for antisera production.

Accordingly, the present invention is also related to an antigen consisting of a chimaeric alphavirus having an exogenous epitopic peptide sequence inserted into its structural proteins.

Preferably, the chimaeric alphavirus is derived from SFV.

According to a suitable embodiment, the exogenous epitopic peptide sequence is comprised of an epitopic peptide sequence derived from a structural protein of a virus belonging to the immunodeficiency virus class inclusive of the human immunodeficiency virus types.

A further aspect of the invention is related to a vaccine preparation comprising the said antigen as immunizing component.

In said vaccine the chimaeric alphavirus is suitably attenuated by comprising mutations, such as the conditionally lethal SFV-mutation described before, amber (stop codon) or temperature sensitive mutations, in its genome.

For instance, if the chimaeric virus particles containing the aforementoned conditional lethal mutation in its structural proteins (a defect to undergo a certain proteolytical cleavage in host cell during morphogenesis) is used as a vaccine then chimaeric virus particles are first activated by limited proteolytic treatment before being given to the organism so that they can infect recipient cells. New chimaeric particles will be formed in cells infected with the activated virus but these will again have the conditional lethal phenotype and further spread of infection is not possible.

The invention is also concerned with a method for the production of the present antigen comprising a) in vitro transcription of the cDNA of the present DNA vector carrying an exogenous DNA fragment encoding the foreign epitopic peptide sequence and transfection of animal host cells with the produced RNA transcript, or b) transfection of animal host cells with the said cDNA of the above step a), culturing the transfected cells and recovering the chimaeric alphavirus antigen.

Preferably, transfection is produced by electroporation.

Still another aspect of the invention is to use a recombinant virus containing exogenous RNA encoding a polypeptide antigen for vaccination purpose or to produce antisera. In this case the recombinant virus or the conditionally lethal variant of it is used to infect cells in vikvo and antigen production will take place in the infected cells and used for antigen presentation to the immunological system.

According to another embodiment of the invention, the present antigen is produced in an organism by using in vivo infection with the present infectious particles containing exogenous RNA encoding an exogenous epitopic peptide sequence.

BRIEF DESCRIPTION OF THE DRAWINGS

In the following, the present invention will be illustrated more in detail with reference to the Semliki Forest virus (SFV), which is representative for the alphaviruses. This description can be more fully understood in conjunction with the accompanying drawings in which:

FIGS. 4 A–C show the construction of full-length infectious clones of SFV; FIG. 4A shows a schematic restriction map of the SFV genome; primers used for initiating cDNA synthesis are indicated as arrows, and the cDNA inserts used to assemble the final clone are showed as bars; FIG. 4B shows plasmid pPLH211, i.e. the SP6 expression vector used as carrier for the full-length infectious clone of SFV, and the resulting plasmid pSP6-SFV4; FIG. 4C shows the structure of the SP6 (SEQ ID NO:25) promoter area of the SFV clone; the stippled bars indicate the SP6 promoter sequence, and the first necleotide to be transcribed is marked by an asterisk; underlinfed regions denote authentic SFV sequences;

FIGS. 5A–R show the complete nucleotide sequence of the pSP6-SFV4 RNA transcript as DNA (U=T) (SEQ ID NO:1) and underneath the DNA sequence, the amino acid sequence of the non-structural polyprotein (SEQ ID NO: 2) and the structural polyprotein;

FIGS. 12A–12B shows in its upper part sequences encompassing the major antigenic site of SFV and the in vitro made substitutions leading toga BamHI restriction endonuclease site, (SEQ ID NO: 7 and 8) sequences spanning the principal neutralizing domain of the HIV gp120 (SEQ ID NO: 9 and 10) protein, and the HIV domain inserted into the SFV carrier protein E2 as a BamHI oligonucleotide; (SEQ ID NO: 11 and 12) and its lower part is a schematic presentation of the SFV spike structure with blow-ups of domain 246–251 in either wild type or chimaeric form.

The alphavirus Semliki Forest virus (abbreviated SFV in the following text) has for some 20 years been used as model system in both virology and cell biology to study membrane biosynthesis, membrane structure and membrane function as well as protein-RNA interactions (4, 5). The major reason for the use of SFV as such a model is due to its simple structure and efficient replication.

Figure 1:
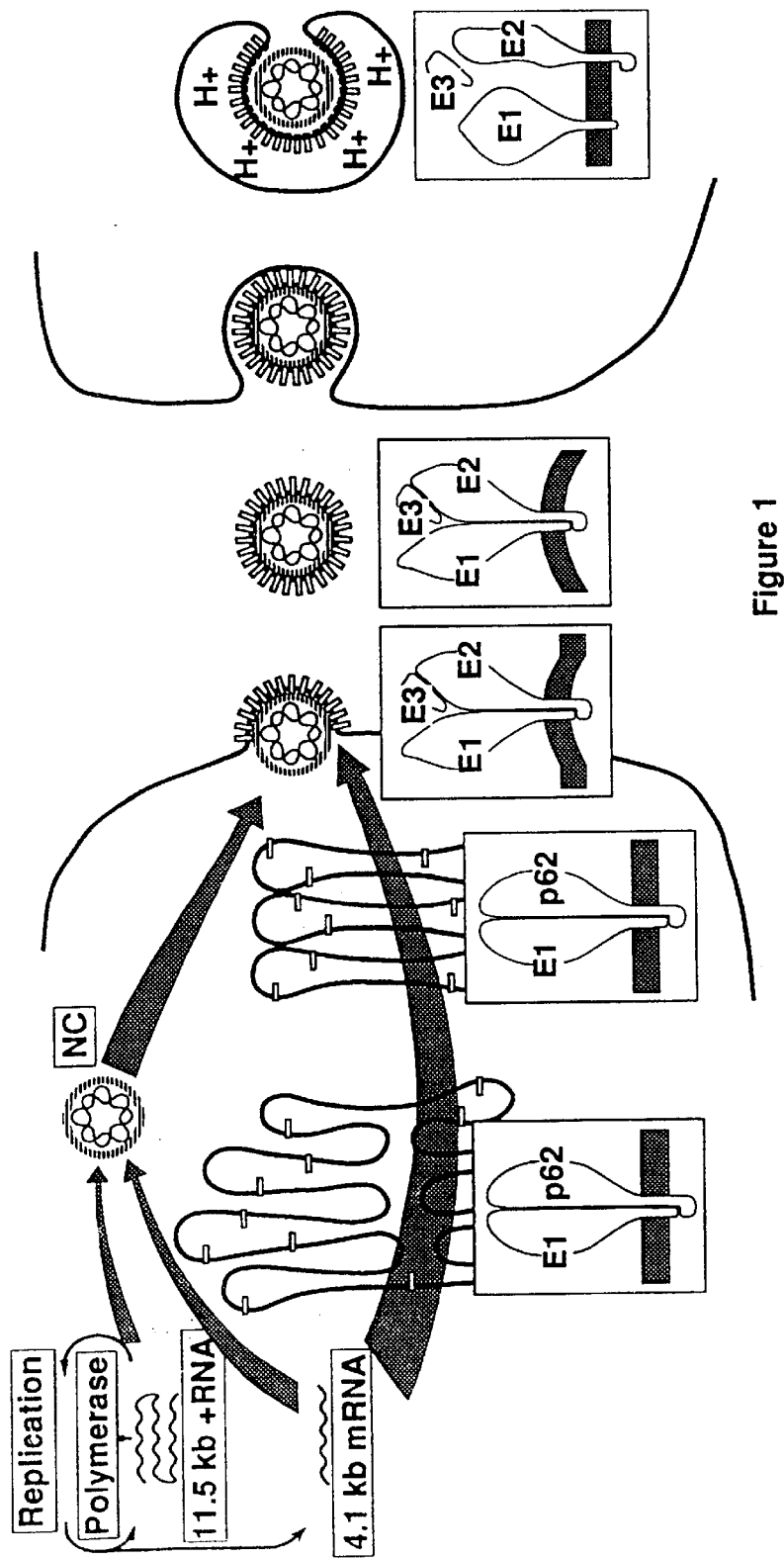
FIG. 1 is a schematic view over the main assembly and disassembly events involved in the life cycle of the Semliki Forest virus, and also shows regulation of the activation of SFV entry functions by p62 cleavage and pH.
Figure 2:
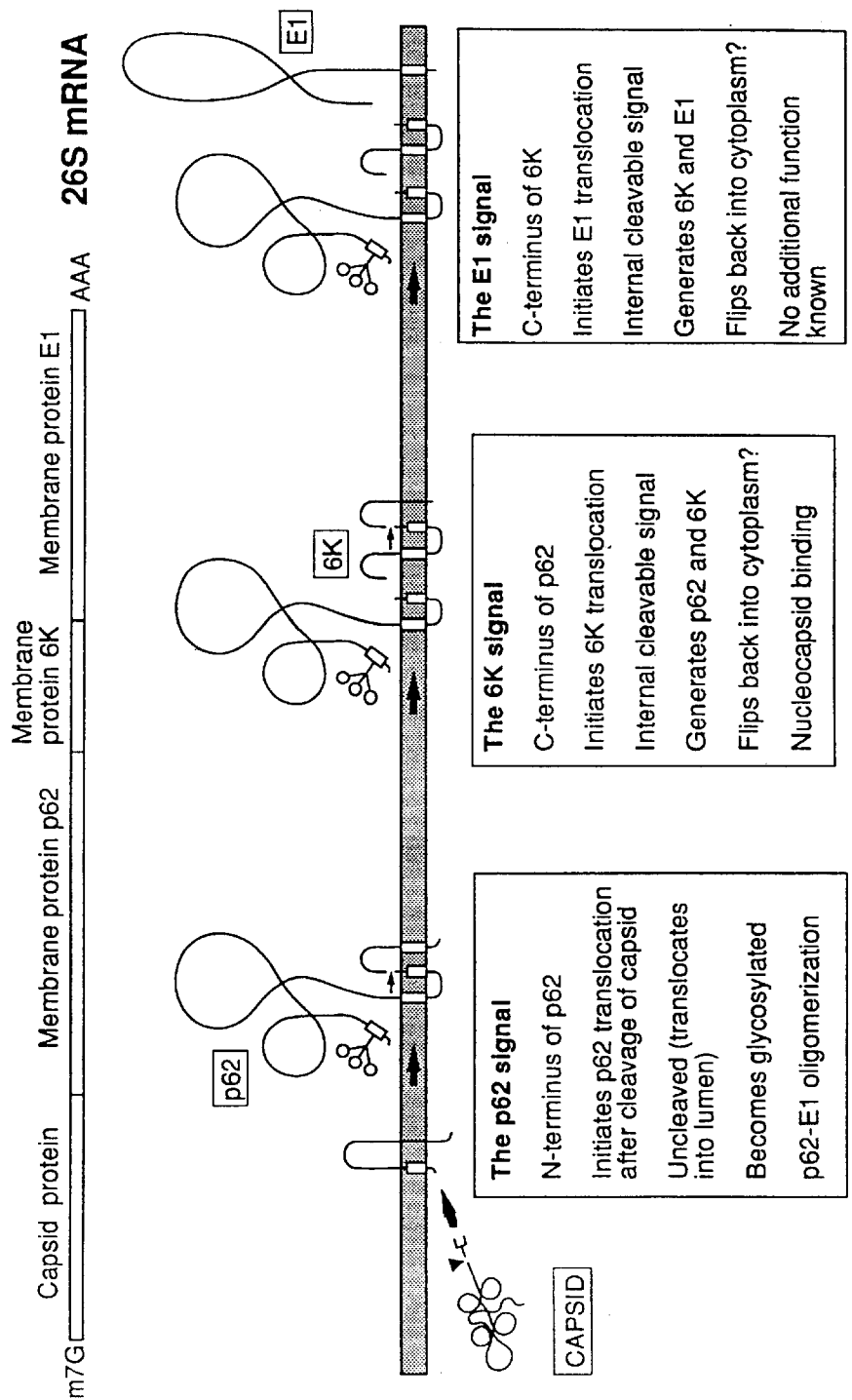
FIG. 2 illustrates the use of translocation signals during synthesis of the structural proteins of SFV; top, the gene map of the 26S subgenomic RNA; middle, the process of membrane translocation of the p62, 6K and E1 proteins; small arrows on the lumenal side denote signal peptidase cleavages; at the bottom, the characteristics of the three signal peptides are listed.
Figure 3:
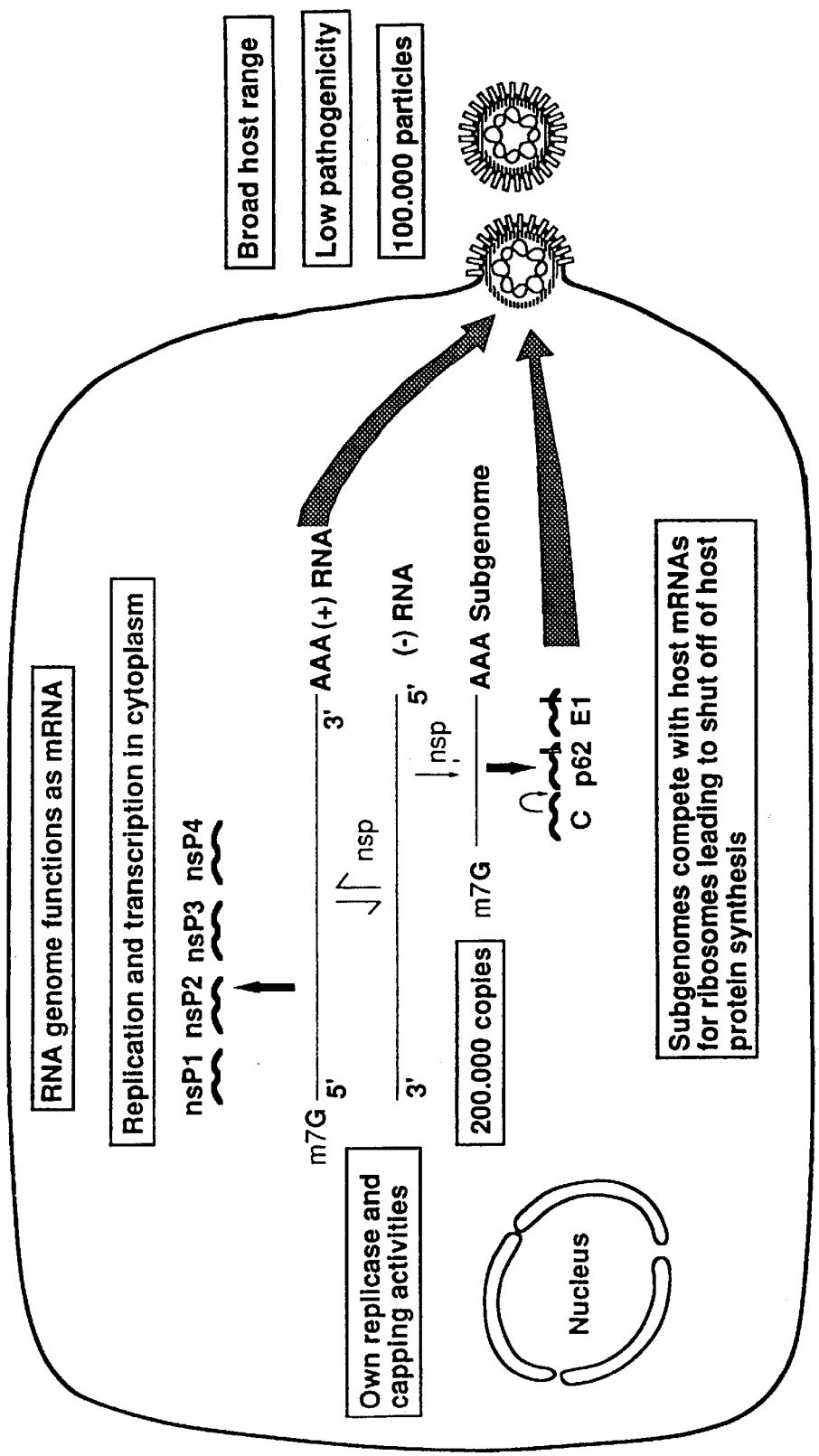
FIG. 3 shows features that make SFV an excellent choice as an expression vector.

With reference to FIG. 1–3, in the following the SFV and its replication are explained more in detail. In essential parts, this disclosure is true also for the other alphaviruses, such as the Sindbis virus, and many of the references cited in this connection are indeed directed to the Sindbis virus. SFV consists of an RNA-containing nucleocapsid and a surrounding membrane composed of a lipid bilayer and proteins, a regularly arranged icosahedral shell of a protein called C protein forming the capsid inside which the genomic RNA is packaged. The capsid is surrounded by the lipid bilayer that contains three proteins called E1, E2, and E3. These so-called envelope proteins are glycoproteins and their glycosylated portions are on the outside of the lipid bilayer, complexes of these proteins forming the "spikes" that can be seen in electron micrographs to project outward from the surface of the virus.

The SFV genome is a single-stranded 5'-capped and 3'-polyadenylated RNA molecule of 11422 nucleotides (6,7). It has positive polarity, i.e. it functions as an mRNA, and naked RNA is able to start an infection when introduced into the cytoplasm of a cell. Infection is initiated when the virus binds to protein receptors on the host cell plasma membrane, whereby the virions become selectively incorporated into "coated pits" on the surface of the plasma membrane, which invaginate to form coated vesicles inside the cell, whereafter said vesicles bearing endocytosed virions rapidly fuse with organelles called endosomes. From the endosome, the virus escapes into the cell cytosol as the bare nucleocapsid, the viral envelope remaining in the endosome. Thereafter, the nucleocapsid is "uncoated" and, thus, the genomic RNA is released. Referring now to FIG. 1, infection then proceeds with the translation of the 5' two-thirds of the genome into a polyprotein which by self-cleavage is processed to the four nonstructural proteins nsP1–4 (8). Protein nsP1 encodes a methyl transferase which is responsible for virus-specific capping activity as well as initiation of minus strand synthesis (9, 10); nsP2 is the protease that cleaves the polyprotein into its four subcomponents (11, 12); nsP3 is a phosphoprotein (13, 14) of as yet unknown function, and nsP4 contains the SFV RNA polymerase activity (15, 16). Once the nsP proteins have been synthesized they are responsible for the replication of the plus strand (42S) genome into full-length minus strands. These molecules then serve as templates for the production of new 42S genomic RNAs. They also serve as templates for the synthesis of subgenomic (26S) RNA. This 4073 nucleotides long RNA is colinear with the last one-third of the genome, and its synthesis is internally initiated at the 26S promoter on the 42S minus strands (17, 18).

The capsid and envelope proteins are synthesized in different compartments, and they follow separate path-ways through the cytoplasm, viz. the envelope proteins are synthesized by membrane-bound ribosomes attached to the rough endoplasmic reticulum, and the capsid protein is synthesized by free ribosomes in the cytosol. However, the 26S RNA codes for all the structural proteins of the virus, and these are synthesized as a polyprotein precursor in the order C-E3-E2-6K-E1 (19). Once the capsid (C) protein has been synthesized it folds to act as a protease cleaving itself off the nascent chain (20, 21). The synthesized C proteins bind to the recently replicated genomic RNA to form new nucleocapsid structures in the cell cytoplasm.

The said cleavage reveals an N-terminal signal sequence in the nascent chain which is recognized by the signal recognition particle targeting the nascent chain-ribosome complex to the endoplasmic reticulum (ER) membrane (22, 23), where it is cotranslationally translocated and cleaved by signal peptidase to the three structural membrane proteins p62 (precursor form of E3/E2), 6K and E1 (24, 25). The translocational signals used during the synthesis of the structural proteins are illustrated in FIG. 2. The membrane proteins undergo extensive posttranslational modifications within the biosynthetic transport pathway of the cell. The p62 protein forms a heterodimer with E1 via its E3 domain in the endoplasmic reticulum (26). This dimer is transported out to the plasma membrane, where virus budding occurs through spike nucleocapsid interactions. At a very late (post-Golgi) stage of transport the p62 protein is cleaved to E3 and E2 (27), the forms that are found in mature virions. This cleavage activates the host cell binding function of the virion as well as the membrane fusion potential of E1. The latter activity is expressed by a second, low-pH activation step after the virus enters the endosomes of a new host cell and is responsible for the release of the viral nucleocapsid into the cell cytoplasm (28–32). The mature virus particles contain one single copy of the RNA genome encapsidated within 180 copies of the capsid protein in a T=3 symmetry, and is surrounded by a lipid bilayer carrying 240 copies of the spike trimer protein consisting of E1+E2+E3 arranged in groups of three in a T=4 symmetry (33).

The SFV entry functions are activated and regulated by p62 cleavage and pH. More specifically, the p62-E1 heterodimers formed in the ER are acid resistant. When these heterodimers are transported to the plasma membrane via the Golgi complex the E1 fusogen cannot be activated in spite of the mildly acidic environment, since activation requires dissociation of the complex. As is illustrated in FIG. 1, the released virus particles contain E2E1 complexes. Since the association between E2 and E1 is sensitive to acidic pH, during entry of the virus into a host cell through endocytosis the acidic milieu of the endosome triggers the dissociation of the spike complex (E1 E2 E3) resulting in free E1. The latter can be activated for the catalysis of the fusion process between the viral and endosomal membranes in the infection process as disclosed above.

As indicated in the preceding parts of the disclosure, the alphavirus system, and especially the SFV system, has several unique features which are to advantage in DNA expression systems. These are summarized below with reference to FIG. 3.

1. Genome of positive polarity. The SFV RNA genome is of positive polarity, i.e. it functions directly as mRNA, and infectious RNA molecules can thus be obtained by transcription from a full-length cDNA copy of the genome.

2. Efficient replication. The infecting RNA molecule codes for its own RNA replicase, which in turn drives an efficient RNA replication. Indeed, SFV is one of the most efficiently replicating viruses known. Within a few hours up to 200.000 copies of the plus-RNAs are made in a single cell. Because of the abundance of these molecules practically all ribosomes of the infected cell will be enrolled in the synthesis of the virus encoded proteins, thus overtaking host protein synthesis (34), and pulse-labelling of infected cells results in almost exclusive labelling of viral proteins. During a normal infection $10^5$ new virus particles are produced from one single cell, which calculates to at least $10^8$ protein molecules encoded by the viral genome (5).

3. Cytoplasmic replication. SFV replication occurs in the cell cytoplasm, where the virus replicase transcribes and caps the subgenomes for production of the structural proteins (19). It would obviously be very valuable to include this feature in a cDNA expression system to eliminate the many problems that are encountered in the conventional "nuclear" DNA expression systems, such as mRNA splicing, limitations in transcription factors, problems with capping efficiency and mRNA transport.

4. Late onset of cytopathic effects. The cytopathic effects in the infected cells appear rather late during infection. Thus, there is an extensive time window from about 4 hours after infection to up to 24 hours after infection during which a very high expression level of the structural proteins is combined with negligible morphological change.

5. Broad host range. This phenomenon is probably a consequence of the normal life cycle which includes transmission through arthropod vectors to wild rodents and birds in nature. Under laboratory conditions, SFV infects cultured mammalian, avian, reptilian and insect cells (35) (Xiong, et al, loc. cit.)

6. In nature SFV is of very low pathogenicity for humans. In addition, the stock virus produced in tissue culture cells is apparently apathogenic. By means of specific mutations it is possible to create conditionally lethal mutations of SFV, a feature that is of great use to uphold safety when mass production of virus stocks is necessary.

In the nucleotide and amino acid sequences the following abbreviations have been used in this specification:

Ala, alanine; Ile, isoleucine; leu, leucine; Met, methionine; Phe, phenylalanine; Pro, proline; Trp, tryptophan; Val, valine; Asn, asparagine; Cys, cysteine; Gln, glutamine; Gly, glycine; Ser, serine; Thr, threonine; Tys, tyrosine; Arg, arginine; His, histidine; Lys, lysine; Asp, aspartic acid; Glu, glutamic acid; A, adenine; C, cytosine; G, guanine; T, thymine; U, uracil.

The materials and the general methodology used in the following examples are disclosed below.

1. Materials. Most restriction enzymes, DNA Polymerase I, Klenow fragment, calf intestinal phosphatase, T4 DNA ligase and T4 Polynucleotide kinase were from Boehringer (Mannheim, FRG). SphI, StuI and KpnI together with RNase inhibitor (RNasin) and SP6 Polymerase were from Promega Biotec (Madison, Wis.). Sequenase (Modified T7 polymerase) was from United States Biochemical (Cleveland, Ohio). Proteinase K was from Merck (Darmstadt, FRG). Ribonucleotides, deoxyribonucleotides, dideoxyribonucleotides and the cap analogue m$^7$G(5')ppp (5')G were from Pharmacia (Sweden). Oligonucleotides were produced using an Applied Bio-systems synthesizer 380B followed by HPLC and NAP-5 (Pharmacia) purification. Spermidine, phenylmethylsulfonyl fluoride (PMSF), diethylpyrocarbonate (DEPC), bovine serum albumin (BSA), creatine phosphate and creatine phosphokinase were from Sigma (St. Louis, Mo.). Pansorbin was from CalBiochem (La Jolla, Calif.). Agarose was purchased from FMC BioProducts (Rockland, Me.), and acrylamide from BioRad (Richmond, Calif.). L-[$^{35}$S]-methionine and α-[$^{35}$S]-dATP-α-S were from Amersham.

2. Virus growth and purification: BHK-21 cells were grown in BHK medium (Gibco Life Technologies, Inc., New York) supplemented with 5% fetal calf serum, 10% tryptose phosphate broth, 10 mM HEPES (N-2-hydroxyethylpiperazine-N'-2-ethanesulfonic acid) and 2 mM glutamine. 90% confluent monolayers were washed once with PBS and infected with SFV in MEM containing 0.2% bovine serum albumin (BSA), 10 mM HEPES and 2 mM glutamine at a multiplicity of 0.1. Twenty-four hours post infection (p.i.) the medium was collected and cell debris removed by centrifugation at 8,000×g for 20 min at 4° C. The virus was pelleted from the medium by centrifugation at 26,000 rpm for 1.5 h in an SW28 rotor at 4° C. The virus was resuspended in TN containing 0.5 mM EDTA.

3. Metabolic labeling and immunoprecipitation. Confluent monolayers of BHK cells grown in MEM supplemented with 10 mM HEPES, 2 mM glutamine, 0.2% BSA, 100 IU/mol of penicillin and 100 μg/ml streptomycin, were infected at a multiplicity of 50 at 37° C. After 1 h p.i. the medium was replaced with fresh medium and growth continued for 3.5 h. The medium was removed and cells washed once with PBS and overlayed with methionine-free MEM containing 10 mM HEPES and 2 mM glutamine. After 30 min at 37° C. the medium was replaced with the same containing 100 μCi/ml of [$^{35}$S]methionine (Amersham) and the plates incubated for 10 min at 37° C. The cells were washed twice with labeling medium containing 10× excess methionine and then incubated in same medium for various times. The plates were put on ice, cells washed once with ice-cold PBS and finally lysis buffer (1% NP-40-50 mM Tris-HCl, pH 7.6-150 mM NaCl-2 mM EDTA) containing 10 μg/ml PMSF (phenylmethylsulfonyl fluoride) was added. Cells were scraped off the plates, and nuclei removed by centrifugation at 6,000 rpm for 5 min at 4° C. in an Eppendorf centrifuge. Immunoprecipitations of proteins was performed as described (31). Briefly, antibody was added to lysate and the mixture kept on ice for 30 min. Complexes were recovered by binding to Pansorbin for 30 min on ice. Complexes were washed once with low salt buffer, once with high salt buffer, and once with 10 mM Tris-HCl, pH 7.5, before heating with gel loading buffer. To immunoprecipitate particular proteins, SDS was added to 0.1% and the mixture heated to 95° C. for 2 min followed by addition of 10 volumes of lysis buffer. Antibodies employed for the immunoprecipitation are as follows. Anti-E1 [8.139], anti-E2 [5.1] (36), and anti-C [12/2] (37) monoclonals have been described. The human transferrin receptor was precipitated with the monoclonal antibody OKT-9 in ascites fluid. This preparation was provided by Thomas Ebel at our laboratory using a corresponding hybridoma cell line obtained from ATCC (American Type Culture Collection) No CRL 8021. Polyclonal rabbit anti-mouse dhfr was a kind gift from E. Hurt (European Molecular Biology Laboratory, Heidelberg, FRG) and rabbit anti-lysozyme has been described (38).

4. Immunofluorescence. To perform indirect immunofluorescence, infected cell monolayers on glass coverslips were rinsed twice with phosphate-buffered saline (PBS) and fixed in −20° C. methanol for 6 min. After fixation, the methanol was removed and the coverslip washed 3 times with PBS. Unspecific antibody binding was blocked by incubation at room temperature with PBS containing 0.5% gelatin and 0.25% BSA. The blocking buffer was removed and replaced with same buffer containing primary antibody. After 30 min at room temperature the reaction was stopped by washing 3 times with PBS. Binding of secondary antibody (FITC-conjugated sheep anti-mouse [BioSys, Compiégne, France]) was done as for the primary antibody. After 3 washes with PBS and one rinse with water the coverslip was allowed to dry before mounting in Moviol 4-88 (Hoechst, Frankfurt am Main, FRG) containing 2.5% DABCO (1,4-diazobicyclo-[2.2.2]-octane).

5. DNA procedures. Plasmids were grown in Escherichia coli DH5α (Bethesda Research Laboratories) [recA endA1 gyrA96 thi1 hsdR17 supE44 relA1 Δ(lacZYA-argF) U169 φ80dlacZΔ(M15)]. All basic DNA procedures were done essentially as described (39). DNA fragments were isolated from agarose gels by the freeze-thaw method (40) including 3 volumes of phenol during the freezing step to increase yield and purity. Fragments were purified by benzoyl-naphthoyl-DEAE (BND) cellulose (Serva Feinbiochemica, Heidelberg, FRG) chromatography (41). Plasmids used for production of infectious RNA were purified by sedimentation through 1 M NaCl followed by banding in CsCl (39). In some cases plasmids were purified by Qiagen chromatography (Qiagen Gmbh, Düisseldorf, FRG).

6. Site-directed oligonucleotide mutagenesis. For oligonucleotide mutagenesis, relevant fragments of the SFV cDNA clone were subcloned into M13mp18 or mp 19 (42) and transformed (43) into DH5αFIQ [endA1 hsdR1 supE44 thi1 recA1 gyrA96 relA1 φ80dlacΔ(M15) Δ(lacZYA-argF) U169/F'proAB lacl$^q$ lacZΔ(M15) Tn 5] (Bethesda Research Laboratories). RF DNA from these constructs was transformed into RZ1032 (44) [Hfr KL16 dut1 ung1 thi1 relA1 supE44 zbd279:Tn10.], and virus grown in the presence of uridine to incorporate uracil residues into the viral genome. Single stranded DNA was isolated by phenol extraction from PEG precipitated phage. Oligonucleotides were synthesized on an Applied Biosystems 380B synthesizer and purified by gel filtration over NAP-5 columns (Pharmacia). The oligonucleotides 5'-CGGCCAGTGAATTCTGATTGGAT-CCCGGGTAATTAATTGAATTACATCCCTACGCAAAC-G, (SQE ID NO: 13) 5'-GCGCACTATTATAGCACCGGC-TCCCGGGTAATTAATTGACGCAAACGTTTTA-CGGCCGCCGG (SEQ ID NO: 14) and 5'-GCGCA-CTATTATAGCACCATGGATCCGGGTAATTAATTGA-CGTTTTACGGCCGCCGGTGGCG (SEQ ID NO: 15) were used to insert the new linker sites [BamHI-SmaI-XmaI] into the SFV cDNA clone. The oligonucleotides 5'-CGGCGGTCCTAGATTGGTGCG (SEQ ID NO: 16) and 5'-CGCGGGCGCCACCGGCGGCCG (SEQ ID NO: 17) were used as sequencing primers (SP1 and SP2) up- and downstream of the polylinker site. Phosphorylated oligonucleotides were used in mutagenesis with Sequenase (Unites States Biochemicals, Cleveland, Ohio) as described earlier (44, 45). In vitro made RF forms were transformed into DH5αF'IQ and the resulting phage isolates analyzed for the presence of correct mutations by dideoxy sequencing according to the USB protocol for using Sequenase. Finally, mutant fragments were reinserted into the full-length SFV cDNA clone. Again, the presence of the appropriate mutations was verified by sequencing from the plasmid DNA. Deletion of the 6K region has been described elsewhere.

7. In vitro transcription. SpeI linearized plasmid DNA was used as template for in vitro transcription. RNA was synthesized at 37° C. for 1 h in 10–50 μl reactions containing 40 mM Tris-HCl (pH 7.6), 6 mM spermidine-HCl, 5 mM dithiothreitol (DTT), 100 μg/ml of nuclease free BSA, 1 mM each of ATP, CTP and UTP, 500 μM of GTP; 1 unit/μl of RNasin and 100–500 units/ml of SP6 RNA polymerase. For production of capped transcripts (46), the analogs m$^7$G(5') ppp(5')G or m$^7$G(5')ppp(5')A were included in the reaction at 1 mM. For quantitation of RNA production, trace amounts of [α-$^{32}$P]-UTP (Amersham) were included in the reactions and incorporation measured from trichloroacetic acid precipitates. When required, DNA or RNA was digested at 37° C. for 10 min by adding DNase 1 or RNase A at 10 units/μg template or 20 μg/ml respectively.

8. RNA transfection. Transfection of BHK monolayer cells by the DEAE-Dextran method was done as described previously (47). For transfection by electroporation, RNA was added either directly from the in vitro transcription reaction or diluted with transcription buffer containing 5 mM DTT and 1 unit/μl of RNasin. Cells were trypsinized, washed once with complete BHK-cell medium and once with ice-cold PBS (without MgCl$_2$ and CaCl$_2$) and finally resuspended in PBS to give 10$^7$ cells/ml. Cells were either used directly or stored (in BHK medium) on ice over night. For electroporation, 0.5 ml of cells were transferred to a 0.2 cm cuvette (BioRad), 10–50 μl of RNA solution added and the solution mixed by inverting the cuvette. Electroporation was performed at room temperature by two consecutive pulses at 1.5 kV/25 μF using a BioRad Gene Pulser apparatus with its pulse controller unit set at maximum resistance. After incubation for 10 min, the cells were diluted 1:20 in complete BHK-cell medium and transferred onto tissue culture plates. For plaque assays, the electroporated cells were plated together with about 3×10$^5$ fresh cells per ml and incubated at 37° C. for 2 h, then overlayed with 1.8% low melting point agarose in complete BHK-cell medium. After incubation at 37° C. for 48 h, plaques were visualized by staining with neutral red.

9. Gel electrophoresis. Samples for sodium dodecyl sulfate-polyacrylamide gel electrophoresis (SDS-PAGE) were prepared and run on 12% separating gels with a 5% stacking gel as previously described (48). For resolving the 6K peptide, a 10%–20% linear acrylamide gradient gel was used. Gels were fixed in 10% acetic acid-30% methanol for 30 min before exposing to Kodak XAR-5 film. When a gel was prepared for fluorography (49), it was washed after fixation for 30 min in 30% methanol and then soaked in 1M sodium salicylate-30% methanol for 30 min before drying. Nucleic acids were run on agarose gels using 50 mM Tris-borate-2.5 mM Na$_2$EDTA as buffer. For staining 0.2 μg/ml of ethidium bromide was included in the buffer and gel during the run.

EXAMPLE 1

In this example a full-length SFV cDNA clone is prepared and placed in a plasmid containing the SP6 RNA polymerase promoter to allow in vitro trancription of full-length and infectious transcripts. This plasmid which is designated pSP6-SFV4 has been deposited on 28 Nov. 1991 at PHLS Centre for Applied Microbiology & Research European Collection of Animal Cell Cultures, Porton Down, Salisbury, Wiltshire, U.K:, and given the provisional accession number 91112826.

As illustrated in FIG. 4A–C the strategy for construction the SFV clone was to prime cDNA synthesis on several positions along the template RNA downstream of suitable restriction endonuclease sites defined by the known nucleotide sequence of the SFV RNA molecule. Virus RNA was isolated by phenol-chloroform extraction from purified virus (obtainable among others from the Arbovirus collection in Yale University, New Haven, USA) and used as template for cDNA synthesis as previously described (50). First strand synthesis was primed at three positions, using 5'-TTTCTCGTAGTTCTCCTCGTC (SEQ ID NO: 18) as primer-1 (SFV coordinate 2042–2062) and 5'-GTTATCCCAGTGGTTGTTCTCGTAATA (SEQ ID NO: 19) as primer-2 (SFV coordinate 3323–3349) and an oligo-dT$_{12-18}$ as primer-3 (3' end of SFV) FIG. 4A).

Figure 6:
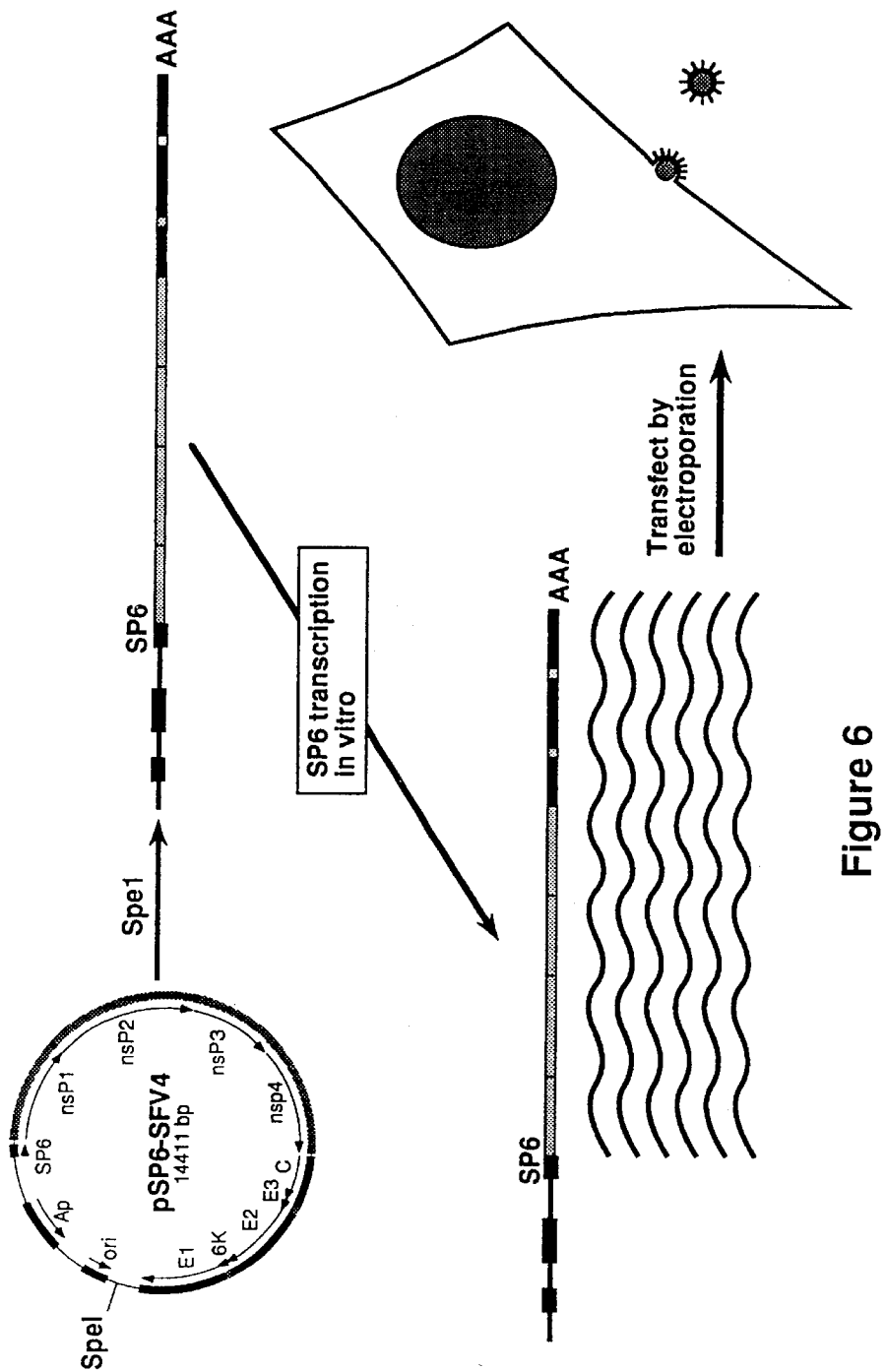
FIG. 6 shows an SFV cDNA expression system for the production of virus after transfection of in vitro made RNA into cells.

Second strand synthesis was preceded by hybridization of the oligonucleotide 5$^1$-ATGGCGGATGTGTGACAT-ACACGACGCC (SEQ ID NO: 20, identical to the 28 first bases of the genome sequence of SFV) to the first strand cDNA. After completion of second strand synthesis cDNA was trimmed and in all cases except in the case of the primer-1 reaction, the double-stranded adaptor 5'-AATTCAAGCTTGCGGCCGCACTAGT/GTTC- GAACGCCGGCGTGATCA-3' (SEQ ID NO: 21) (5'-sticky-EcoRI-HindIII-NotI-XmaIII-SpeI-blunt-3') was added and the DNA cloned into EcoRl cleaved pTZ18R (Pharmacia, Sweden) as described (51). The cloning of the 5' end region was done in a different way. Since SFV contains a HindIII site at position 1947, cDNA primed with primer-1 should contain this area and therefore HindIII could be used to define the 3' end of that cDNA. To obtain a restriction site at the very 5' end of the SFV, cDNA was cloned into SmaI-HindIII cut pGEM1 (Promega Biotec., Madison, Wis.). Since the SFV genome starts with the sequence 5'-ATGG, ligation of this onto the blunt CCC-3' end of the SmaI site created an NcoI site C'CATGG. Although the SFV sequence contains 3 NcoI sites, none of these are within the region preceding the HindIII site, and thus these 5' end clones could be further subcloned as NcoI-HindIII fragments into a vector especially designed for this purpose (see below). The original cDNA clones in pGEM1 were screened by restriction analysis and all containing inserts bigger than 1500 bp were selected for further characterization by sequencing directly from the plasmid into both ends of the insert, using SP6 or T7 sequencing primers. The SFV 5'-end clones in pTZ18R were sequenced using lac sequencing primers. To drive in vitro synthesis of SFV RNA the SP6 promoter was used. Cloning of the SFV 5' end in front of this promoter without adding too many foreign nucleotides required that a derivative of pGEM1 had to be constructed. Hence, pGEM1 was opened at EcoRl and Bal31 deletions were created, the DNA blunted with T4 DNA poqlymerase and an NcoI oligonucleotide (5'-GCCATGGC, (SEQ ID NO: 22) added. The clones obtained were screened by colony hybridization (39) with the oligonucleotide 5'-GGTGACACTATAGCCATGGC (SEQ ID NO: 23) designed to pick up (at suitable stringency) the variants that had the NcoI sequence immediately at the transcription initiation site of the SP6 promoter (G underlined). Since the Bal31 deletion had removed all restriction sites of the multicloning site of the original plasmid, these were restored by cloning a PvuI-NcoI fragment from the new variant into another variant of pGEM1 (pDH101) that had an NcoI site inserted at its HindIII position in the polylinker. This created the plasmid pDH201. Finally, the adaptor used for cloning the SFV cDNA was inserted into pDH201 between the EcoRI and PvuII sites to create plasmid pPLH211 (FIG. 4B). This plasmid was then used as recipient for SFV cDNA fragments in the assembly of the full-length clone by combining independent overlapping subclones using these sites. The fragments and the relevant restriction sites used to assemble the full-length clone, pSP6-SFV4, are depicted in (FIG. 4A). For the 5'-end, the selected fragment contained the proper SFV sequence 5'-ATGG, with one additional G-residue in front. When this G-residue was removed it reduced transcription efficiency from SP6 but did not affect infectivity of the in vitro made RNA. Thus, the clone used for all subsequent work contains the G-residue at the 5' end. For the 3'-end of the clone, a cDNA fragment containing 69 A-residues was selected. By inclusion of the unique SpeI site at the 3'-end of the cDNA, the plasmid can be linearized to allow for runoff transcription in vitro giving RNA-carrying 70 A-residues. FIG. 4C shows the 5' and 3' border sequences of the SFV cDNA clone. The general outline how to obtain and demonstrate infectivity of the full-length SFV RNA is depicted in FIG. 6. The complete nucleotide sequence of the pSP6-SFV4 SP6 transcript together with the amino acid sequences of the nonstructural and the structural polyproteins is shown in FIGS. 5A–R have.

Typically, about 5 μg of RNA per 100 ng of template was obtained using 10 units of polymerase, but the yield could be increased considerably by the use of more enzyme. The conditions slightly differ from those reported earlier for the production of infectious transcripts of alphaviruses (52) (47). A maximum production of RNA was obtained with rNTP concentrations at 1 mM. However, since infectivity also is dependent on the presence of a 5'cap structure optimal infectivity was obtained when the GTP concentration in the transcription reaction was halved. This drop had only a marginal effect on the amounts of RNA produced but raised the specific infectivity by a factor of 3 (data not shown).

The cDNA sequence shown in FIGS. 5A–R have has been used in the following examples. However, sequences having one or a few nucleotides, which differ from those shown in FIGS. 5A–R, could also be useful as vectors, even if these might be less efficient as illustrated above with the SFV cDNA sequence lacking the first 5'-G nucleotide in FIGS. 5A–R.

EXAMPLE 2

In this example the construction of SFV DNA expression vectors is disclosed.

The cDNA clone coding for the complete genome of SFV obtained in Example 1 was used to construct a SFV DNA expression vector by deletion of the coding region of the 26S structural genes to make way for heterologous inserts. However, the nonstructural coding region, which is required for the production of the nsP1–4 replicase complex is preserved. RNA replication is dependent on short 5' (nt 1–247) (53, 54, 55) and 3' (nt 11423–11441) sequence elements (56, 57), and therefore, also these had to be included in the vector construct, as had the 26S promoter just upstream of the C gene (17, 18).

Figure 7A:
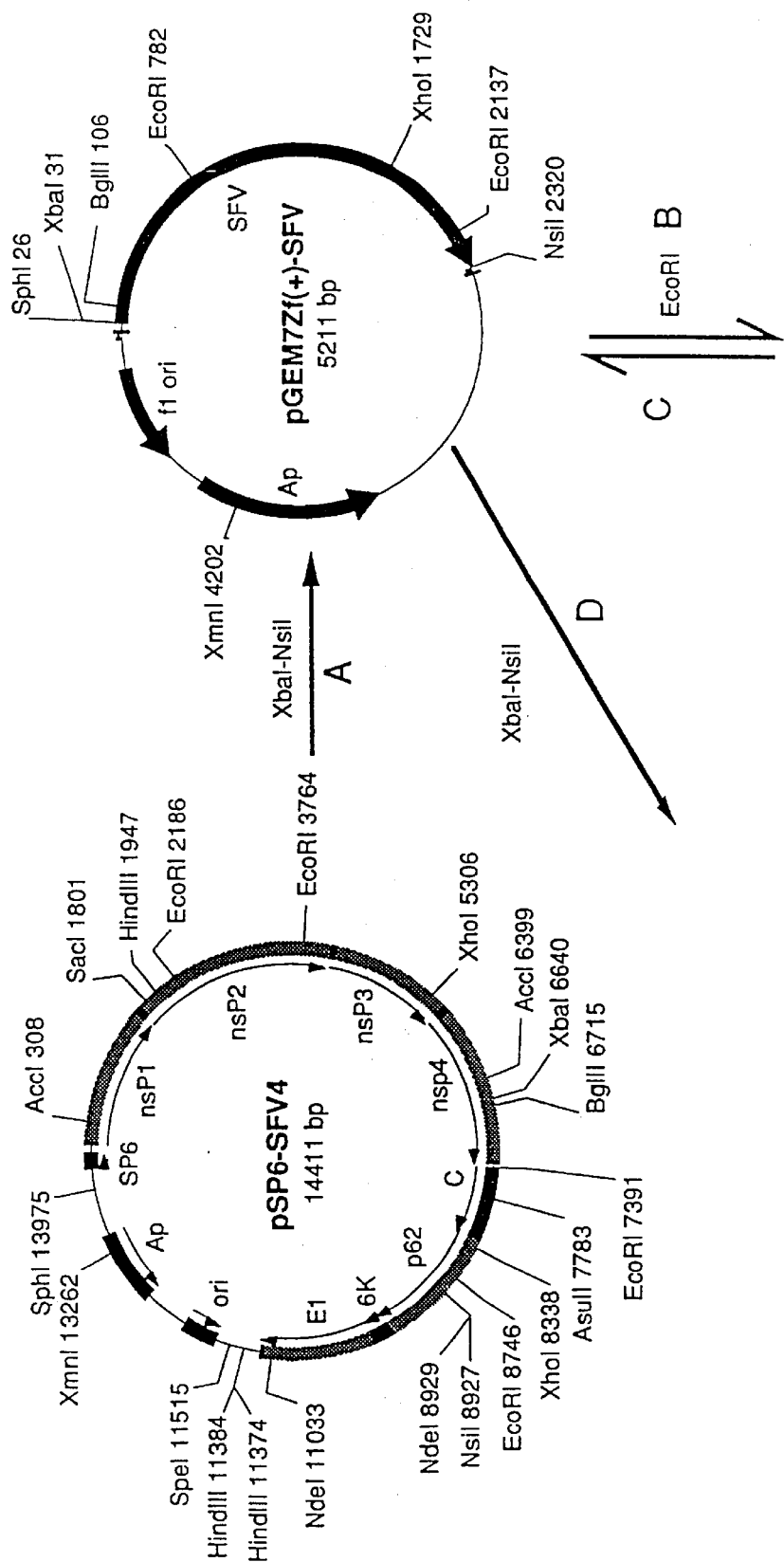
FIGS. 7A–C show the construction of the SFV expression vectors pSFV1–3 and of the Helper 1.
Figure 7B:
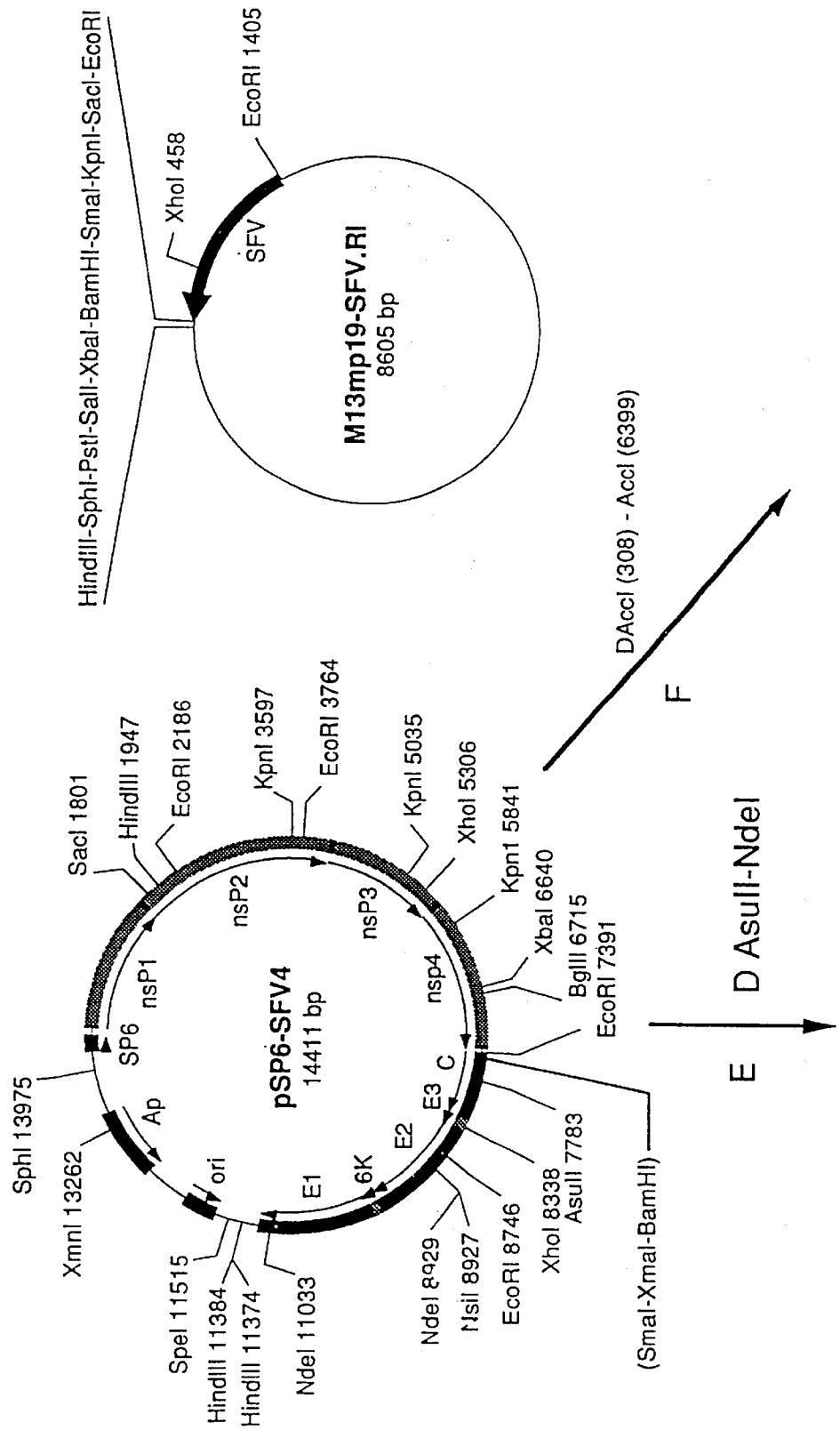
Figure 7C:
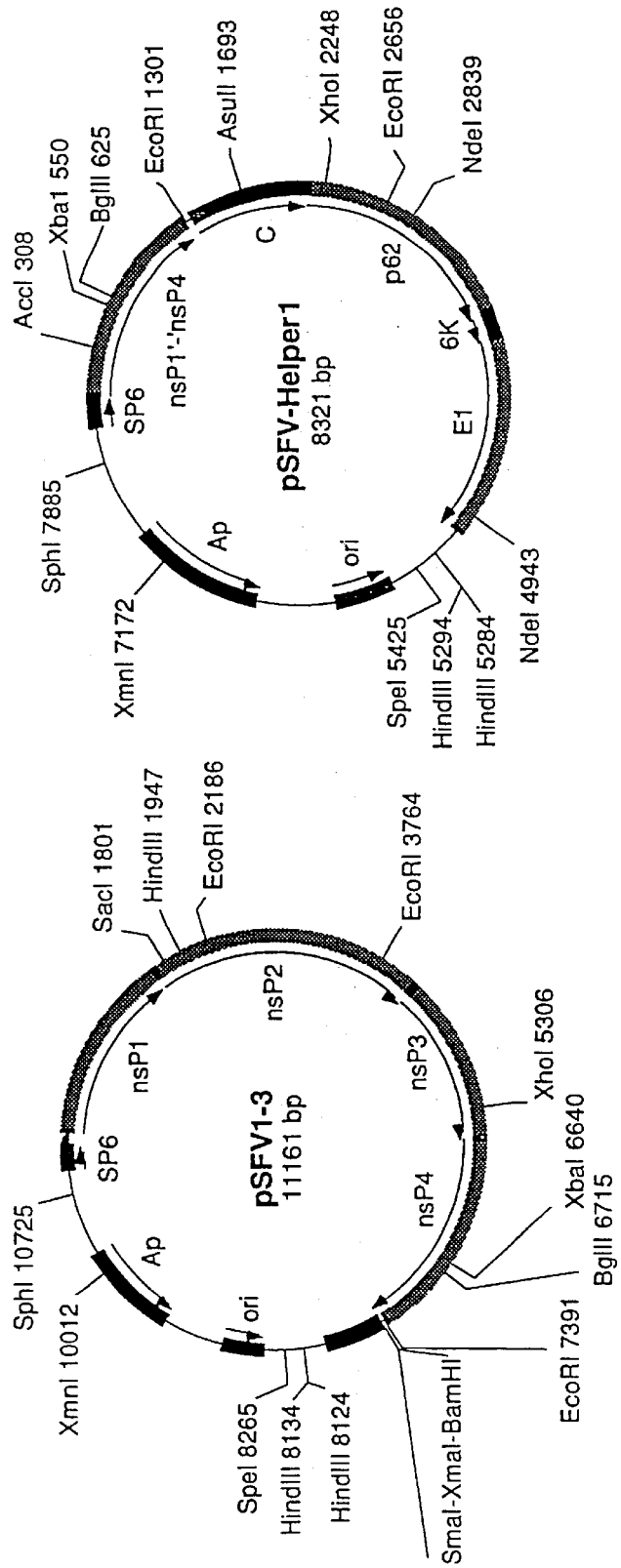

As is shown in FIGS. 7A–C, first, the XbaI (6640)-NsiI (8927) fragment from the SFV cDNA clone pSP6-SFV4 from Example 1 was cloned into pGEM7Zf(+)(Promega Corp., WI, USA) (Step A). From the resulting plasmid, pGEM7Zf(+)-SFV, the EcoRI fragment (SFV coordinates 7391 and 88746) was cloned into M13mp19 to insert a BamHI-XmaI-SmaI polylinker sequence immediately downstream from the 26S promoter site using site-directed mutagenesis (step B). Once the correct mutants had been verfied by sequencing from M13 ssDNA (single stranded), the EcoRI fragments were reinserted into pGEM7Zf(+)-SFV (step C) and then clbned back as XbaI-NsA fragments into pSP6-SFV4 (step D). To delete the major part of the cDNA region coding for the structural proteins of SFV, these plasmids were then cut with AsuII (7783) and NdeI (11033), blunted using Klenow fragment in the presence of all four nucleotides, and religated to create the final vectors designated pSFV1, pSFV2 and pSFV3, respectively (step E). The vectors retain the promoter region of the 26S subgenomic RNA and the last 49 amino acids of the E1 protein as well as the complete noncoding 3' end of the SFV genome.

Figure 8:
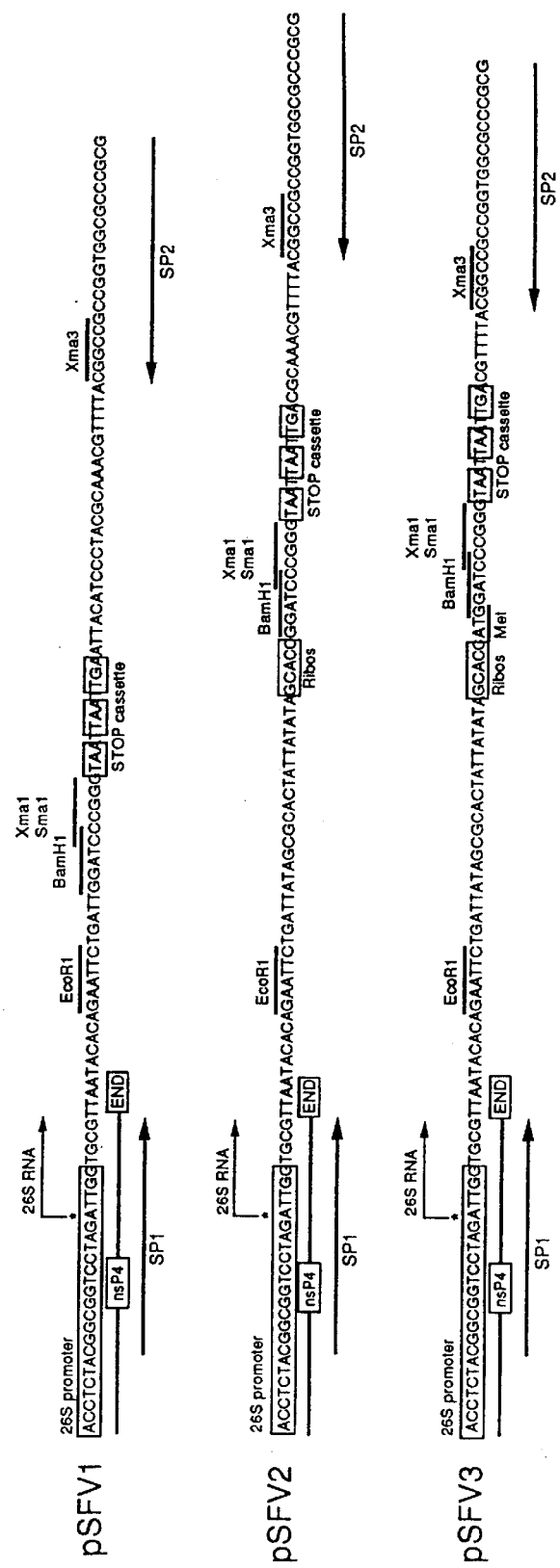
FIG. 8 shows the polylinker region of SFV vector plasmids pSFV1–3; (SEQ ID NO:4,5 and 6) the position of the promoter for the subgenomic 26S RNA is boxed, and the first nucleotide to be transcribed is indicated by an asterisk.

In the vectors the subgenomic (26S) protein coding portion has been replaced with a polylinker sequence allowing the insertional cloning of foreign cDNA sequences under the 26S promoter. As is shown in FIG. 8 these three vectors have the same basic cassette inserted downstream from the 26S promoter, i.e. a poly-linker (BamHI-SmaI-XmaI) followed by a translational stop-codon in all three reading frames. The vectors differ as to the position where the polylinker cassette has been inserted. In pSFV1 the cassette is situated 31 bases downstream of the 26S transcription initiation site. The initiation motif of the capsid gene translation is identical to the consensus sequence (58).

Therefore, this motif has been provided for in pSFV2, where it is placed immediately after the motif of the capsid gene. Finally, pSFV3 has the cassette placed immediately after the initiation codon (AUG) of the capsid gene. Sequencing primers (SP) needed for checking both ends of an insert have been designed to hybridize either to the 26S promoter region (SP1), or to the region following the stop codon cassette (SP2).

Note that the 26S promoter overlaps with the 3'-end of the nsP4 coding region. For pSFV2, the cloning site is positioned immediately after the translation initiation site of the SFV capsid gene. For pSFV3, the cloning site is positioned three nucleotides further downstream, i.e. immediately following to the initial AUG codon of the SFV capsid gene. The three translation stop codons following the polylinker are boxed. The downstream sequencing primer (SP1) overlaps with the 26S promoter, and the upstream sequencing primer (Sp2) overlaps the XmaIII site.

EXAMPLE 3

In this example an in vivo packaging system encompassing helper virus vector constructs is prepared.

Figure 9:
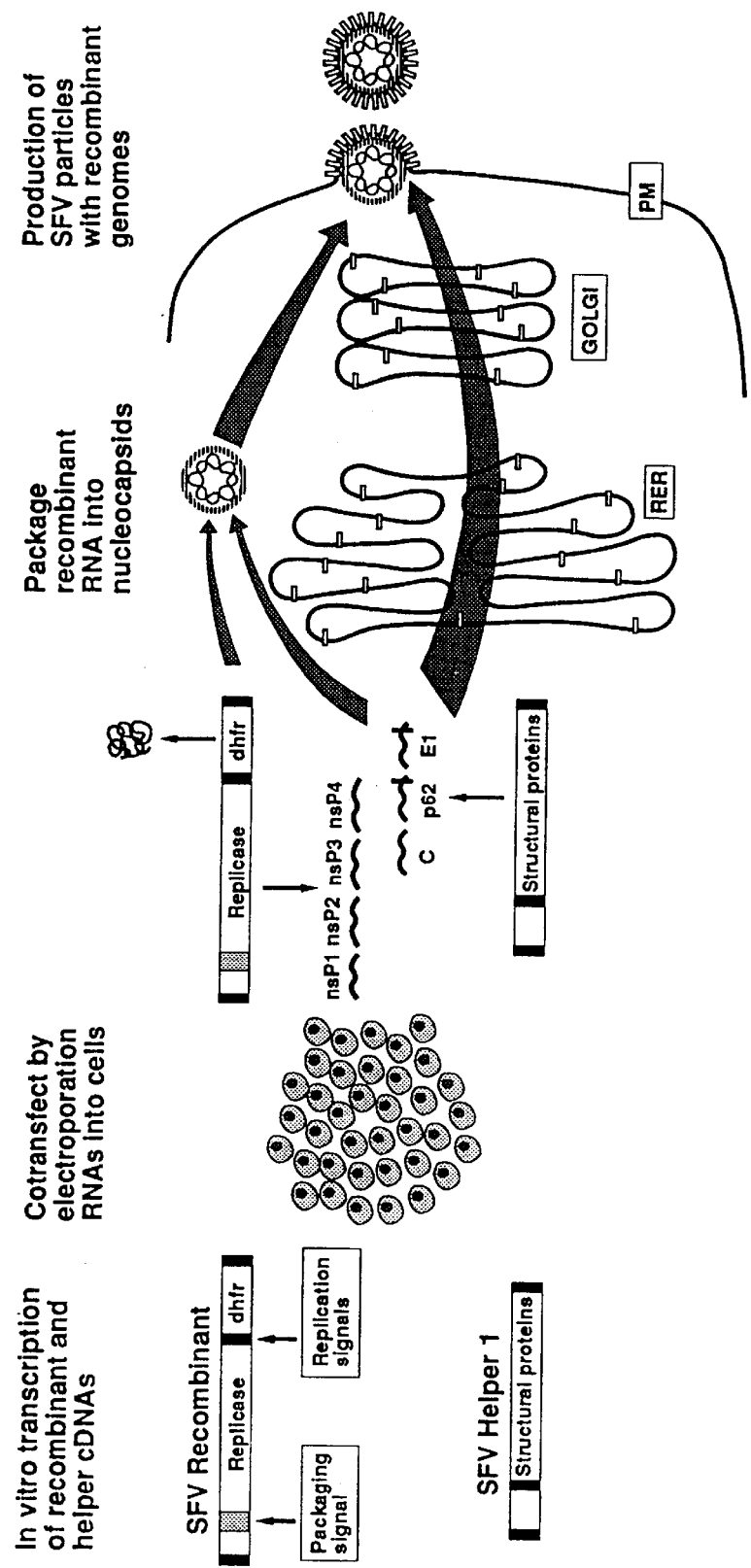
FIG. 9 is a schematic presentation of in vivo packaging of pSFV1-dhfr RNA into infectious particles using helper trans complementation; (dhfr means di-hydrofolate reductase)

The system allows SFV variants defective in structural protein functions, or recombinant RNAs derived from the expression vector construct obtained in Example 2, to be packaged into infectious virus particles. Thus, this system allows recombinant RNAs to be introduced into cells by normal infection. The helper vector, called pSFV-Helper1, is constructed by deleting the region between the restriction endonuclease sites AccI (308) and AccI (6399) of pSP6-SFV4 obtained in Example 1 by cutting and religation as shown in FIGS. 7B, step F. The vector retains the 5' and 3' signals needed for RNA replication. Since almost the complete nsP region of the Helper vector is deleted, RNA produced from this construct will not replicate in the cell due to the lack of a functional replicase complex. As is shown in FIG. 9, after transcription in vitro of pSFV1-recombinant and helper cDNAs, helper RNA is cotransfected with the pSFV1—recombinant derivative, the helper construct providing the structural proteins needed to assemble new virus particles, and the recombinant providing the nonstructural proteins needed for RNA replication, SFV particles comprising recombinant genomes being produced. The cotransfection is preferably produced by electroporation as is disclosed in Example 6 and preferably BHK cells are used as host cells.

To package the RNA a region at the end of nsP1 is required, an area which has been shown to bind capsid protein (57, 59). Since the Helper lacks this region, RNA derived from this vector will not be packaged and hence, transfections with recombinant and Helper produces only virus particles that carry recombinant-derived RNA. It follows that these viruses cannot be passaged further and thus provide a one-step virus stock. The advantage is that infections with these particles will not produce any viral structural proteins.

EXAMPLE 4

This example illustrates the construction of variants of the full-length SFV cDNA clone from Example 1 that allow insertion of foreign DNA sequences encoding foreign epitopes, and the production of recombinant (chimaeric) virus carrying said foreign epitopes as integral parts of the p62, E2 or E1 spike proteins. To this end, a thorough knowledge of the function, topology and antigenic structure of the E2 and E1 envelope proteins has been of the essence.

Earlier studies on the pathogenicity of alphaviruses have shown that antibodies against E2 are type-specific and have good neutralizing activity while those against E1 generally are group-specific and are nonneutralizing (5). However, not until recently have antigenic sites of the closely related alphaviruses SFV, Sindbis, and Ross River been mapped and correlated to the level of amino acid sequence (60, 61, 62, 63). These studies have shown that the most dominant sites in question are at amino acid positions 216, 234 and 246–251 of the SFV E2 spike protein. Interestingly, these three sites are exactly the same as the ones predicted by computer analysis. In the present example domain 246–251 was used, since this area has a highly conserved structure and hydropathy profile within the group of alpha-viruses. Insertion of a gene encoding a foreign epitope into the 246–251 region of the pSP6-SFV4 p62 protein yields particles with one new epitope on each heterodimer, i.e. 240 copies.

To create a unique restriction endonuclease site that would allow specific insertion of foreign epitopes into the E2 portion of the SFV genome, a BamHI site was inserted by site directed mutagenesis using the oligonucleotide 5'-GATCGGCCTAGGAGCCGAGAGCCC (SEQ ID NO: 24).

EXAMPLE 5

In this example a conditionally lethal variant of SFV is constructed from the SFV cDNA obtained in Example 1, which variant carries a mutation in the p62 protein resulting in a noncleavable from of said protein, with the result that this variant as such cannot infect new host cells, unless first cleaved with exogenously added protease.

Figure 10:
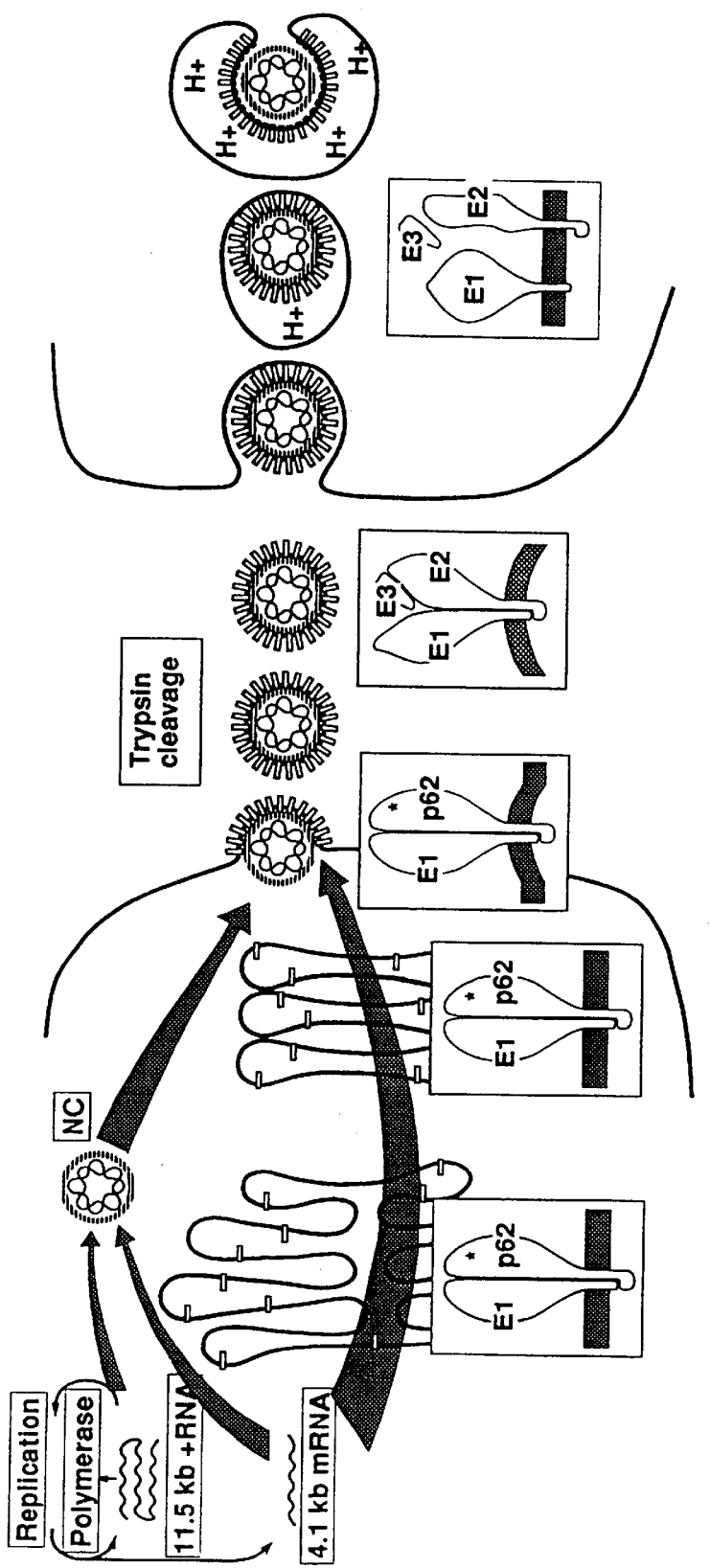
FIG. 10 shows the use of trypsin to convert p62-containing noninfectious virus particles to infectious particles by cleavage of p62 to E2 and E3.

As illustrated in FIG. 10, this construct can be advantageously used as a vaccine carrier for foreign epitopes, since this form of the virus cannot enter new host cells although assembled with wild type efficiency in transfected cells. The block can be overcome by trypsin treatment of inactive virus particles. This converts the particle into a fully entry-competent form which can be used for amplification of this virus variant stock.

Once activated the SFV variant will enter cells normally through the endocytic pathway and start infection. Viral proteins will be made and budding takes place at the plasma membrane. However, all virus particles produced will be of inactive form and the infection will thus cease after one round of infection. The reason for the block in infection proficiency is a mutation which has been introduced by site directed mutagenesis into the cleavage site of p62. This arginine to leucine substitution (at amino acid postion 66 of the E3 portion of the p62 protein) changes the consensus features of the cleavage site so that it will not be recognized by the host cell proteinase that normally cleaves the p62 protein to the E2 and E3 polypeptides during transport to the cell surface. Instead, only exogenously added trypsin will be able to perform this cleavage, which in this case occurs at the arginine residue 65 immediately preceding the original cleavage site. As this cleavage regulates the activation of the entry function potential of the virus by controlling the binding of the entry spike subunit, the virus particle carrying only uncleaved p62 will be completely unable to enter new host cells.

The creation of the cleavage deficient mutation E2 has been described earlier (29). An AsuII-NsλI fragment spanning this region was then isolated and cloned into the full-length cDNA clonepSP6-SFV4.

EXAMPLE 6

In this example transfection of BHK cells with SFV RNA molecules transcribed in vitro from full-length cDNA from Example 1 or variants thereof or the SFV vectors from Example 2, which comprise exogenous DNA, is disclosed. The transfection is carried out by electroporation which is shown to be very efficient at optimized conditions.

BHK cells were transfected with the above SFV RNA molecules by electroporation and optimal conditions were determined by varying parameters like temperature, voltage, capacitance, and number of pulses. Optimal transfection was obtained by 2 consecutive pulses of 1.5 kV at 25 pF, under which negligible amounts of cells were killed. It was found that it was better to keep the cells at room tempeature than at 0° C. during the whole procedure. Transfection by electroporation was also measured as a function of input RNA. As expected, an increase in transfection frequency was not linearly dependent on RNA concentration, and about 2 $\mu$g of cRNA were needed to obtain 100% transfection.

On comparison with conventional transfection, this is a great improvement. For example, with DEAE-Dextran transfection optimally, only 0.2% of the cells were transfected:

EXAMPLE 7

This example illustrates heterologous gene expression driven by the SFV vector, pSFV1 from Example 2, for genes encoding the 21 kD cytoplasmic mouse dihydrofolate reductase (dhfr), the 90 kD membrane protein human transferrin receptor (TR), and finally the 14 kD secretory protein chicken lysozyme. The dhfr gene was isolated from pGEM2-dhfr (64) as a BamHI-HindIII fragment blunted with Klenow fragment and inserted into SmaI-cut pSFV1. The transferrin receptor gene was first cloned from pGEM1-TR (64, 65) as an XbaI-EcoRI fragment into pGEM7ZF(+) and subsequently from there as a BamHI fragment into pSFV1. Finally, a BamHI fragment from pGEM2 carrying the lysozyme gene (21) was cloned into pSFV1.

To study the expression of the heterologous proteins, in vitro-made RNA of the dhfr and TR constructs was electroporated into BHK cells. RNA of wild type SFV was used as control. At different time points post electroporation (p.e.) cells were pulse-labeled for 10 min followed by a 10 min chase, whereafter the lysates were analyzed by gel electrophoresis and autoradiography. The results are shown in FIGS. 11A–11E. More specifically, BHK cells were transfected with RNAs of wild type SFV, pSFV1-dhfr, and pSFV1-TR, pulse-labeled at 3, 6, 9, 12, 15 and 24 h p.e. Equal amounts of lysate were run on a 12% gel. The 9 h sample was also used in immunoprecipitation (IP) of the SFV, the dhfr and the transferrin receptor proteins. Cells transfected with pSFV1-lysozyme were pulse-labeled at 9 h p.e. and then chased for the times (hours) indicated. An equal portion of lysate or medium was loaded on the 13;5% gel. IP represents immunoprecipitation from the 1 h chase lysate sample. The U-lane is lysate of labeled but untransfected cells. At 3 h p.e. hardly any exogenous proteins were made, since the incoming RNA starts with minus strand synthesis which does not peak until about 4–5 h p.e. (5). At this time point, almost all labeled proteins were of host origin. In contrast, at 6 h p.e. the exogenous proteins were synthesized with great efficiency, and severe inhibition of host protein synthesis was evident. This was even more striking at 9 h p.e., when maximum shut down of host protein synthesis had been reached. Efficient production of the heteroloqous proteins continued up to 24 h p.e., after which production slowed down (data not shown), indicating that the cells had entered a stationary phase.

Figures 11A, 11B, 11C:
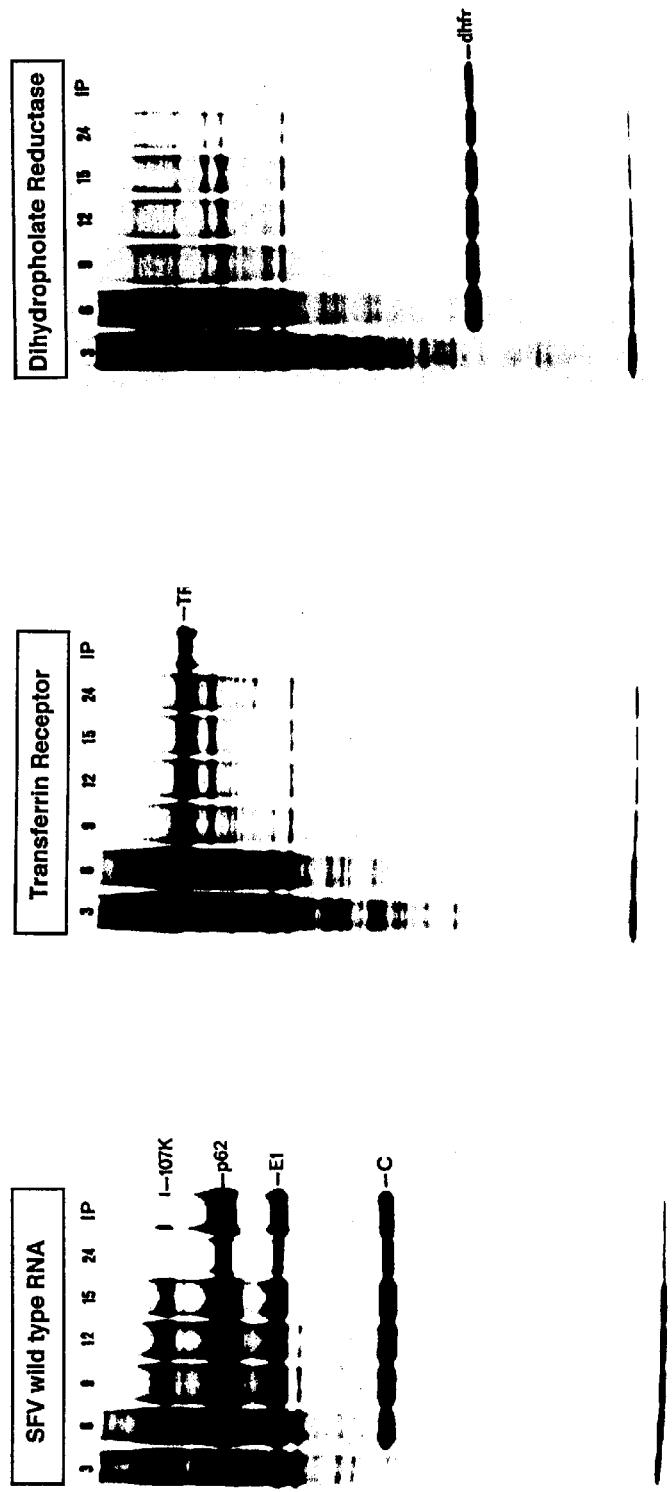
FIGS. 11A–11E show the expression of heterologous proteins in BHK cells upon RNA transfection by electroporation.
Figure 11E:
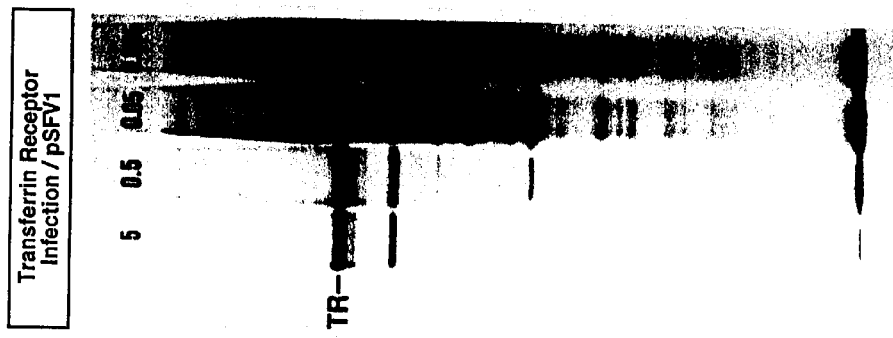
Figure 11D:
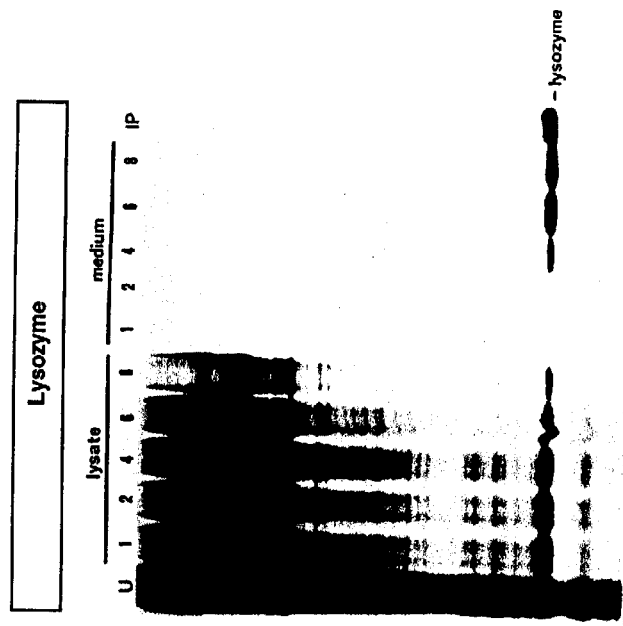

Since chicken lysozyme is a secretory protein, its expression was analyzed both from cell lysates and from the growth medium. Cells were pulse-labeled at 9 h p.e. and then chased up to 8 h. The results are shown in FIG. 11D. Although lysozyme was slowly secreted, almost all labeled material was secreted to the medium during the chase.

EXAMPLE 8

This example illustrates the present in vivo packaging system.

In vitro-made RNA of pSFV1-TR was mixed with Helper RNA at different ratios and these mixtures were cotransfected into BHK cells. Cells were grown for 24 h after which the culture medium was collected and the virus particles pelleted by ultracentrifugation. The number of infectious units (i.u.) was determined by immunofluorescence. It was found that a 1:1 ratio of Helper and recombinant most efficiently produced infectious particles, and on the average $5 \times 10^6$ cells yielded $2.5 \times 10^9$ i.u. The infectivity of the virus stock was tested by infecting BHK cells at different multiplicities of infection (m.o.i.). In FIG. 11 the results for expression of human transferrin receptor in BHK cells after infection by such in vivo packaged particles carrying pSFV1-TR recombinant RNA is shown to the lower right. 200 $\mu$l of virus diluted in MEM (including 0,5% BAS and 2 mM glutamine) was overlaid on cells to give m.o.i. values ranging from 5 to 0.005. After 1 h at 37° C., complete BHK medium was added and growth continued for 9 h, at which time a 10 min pulse (100 $\mu$Ci $^{35}$S-methionine/ml) and 10 min chase was performed, and the cells dissolved in lysis buffer. 10 $\mu$l out of the 300 $\mu$l lysate (corresponding to 30,000 cells) was run on the 10% gel, and the dried gel was exposed for 2 h at −70° C. Due to the high expression level, only 3,000 cells are needed to obtain a distinct band on the autoradiograph with an overnight exposure.

Thus, it was found that efficient protein production and concomitant host protein shut-off occurred at about 1 i.u. per cell. Since one SFV infected cell produces on the average $10^8$ capsid protein molecules, it follows that a virus stock produced from a single electroporation can be used to produce $10^{17}$ protein molecules equaling about 50 mg of protein.

From the foregoing experimental results it is obvious that the present invention is related to very useful and efficient expression system which lacks several of the disadvantages of the hitherto existing expression system. The major advantages of the present system are shortly summarized as follows:

(1) High titre recombinant virus stocks can be produced in one day by one transfection experiment. There is no need for selection/screening, plaque purification and amplification steps. This is appreciated since an easy production of recombinant virus is especially important in experiments where the phenotypes of large series of mutants have to be characterized.

(2) The recombinant virus stock is free from helper virus since only the recombinant genome but not the helper genome contains a packaging signal.

(3) The recombinant virus can be used to infect the recombinant genome in a "natural" and non-leakes way into a large variety of cells including insect and most higher euoaryotic cell types. Such a wide host range is very useful for an expressions system especially when cell-type-specific posttranslational modification reactions are required for the activity of the expressed protein.

(4) The level of protein expression obtained is extremely high, the level corresponding to those of the viral proteins during infection. There is also a host cell protein shut-off which makes it possible to follow the foreign proteins clearly in cell lysates without the need for antibody mediated antigen concentration. This will facilitate DNA expression experiments in cell biology considerably. Furthermore, problems of interference by the endogenous counter part to an expressed protein (i.e. homo-oligomerization reactions) can be avoided.

EXAMPLE 9

This example illustrates epitope carriers.

A very important example where vaccine development is of the utmost importance concerns the acquired immunodeficiency syndrome (AIDS) caused by the human immunodeficiency virus HIV-1 (66, 67). So far, all attempts to produce an efficient vaccine against HIV-1 have failed, although there was a very recent report that vaccination with disrupted SIV-1 (Simian immunodeficiency virus) to a certain extent may give protection against infections of that virus (68). However, development of safe and effective vaccine against HIV-1 will be very difficult due to the biological properties of the virus. In the present example one epitope of HIV-1 was inserted into an antigenic domain of the E2 protein of SFV. The epitope used is located in glycoprotein gp120 of HIV-1, spanning amino acids 309–325. This forms the variable loop of HIV-1 and is situated immediately after an N-glycosylated site.

Figure 12B:
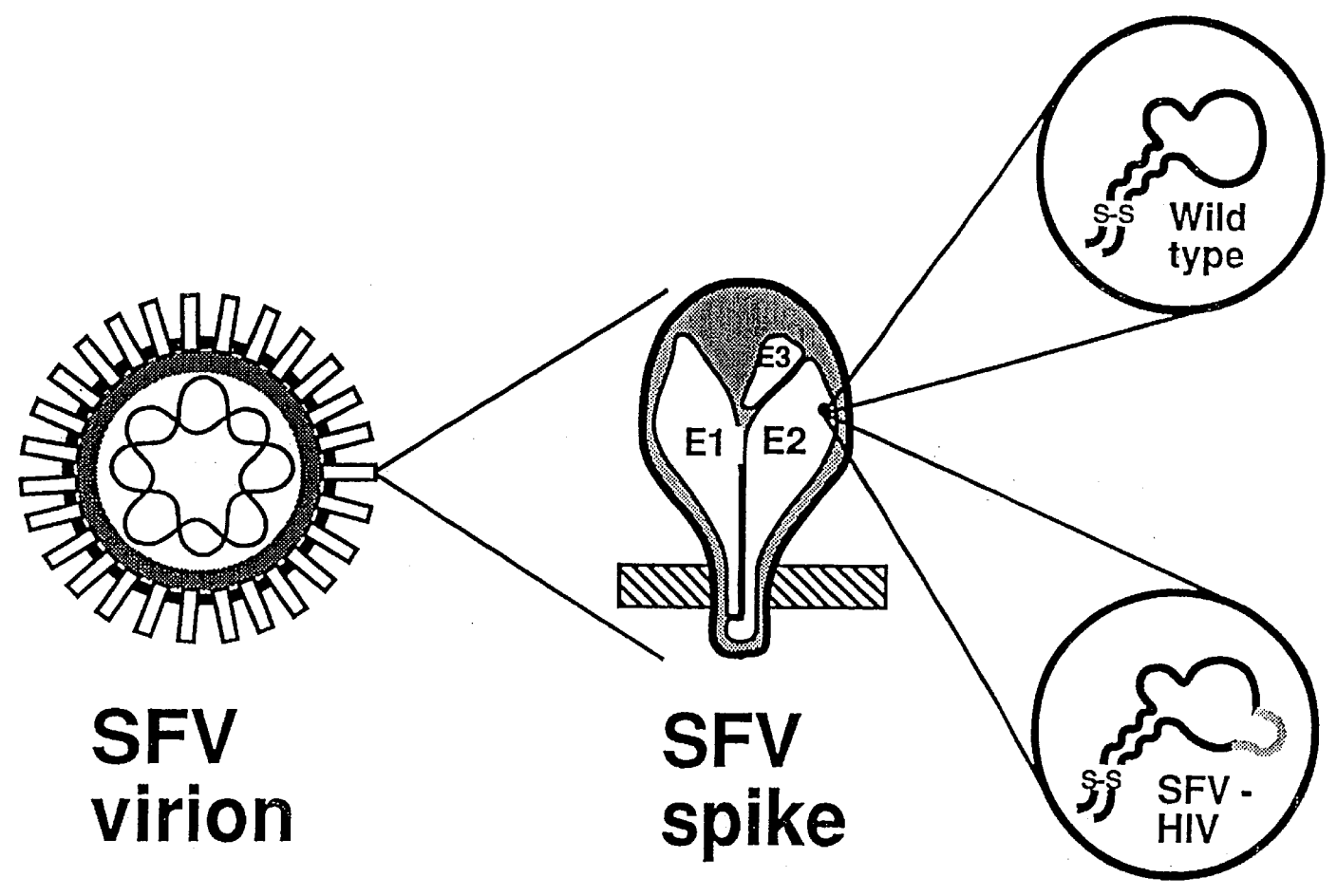

A chimaera was constructed where the 309–325 epitope of HIV was inserted into the BamHI site using cassette insertion of ready-made oligonucleotides encoding the HIV epitope. The required base substitutions at the BamHI site did not lead to any amino acid changes in the vector, although two amino acids (Asp and Glu) changed places. This change did not have any deleterious effect since in vitro made vector RNA induced cell infection with wild type efficiency. FIGS. 12A–B show the sequences in the area of interest in the epitope carrier. In preliminary experiments, it has been shown that chimaeric proteins were produced. The proteins can be immunoprecipitated with anti-HIV antibodies. It is to be expected that these are also used for production of chimaeric virus particles that can be used for vaccine preparation against HIV. Such particles are shown in FIGS. 12A–B, lower part.

List of References

1) Bishop, D. H. L. (1990). Gene expression using insect cells and viruses. In current Opinion in Biotechnology, Vol. 1, Rosenberg, M., and Moss, B., eds. (London: Current Opinion Ltd.), pp. 62–67.
2) Moss, B. (1990). Regulation of Vaccinia virus transcription. Ann. Rev. Biochem. 59, 661–688.
3) Moss, B, and Flexner, C. (1989). Vaccinia virus expression vectors. Ann. N.Y. Acad Sci. 569, 86–103.
4) Garoff, H., Kondor-Koch, C., and Riedel, H. (1982). Structure and assembly of alphaviruses. Curr. Top. Microbiol. Immunol. 99, 1–50.
5) Strauss, E. G., and Strauss, J. H. (1986). Structure and replication of the alphavirus genome. In The Togaviridae and Flaviviridae, Vol. Schlesinger, S. S., and Schlesinger, M. J., eds (New york: Plenum Press), pp. 35–90.
6) Garoff, H., Frischauf, A.-M., Simons, K., Lehrach, H, and Delius, H. (1980). Nucleotide sequence of cDNA coding for Semliki Forest virus membrane glycoproteins. Nature 288, 236–241.
7) Takkinen, K. (1986). Complete nucleotide sequence of the nonstructural protein genes of Semliki forest virus. Nucl. Acids Res. 14, 5667–5682.
8) de Groot, R. J., Hardy, W. R., Shirako, Y., and Strauss, J. H. (1990). Cleavage-site preferences of Sindbis virus polyproteins containing the non-structural proteinase. Evidence for temporal regulation of polyprotein processing in vivo. EMBO J. 9, 2631–2638.
9) Hahn, Y. S., Strauss, E. G., and Strauss, J. H. (1989b). Mapping of RNA-temperature-sensitive mutants of Sindbis virus: assignment of complementation groups A, B, and G to nonstructural proteins. J. Virol. 63, 3142–3150.
10) Mi, S., Durbin, R., Huang, H. V., Rice, C. M., and Stollar, V. (1989). Association of the Sindbis virus RNA methyltransferase activity with the nonstructural protein nsP1. Virology 170, 385–391.
11) Ding, M., and Schlesinger, M. J. (1989). Evidence that Sindbis virus nsP2 is an autoprotease which processes the virus nonstructural polyprotein. Virology 171, 280–284.
12) Hardy, W. R., and Strauss, J. H. (1989). Processing the nonstructural polyproteins of Sindbis virus: nonstructural proteinase is in the C-terminal half of nsP2 and functions both in cis and in trans. J.Virol. 63, 4653–4664.
13) Li, G., La Starza, M. W., Hardy, W. R., Strauss, J. H., and Rice, C. M. (1990). Phosphorylation of Sindbis virus nsP3 in vivo and in vitro.
14) Peränen, J., Takkinen, K., Kalkkinen, N., and Kääriäinen, L. (1988). Semliki Forest virus-specific non-structural protein nsP3 is a phosphoprotein. J. Gen. Virol. 69, 2165–2178.
15) Hahn, Y. S., Grakoui, A., Rice, C. M., Strauss, E. G., and Strauss, J. H. (1989a). Mapping of RNA-temperature-sensitive mutants of Sindbis virus: complementation group F mutants have lesions in nsP4.
16) Sawicki, D. L., Barkhimer, D. B. Sawicki, S. G., Rice, C. M., and Schlesinger, S. (1990). Temperature sensitive shut-off of alphavirus minus strand RNA synthesis maps to a nonstructural protein, nsP4. Virology 174, 43–52.
17) Grakoui, A., Levis, R., Raju, R., Huang, H. V., and Rice, C. M. (1989). A cis-acting mutation in the Sindbis virus junction region which affects subgenomic RNA synthesis. J. Virol. 63, 5216–5227.
18) Levis, R., Schlesinger, S., and Huang, H. V. (1990). Promoter for Sindbis virus RNA-dependent subgenomic RNA transcription. J. Virol. 64, 1726–1733.
19) Schlesinger, S. S., and Schlesinger, M. J. (1986). Formation and assmebly of alphavirus glycoproteins. In The Togaviridae and Flaviviridae, Vol. Schlesinger, S. S., and Schlesinger, M. J., eds. (New York: Plenum Press), pp. 121–148.
20) Hahn, C. S., and Strauss, J. H. (1990). Site-directed mutagenesis of the proposed catalytic amino acids of the Sindbis virus capsid protein autoprotease. J. Virol. 64, 3069–3073.
21) Melancon, P., and Garoff, H. (1987). Processing of the Semliki Forest virus structural polyprotein; Role of the capsid protease. J. Virol. 61, 1301–1309.
22) Bonatti, S., Migliaccio, G., Blobel, G., and Walter, P (1984). Role of the signal recognition particle in the membrane assembly of Sindbis viral gycoprotein. Eur. J. Biochem. 140, 499–502.
23) Garoff, H., Simons, K., and Dobberstein, B. (1978). Assembly of Semliki Forest virus membrane glycoproteins in the membrane of the endoplasmic reticulum in vitro. J. Mol. Biol. 124, 587–600.
24) Garoff, H., Huylebroeck, D., Robinson, A., Tillman, U., and Liljeström, P. (1990). The signal sequence of the p62 protein of Semliki Forest virus is involved in initiation but not in completing chain translocation. J. Cell Biol. 111, 867–876.

25) Melanqon, P., and Garoff, H. (1986). Reinitiation of translocation in the Semliki Forest virus structural polyprotein: Identification of the signal for the E1 glycoprotein. EMBO J. 5, 1551–1560.

26) Lobigs, M., Zhao, H., and Garoff, H. (1990b). Function of Semliki Forest virus E3 peptide in virus assembly: Replacement of E3 with an artificial signal peptide abolishes spike heterodimerization and surface expression of E1. J. Virol. 64, 4346–4355.

27) de Curtis, I., and Simons, K. (1988). Dissection of Semliki Forest virus glycoprotein delivery from the trans-Golgi network to the cell surface in permeabilized BHK cells. Proc. Natl. Acad. Sci. USA, 85, 8052–8056.

28) Helenius, A., Kielian, M., Mellman, I., and Schmid, S. (1989). Entry of enveloped viruses into their host cells. In Cell Biology of Virus Entry, Replication, and Pathogenesis, Vol. 90, Compans, R. W., Helenius, A., and Oldstone, M.B.A., eds. (New York: Alan R. Liss, Inc.), pp. 145–161.

29) Lobigs, M., and Garoff, H. (1990). Fusion function of the Semliki Forest virus spike is activated by proteolytic cleavage of the envelope glycoprotein p62. J. Virol. 64, 1233–1240.

30) Lobigs, M., Wahlberg, J. M., and Garoff, H. (1990a). Spike protein oligomerization control of Semliki Forest virus fusion. J. Virol. 64, 5214–5218.

31) Wahlberg, J. M., Boere, W. A., and Garoff, H. (1989). The heterodimeric association between the membrane proteins of Semliki Forest virus changes its sensitivity to mildly acidic pH during virus maturation. J. Virol. 63, 4991–4997.

32) Ziemiecki, A., Garoff, H., and Simons, K. (1980). Formation of the Semliki Forest virus membrane glycoprotein complexes in the infected cell. J. Gen. Virol. 50, 111–123.

33) Fuller, S. D. (1987). The T=4 envelope of Sindbis virus is organized by interactions with a complementary T=3 capsid. Cell 48, 923–934.

34) Wengler, G. (1980). Effects of alphaviruses on host cell macromolecular synthesis. In The Togaviruses, Vol. Schlesinger, R. W., eds. (New York: Academic Press, Inc.), pp. 459–472.

35) Stollar, V. (1980). Defective interfering alphaviruses. In The Togaviruses, Vol. Schlesinger, R. W., eds. (New York: Academic Press), pp. 427–457.

36) Boere, W. A. M., Harmsen, T., Vinje, J., Benaissa-Trouw, B. J., Kraaijeeveld, C. A., and Snippe. H. (1984). Identification of distinct antigenic determinants on Semliki Forest virus by using monoclonal antibodies with different antiviral activities. J. Virol. 52, 575–582.

37) Greiser-Wilke, I., Moennig, V., Kaaden, O.-R., and Figueiredo, L. T. M. (1989). Most alphaviruses share a conserved epitopic region on their nucleocapsid protein. J. Gen. Virol. 70, 743–748.

38) Kondor, K. C., Bravo, R., Fuller, S. D., Cutler, D., and Garoff, H. (1985). Exocytotic pathways exist to both the apical and the basolateral cell surface of the polarized epithelial cell MDCK. Cell 43, 297–306.

39) Sambrook, J., Fritsch, E. F., and Maniatis, T. (1989). Molecular Cloning. A Laboratory Manual. (Cold Spring Harbor: Cold spring Harbor Laboratory Press).

40) Benson, S. A. (1984). A rapid procedure for isolation of DNA fragments from agarose gels. Bio Techniques 2, 66–68.

41) Silhavy, T. J., Berman, M. L., and Enquist, L. W. (1984). Experiments with Gene Fusions. (New York: Cold Spring Harbor Laboratory Press).

42) Yanisch-Perron, C., Vieira, J., and Messing, J. (1985). Improved M13 phage cloning vectors and host strains: nucleotide sequences of the M13mp18 and pUC19 vectors. Gene 33, 103–119.

43) Chung, C. T., and Miller, R. T. (1988). A rapid and convenient method for the preparation and storage of competent bacterial cells. Nucl. Acids Res. 16, 3580.

44) Kunkel, T. A., Roberts, J. D., and Zakour, R. A. (1987). Rapid and efficient site-specific mutagenesis without phenotypic selection. Meth. Enzymol. 154, 367–382.

45) Su, T.-Z., and El-Gewely, M. R. (1988). A multisite-directed mutagenesis using T7 DNA polymerase: application for reconstructing a mammalian gene. Gen 69, 81–89.

46) Krieg, P. A., and Melton, D. A. (1987). In vitro RNA synthesis with SP6 RNA polymerase. Meth. Enzymol. 155, 397–415.

47) Rice, C. M., Levis, R., Strauss, J. H., and Huang, H. V. (1987). Production of infectious RNA transcripts from Sindbis virus cDNA clones: Mapping of lethal mutations, rescue of a temperature-sensitive marker, and in vitro mutagenesis to generate defined mutants. J. Virol. 61, 3809–3819.

48) Cutler, D. F., and Garoff, H. (1986). Mutants of the membrane-binding region of Semliki,Forest virus E2 protein. I. Cell surface transport and fusogenic activity. J. Cell Biol. 102, 889–901.

49) Chamberlain, J. P. (1979). Fluorographic detection of radioactivity in polyacrylamide gels with watersoluble fluor, sodium salicylate. Anal. Biochem. 98, 132–135.

50) Gubler, U., and Hoffman, B. J. (1983). A simple and very efficient method for generating cDNA libraries. Gene 25, 263–269.

51) Haymerle, H., Herz, J., Bressan, G. M., Frank, R., and Stanley, K. K. (1986). Efficient construction of cDNA libraries in plasmid expression vectors using an adaptor strategy. Nucl. Acids Res. 14, 8615–8124.

52) Davis, N. L., Willis, L. V., Smith, J. F., and Johnston, R. E. (1989). In vitro synthesis of infectious Venezuelan Equine Encephalitis virus RNA from a cDNA clone: Analysis of a viable deletion mutant. Virology 171, 189–204.

53) Niesters, H. G., and Strauss, J. H. (1990a). Defined mutations in the 5' nontranslated sequence of Sindbis virus RNA. J. Virol. 64, 4162–4168.

54) Niesters, H. G. M., and Strauss, J. H. (1990b). Mutagenesis of the conserved 51-nucleotide region of Sindbis virus. J. Virol. 64, 1639–1647.

55) Tsiang, M., Weiss, B. G., and Schlesinger, S. (1988). Effects of 5'-terminal modifications on the biological activity of defective interfering RNAs of Sindbis virus. J. Virol. 62, 47–53.

56) Kuhn, R. J., Hong, Z., and Strauss, J. H. (1990). Mutagenesis of the 3' nontranslated region of Sindbis virus RNA. J. Virol. 64, 1465–1476.

57) Levis, R., Weiss, B. G., Tsiang, M., Huang, H., and Schlesinger, S. (1986). Deletion mapping of Sifidbis virus DI RNAs derived from cDNAs defines the sequences essential for replication and packaging. Cell 44, 137–145.

58) Kozak, M. (1989). The scanning model for translation: an update. J. Cell Biol. 108, 229–241.

59) Weiss, B., Nitschko, H., Ghattas, I., Wright, R., and Schlesinger, S. (1989). Evidence for specificity in the encapsidation of Sindbis virus RNAs. J. Virol. 63, 5310–5318.

60) Davis N L, Pence D F, Meyer W J, Schmaljohn A L and Johston R E (1987). Alternative forms of a strain-specific neutralizing antigenic site on the Sindbis virus E2 glycoprotein. Virology 161:101–108.
61) Mendoza Q P, Stanley J and Griffin D E (1988). Monoclonal antibodies to the E1 and E2 glycoproteins of Sindbis virus: Definition of epitopes and efficiency of protection from fatal encephalitis. J. Gen. Virol. 70:3015–3022.
62) Vrati S, Fernon C A, Dalgarno L and Weir R C (1988). Location of a major antigenic site involved in Ross River virus neutralization. Virology 162:346–353.
63) Grosfeld H, Velan B, Leitner M. Cohen S, Lustig S, Lachmi B and Shafferman A (1989). Semliki Forest virus E2 envelope epitopes induce a nonneutralizing humoral response which protects mice against lethal challenge. J. Virol. 63:3416–3422.
64) Zerial, M., Melancon, P., Schneider, C., and Garoff, H. (1986). The transmembrane segment of the human transferrin receptor functions as a signal peptide. EMBO J. 5, 1543–1550.
65) Schneider, C., Owen, M. J., Banville, D., and Williams, J. G. (1984). Primary structure of human transferrin receptor deduced from the mRNA sequence. Nature 311, 675–678.
66) Ratner L, Haseltine W, Patarca R, Livak K J, Starcich B, Josephs S F, Doran E R, Rafalki J A, Whitehorn E A, Baumeister K, Ivanoff L, Petteway S R, Pearson M L, Lautenberger J A, Papas T S, Ghrayeb J, Chang N T, Gallo R C and Wong-Staal F (1985). Complete nucleotide sequence of the AIDS virus, HTLVIII. Nature 313:277–284.
67) AIDS (1988). Sci.Am. 259. A single-topic issue on HIV biology.
68) Desrosiers R C, Wyand M S, Kodama T, Ringler D J, Arthur L O, Sehgal P K, Letvin N L, King N W and Daniel M D (1989). Vaccine protection against simian immunodeficiency virus infection.
69) Ginsberg H, Brown F, Lerner R A and Chanoch R M (1988). Vaccines 1988. New chemical and genetic approaches to vaccination, Cold Spring Harbor Laboratory, 396 pp.
70) Burke K L, Dunn G, Ferguson M, Minor P D and Almond J W (1988). Antigen chimeras of poliovirus as potential new vaccines. Nature 332:81–82.
71) Colbere-Garapin F, Christodoulou C, Crainic R, Garapin A-C and Candrea A (1988). Addition of a foeeign oligopeptide to the major capsid protein of poliovirus. Proc. Natl. Acad. Sci. USA 85:8668–8672.
72) Evans D J, McKeating J, Meredith J M, Burke K L, Katrak K, John A, Ferguson M, Minor P D, Weiss R A and Almond J W (1989). An engineered poliovirus chimaera elicits broadly reactive HIV-1 neutralizing antibodies. Nature 339:385–388.

What is claimed is:

1. A vaccine comprising a recombinant alphavirus particle comprising an alphavirus structural protein that comprises an amino acid sequence that is exogenous to the alphavirus and that is an antigenic epitope or determinant of a pathogen.

2. The vaccine of claim 1, wherein the alphavirus is Semliki Forest Virus.

3. The vaccine of claim 1, wherein the exogenous amino acid sequence is inserted into the structural protein homologous in function to the p62 protein of Semliki Forest Virus.

4. A method for immunizing a host against a pathogen expressing an antigen exogenous to an alphavirus comprising administering to said host a vaccine according to claim 1 comprising an alphavirus structural protein in turn comprising an antigenic epitope or determinant of said antigen expressed by the pathogen.

5. A vaccine comprising a recombinant alphavirus genome encoding an amino acid sequence exogenous to the wild-type of said alphavirus, wherein said exogenous amino acid sequence comprises an antigenic epitope or determinant inserted into the structural protein homologous in function to the p62 spike protein of Semliki Forest Virus.

6. A vaccine comprising a recombinant RNA molecule which can be efficiently translated and replicated in an animal host cell, comprising an alphavirus RNA genome and an exogenous RNA sequence, wherein said alphavirus RNA genome contains at least one deletion or stop codon mutation such that at least one structural protein of the alphavirus cannot be made upon introduction of said recombinant RNA into said host cell, and further wherein said exogenous RNA sequence is operatively inserted into a region of the alphavirus RNA genome which is non-essential to replication of the recombinant RNA molecule such that the exogenous RNA is expressed from an alphavirus transcriptional promoter when the recombinant RNA is introduced into a host cell and further such that the exogenous RNA expresses its function in said host cell.

7. The vaccine of claim 6, wherein the recombinant RNA is contained in a particle comprising an alphavirus nucleocapsid and a surrounding membrane, wherein the membrane includes an alphavirus spike protein.

8. The vaccine of claim 6, wherein said exogenous amino acid sequence comprises an antigenic epitope or determinant and the nucleic acid encoding said exogenous amino acid sequence is inserted into the part of the alphavirus genome encoding an alphavirus envelope protein.

9. The vaccine of claim 6, wherein the alphavirus is Semliki Forest Virus.

10. The vaccine of claim 6, wherein the nucleic acid encoding the exogenous amino acid sequence is inserted into the portion of the alphavirus genome encoding the structural protein homologous in function to the p62 protein of Semliki Forest Virus.

11. A method for immunizing a subject comprising administering to said subject a chimeric alphavirus particle wherein said recombinant alphavirus particle comprises a chimeric alphavirus envelope protein comprising an immunogenic exogenous amino acid sequence inserted into the amino acid sequence of an envelope protein of said alphavirus.

12. A method for immunizing a subject comprising administering to said subject a composition comprising a recombinant RNA molecule which comprises (a) an alphavirus RNA genome that contains at least one deletion or stop codon mutation such that at least one structural protein of the alphavirus cannot be made upon introduction of said recombinant RNA molecule into a cell of said subject, and (b) an exogenous RNA sequence that encodes a polypeptide that is an antigenic epitope or determinant of a pathogen, wherein said exogenous RNA sequence is operatively inserted into a region of the alphavirus RNA genome which is non-essential to replication of the recombinant RNA molecule such that the exogenous RNA is expressed from an alphavirus transcriptional promoter when the recombinant RNA molecule is introduced into a cell of said subject and further such that the exogenous RNA expresses its function in said cell of said subject thereby introducing said recombinant RNA molecule into a cell of said subject and eliciting an immune response in said subject.

13. The method of claim 12, wherein said recombinant alphavirus expresses a chimeric alphavirus envelope protein, said chimeric alphavirus envelope protein comprising an immunogenic exogenous amino acid sequence inserted into the amino acid sequence of an envelope protein of said alphavirus.

14. The method of claim 12, wherein said recombinant RNA molecule comprises an exogenous RNA sequence encoding a polypeptide that will elicit an immune response in the subject when expressed in cells of the subject and wherein said recombinant RNA molecule is contained in a particle comprising an alphavirus nucleocapsid and a surrounding membrane.

15. A method for immunizing a subject which comprises administering to said subject a composition comprising:

a recombinant DNA, which comprises (a) a nucleotide sequence encoding an alphavirus RNA genome that contains at least one deletion or stop codon mutation such that at least one structural protein of the alphavirus cannot be made upon introduction of said recombinant DNA into a cell of said subject, and (b) an exogenous DNA sequence that encodes a polypeptide that is an antigenic epitope or determinant of a pathogen, wherein said exogenous DNA sequence is operatively inserted into a region of the DNA encoding the alphavirus RNA genome which is non-essential to replication of the alphavirus RNA genome such that the exogenous DNA is expressed from an alphavirus transcriptional promoter when the recombinant DNA is introduced into a cell of said subject and further such that the exogenous DNA expresses its function in said cell of said subject; thereby introducing said recombinant DNA into a cell of said subject and eliciting an immune response in said subject.

16. A method for immunizing a subject, comprising administering to said subject a composition comprising a recombinant RNA contained in a particle comprising an alphavirus nucleocapsid and a surrounding membrane, wherein the membrane includes an alphavirus spike protein, wherein the recombinant RNA is a recombinant RNA molecule which can be efficiently translated and replicated in an animal host cell, comprising an alphavirus RNA genome and an exogenous RNA sequence, wherein said alphavirus RNA genome contains at least one deletion or stop codon mutation such that at least one structural protein of the alphavirus cannot be made upon introduction of said recombinant RNA into said host cell, and further wherein said exogenous RNA sequence is operatively inserted into a region of the alphavirus RNA genome which is non-essential to replication of the recombinant RNA molecule such that the exogenous RNA is expressed from an alphavirus transcriptional promoter when the recombinant RNA is introduced into a host cell and further such that the exogenous RNA expresses its function in said host cell, wherein said exogenous RNA sequence encodes a polypeptide that will elicit an immune response in the subject when expressed in cells of the subject.

17. A vaccine comprising a recombinant alphavirus genome encoding an amino acid sequence exogenous to the wild-type of said alphavirus, wherein said exogenous amino acid sequence comprises an antigenic epitope or determinant and is inserted into the part of the alphavirus genome encoding an alphavirus envelope protein.

* * * * *

```
                          SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
         (A) LENGTH: 11517 base pairs
         (B) TYPE: nucleic acid
         (C) STRANDEDNESS: single
         (D) TOPOLOGY: linear (ii) MOLECULE TYPE: RNA (genomic)

(iii) HYPOTHETICAL: NO (iv) ANTI-SENSE: NO (vi) ORIGINAL SOURCE:
         (A) ORGANISM: Semliki Forest Virus (ix) FEATURE:
         (A) NAME/KEY: -
         (B) LOCATION: 1..11517
         (D) OTHER INFORMATION: /label= genome
             /note= "Semliki Forest Virus complete nucleotide
             sequence, presented as a cloned DNA sequence; see
             Figure 5."

(ix) FEATURE:
         (A) NAME/KEY: CDS
         (B) LOCATION: 87..7379
         (D) OTHER INFORMATION: /product= "SFV polyprotein"

(ix) FEATURE:
         (A) NAME/KEY: CDS
         (B) LOCATION: 7421..11179
         (D) OTHER INFORMATION: /product= "SFV polyprotein"

(xi) SEQUENCE DESCRIPTION: SEQ ID NO: 1:
```

-continued

```
GATGGCGGAT GTGTGACATA CACGACGCCA AAAGATTTTG TTCCAGCTCC TGCCACCTCC      60

GCTACGCGAG AGATTAACCA CCCACG ATG GCC GCC AAA GTG CAT GTT GAT ATT     113
                             Met Ala Ala Lys Val His Val Asp Ile
                              1               5

GAG GCT GAC AGC CCA TTC ATC AAG TCT TTG CAG AAG GCA TTT CCG TCG      161
Glu Ala Asp Ser Pro Phe Ile Lys Ser Leu Gln Lys Ala Phe Pro Ser
 10              15                  20                  25

TTC GAG GTG GAG TCA TTG CAG GTC ACA CCA AAT GAC CAT GCA AAT GCC      209
Phe Glu Val Glu Ser Leu Gln Val Thr Pro Asn Asp His Ala Asn Ala
                 30                  35                  40

AGA GCA TTT TCG CAC CTG GCT ACC AAA TTG ATC GAG CAG GAG ACT GAC      257
Arg Ala Phe Ser His Leu Ala Thr Lys Leu Ile Glu Gln Glu Thr Asp
             45                  50                  55

AAA GAC ACA CTC ATC TTG GAT ATC GGC AGT GCG CCT TCC AGG AGA ATG      305
Lys Asp Thr Leu Ile Leu Asp Ile Gly Ser Ala Pro Ser Arg Arg Met
         60                  65                  70

ATG TCT ACG CAC AAA TAC CAC TGC GTA TGC CCT ATG CGC AGC GCA GAA      353
Met Ser Thr His Lys Tyr His Cys Val Cys Pro Met Arg Ser Ala Glu
     75                  80                  85

GAC CCC GAA AGG CTC GAT AGC TAC GCA AAG AAA CTG GCA GCG GCC TCC      401
Asp Pro Glu Arg Leu Asp Ser Tyr Ala Lys Lys Leu Ala Ala Ala Ser
 90                  95                 100                 105

GGG AAG GTG CTG GAT AGA GAG ATC GCA GGA AAA ATC ACC GAC CTG CAG      449
Gly Lys Val Leu Asp Arg Glu Ile Ala Gly Lys Ile Thr Asp Leu Gln
                110                 115                 120

ACC GTC ATG GCT ACG CCA GAC GCT GAA TCT CCT ACC TTT TGC CTG CAT      497
Thr Val Met Ala Thr Pro Asp Ala Glu Ser Pro Thr Phe Cys Leu His
            125                 130                 135

ACA GAC GTC ACG TGT CGT ACG GCA GCC GAA GTG GCC GTA TAC CAG GAC      545
Thr Asp Val Thr Cys Arg Thr Ala Ala Glu Val Ala Val Tyr Gln Asp
        140                 145                 150

GTG TAT GCT GTA CAT GCA CCA ACA TCG CTG TAC CAT CAG GCG ATG AAA      593
Val Tyr Ala Val His Ala Pro Thr Ser Leu Tyr His Gln Ala Met Lys
    155                 160                 165

GGT GTC AGA ACG GCG TAT TGG ATT GGG TTT GAC ACC ACC CCG TTT ATG      641
Gly Val Arg Thr Ala Tyr Trp Ile Gly Phe Asp Thr Thr Pro Phe Met
170                 175                 180                 185

TTT GAC GCG CTA GCA GGC GCG TAT CCA ACC TAC GCC ACA AAC TGG GCC      689
Phe Asp Ala Leu Ala Gly Ala Tyr Pro Thr Tyr Ala Thr Asn Trp Ala
                190                 195                 200

GAC GAG CAG GTG TTA CAG GCC AGG AAC ATA GGA CTG TGT GCA GCA TCC      737
Asp Glu Gln Val Leu Gln Ala Arg Asn Ile Gly Leu Cys Ala Ala Ser
            205                 210                 215

TTG ACT GAG GGA AGA CTC GGC AAA CTG TCC ATT CTC CGC AAG AAG CAA      785
Leu Thr Glu Gly Arg Leu Gly Lys Leu Ser Ile Leu Arg Lys Lys Gln
        220                 225                 230

TTG AAA CCT TGC GAC ACA GTC ATG TTC TCG GTA GGA TCT ACA TTG TAC      833
Leu Lys Pro Cys Asp Thr Val Met Phe Ser Val Gly Ser Thr Leu Tyr
235                 240                 245

ACT GAG AGC AGA AAG CTA CTG AGG AGC TGG CAC TTA CCC TCC GTA TTC      881
Thr Glu Ser Arg Lys Leu Leu Arg Ser Trp His Leu Pro Ser Val Phe
250                 255                 260                 265

CAC CTG AAA GGT AAA CAA TCC TTT ACC TGT AGG TGC GAT ACC ATC GTA      929
His Leu Lys Gly Lys Gln Ser Phe Thr Cys Arg Cys Asp Thr Ile Val
                270                 275                 280

TCA TGT GAA GGG TAC GTA GTT AAG AAA ATC ACT ATG TGC CCC GGC CTG      977
Ser Cys Glu Gly Tyr Val Val Lys Lys Ile Thr Met Cys Pro Gly Leu
            285                 290                 295

TAC GGT AAA ACG GTA GGG TAC GCC GTG ACG TAT CAC GCG GAG GGA TTC     1025
Tyr Gly Lys Thr Val Gly Tyr Ala Val Thr Tyr His Ala Glu Gly Phe
```

```
            Tyr Gly Lys Thr Val Gly Tyr Ala Val Thr Tyr His Ala Glu Gly Phe
                    300                 305                 310

CTA GTG TGC AAG ACC ACA GAC ACT GTC AAA GGA GAA AGA GTC TCA TTC            1073
Leu Val Cys Lys Thr Thr Asp Thr Val Lys Gly Glu Arg Val Ser Phe
        315                 320                 325

CCT GTA TGC ACC TAC GTC CCC TCA ACC ATC TGT GAT CAA ATG ACT GGC            1121
Pro Val Cys Thr Tyr Val Pro Ser Thr Ile Cys Asp Gln Met Thr Gly
330                 335                 340                 345

ATA CTA GCG ACC GAC GTC ACA CCG GAG GAC GCA CAG AAG TTG TTA GTG            1169
Ile Leu Ala Thr Asp Val Thr Pro Glu Asp Ala Gln Lys Leu Leu Val
                350                 355                 360

GGA TTG AAT CAG AGG ATA GTT GTG AAC GGA AGA ACA CAG CGA AAC ACT            1217
Gly Leu Asn Gln Arg Ile Val Val Asn Gly Arg Thr Gln Arg Asn Thr
            365                 370                 375

AAC ACG ATG AAG AAC TAT CTG CTT CCG ATT GTG GCC GTC GCA TTT AGC            1265
Asn Thr Met Lys Asn Tyr Leu Leu Pro Ile Val Ala Val Ala Phe Ser
        380                 385                 390

AAG TGG GCG AGG GAA TAC AAG GCA GAC CTT GAT GAT GAA AAA CCT CTG            1313
Lys Trp Ala Arg Glu Tyr Lys Ala Asp Leu Asp Asp Glu Lys Pro Leu
    395                 400                 405

GGT GTC CGA GAG AGG TCA CTT ACT TGC TGC TGC TTG TGG GCA TTT AAA            1361
Gly Val Arg Glu Arg Ser Leu Thr Cys Cys Cys Leu Trp Ala Phe Lys
410                 415                 420                 425

ACG AGG AAG ATG CAC ACC ATG TAC AAG AAA CCA GAC ACC CAG ACA ATA            1409
Thr Arg Lys Met His Thr Met Tyr Lys Lys Pro Asp Thr Gln Thr Ile
                430                 435                 440

GTG AAG GTG CCT TCA GAG TTT AAC TCG TTC GTC ATC CCG AGC CTA TGG            1457
Val Lys Val Pro Ser Glu Phe Asn Ser Phe Val Ile Pro Ser Leu Trp
            445                 450                 455

TCT ACA GGC CTC GCA ATC CCA GTC AGA TCA CGC ATT AAG ATG CTT TTG            1505
Ser Thr Gly Leu Ala Ile Pro Val Arg Ser Arg Ile Lys Met Leu Leu
        460                 465                 470

GCC AAG AAG ACC AAG CGA GAG TTA ATA CCT GTT CTC GAC GCG TCG TCA            1553
Ala Lys Lys Thr Lys Arg Glu Leu Ile Pro Val Leu Asp Ala Ser Ser
    475                 480                 485

GCC AGG GAT GCT GAA CAA GAG GAG AAG GAG AGG TTG GAG GCC GAG CTG            1601
Ala Arg Asp Ala Glu Gln Glu Glu Lys Glu Arg Leu Glu Ala Glu Leu
490                 495                 500                 505

ACT AGA GAA GCC TTA CCA CCC CTC GTC CCC ATC GCG CCG GCG GAG ACG            1649
Thr Arg Glu Ala Leu Pro Pro Leu Val Pro Ile Ala Pro Ala Glu Thr
                510                 515                 520

GGA GTC GTC GAC GTC GAC GTT GAA GAA CTA GAG TAT CAC GCA GGT GCA            1697
Gly Val Val Asp Val Asp Val Glu Glu Leu Glu Tyr His Ala Gly Ala
            525                 530                 535

GGG GTC GTG GAA ACA CCT CGC AGC GCG TTG AAA GTC ACC GCA CAG CCG            1745
Gly Val Val Glu Thr Pro Arg Ser Ala Leu Lys Val Thr Ala Gln Pro
        540                 545                 550

AAC GAC GTA CTA CTA GGA AAT TAC GTA GTT CTG TCC CCG CAG ACC GTG            1793
Asn Asp Val Leu Leu Gly Asn Tyr Val Val Leu Ser Pro Gln Thr Val
    555                 560                 565

CTC AAG AGC TCC AAG TTG GCC CCC GTG CAC CCT CTA GCA GAG CAG GTG            1841
Leu Lys Ser Ser Lys Leu Ala Pro Val His Pro Leu Ala Glu Gln Val
570                 575                 580                 585

AAA ATA ATA ACA CAT AAC GGG AGG GCC GGC GGT TAC CAG GTC GAC GGA            1889
Lys Ile Ile Thr His Asn Gly Arg Ala Gly Gly Tyr Gln Val Asp Gly
                590                 595                 600

TAT GAC GGC AGG GTC CTA CTA CCA TGT GGA TCG GCC ATT CCG GTC CCT            1937
Tyr Asp Gly Arg Val Leu Leu Pro Cys Gly Ser Ala Ile Pro Val Pro
            605                 610                 615
```

```
GAG TTT CAA GCT TTG AGC GAG AGC GCC ACT ATG GTG TAC AAC GAA AGG         1985
Glu Phe Gln Ala Leu Ser Glu Ser Ala Thr Met Val Tyr Asn Glu Arg
            620                 625                 630

GAG TTC GTC AAC AGG AAA CTA TAC CAT ATT GCC GTT CAC GGA CCG TCG         2033
Glu Phe Val Asn Arg Lys Leu Tyr His Ile Ala Val His Gly Pro Ser
635                 640                 645

CTG AAC ACC GAC GAG GAG AAC TAC GAG AAA GTC AGA GCT GAA AGA ACT         2081
Leu Asn Thr Asp Glu Glu Asn Tyr Glu Lys Val Arg Ala Glu Arg Thr
650                 655                 660                 665

GAC GCC GAG TAC GTG TTC GAC GTA GAT AAA AAA TGC TGC GTC AAG AGA         2129
Asp Ala Glu Tyr Val Phe Asp Val Asp Lys Lys Cys Cys Val Lys Arg
                670                 675                 680

GAG GAA GCG TCG GGT TTG GTG TTG GTG GGA GAG CTA ACC AAC CCC CCG         2177
Glu Glu Ala Ser Gly Leu Val Leu Val Gly Glu Leu Thr Asn Pro Pro
            685                 690                 695

TTC CAT GAA TTC GCC TAC GAA GGG CTG AAG ATC AGG CCG TCG GCA CCA         2225
Phe His Glu Phe Ala Tyr Glu Gly Leu Lys Ile Arg Pro Ser Ala Pro
700                 705                 710

TAT AAG ACT ACA GTA GTA GGA GTC TTT GGG GTT CCG GGA TCA GGC AAG         2273
Tyr Lys Thr Thr Val Val Gly Val Phe Gly Val Pro Gly Ser Gly Lys
715                 720                 725

TCT GCT ATT ATT AAG AGC CTC GTG ACC AAA CAC GAT CTG GTC ACC AGC         2321
Ser Ala Ile Ile Lys Ser Leu Val Thr Lys His Asp Leu Val Thr Ser
730                 735                 740                 745

GGC AAG AAG GAG AAC TGC CAG GAA ATA GTT AAC GAC GTG AAG AAG CAC         2369
Gly Lys Lys Glu Asn Cys Gln Glu Ile Val Asn Asp Val Lys Lys His
                750                 755                 760

CGC GGG AAG GGG ACA AGT AGG GAA AAC AGT GAC TCC ATC CTG CTA AAC         2417
Arg Gly Lys Gly Thr Ser Arg Glu Asn Ser Asp Ser Ile Leu Leu Asn
            765                 770                 775

GGG TGT CGT CGT GCC GTG GAC ATC CTA TAT GTG GAC GAG GCT TTC GCT         2465
Gly Cys Arg Arg Ala Val Asp Ile Leu Tyr Val Asp Glu Ala Phe Ala
780                 785                 790

TGC CAT TCC GGT ACT CTG CTG GCC CTA ATT GCT CTT GTT AAA CCT CGG         2513
Cys His Ser Gly Thr Leu Leu Ala Leu Ile Ala Leu Val Lys Pro Arg
795                 800                 805

AGC AAA GTG GTG TTA TGC GGA GAC CCC AAG CAA TGC GGA TTC TTC AAT         2561
Ser Lys Val Val Leu Cys Gly Asp Pro Lys Gln Cys Gly Phe Phe Asn
810                 815                 820                 825

ATG ATG CAG CTT AAG GTG AAC TTC AAC CAC AAC ATC TGC ACT GAA GTA         2609
Met Met Gln Leu Lys Val Asn Phe Asn His Asn Ile Cys Thr Glu Val
                830                 835                 840

TGT CAT AAA AGT ATA TCC AGA CGT TGC ACG CGT CCA GTC ACG GCC ATC         2657
Cys His Lys Ser Ile Ser Arg Arg Cys Thr Arg Pro Val Thr Ala Ile
            845                 850                 855

GTG TCT ACG TTG CAC TAC GGA GGC AAG ATG CGC ACG ACC AAC CCG TGC         2705
Val Ser Thr Leu His Tyr Gly Gly Lys Met Arg Thr Thr Asn Pro Cys
860                 865                 870

AAC AAA CCC ATA ATC ATA GAC ACC ACA GGA CAG ACC AAG CCC AAG CCA         2753
Asn Lys Pro Ile Ile Ile Asp Thr Thr Gly Gln Thr Lys Pro Lys Pro
875                 880                 885

GGA GAC ATC GTG TTA ACA TGC TTC CGA GGC TGG GCA AAG CAG CTG CAG         2801
Gly Asp Ile Val Leu Thr Cys Phe Arg Gly Trp Ala Lys Gln Leu Gln
890                 895                 900                 905

TTG GAC TAC CGT GGA CAC GAA GTC ATG ACA GCA GCA GCA TCT CAG GGC         2849
Leu Asp Tyr Arg Gly His Glu Val Met Thr Ala Ala Ala Ser Gln Gly
                910                 915                 920

CTC ACC CGC AAA GGG GTA TAC GCC GTA AGG CAG AAG GTG AAT GAA AAT         2897
Leu Thr Arg Lys Gly Val Tyr Ala Val Arg Gln Lys Val Asn Glu Asn
            925                 930                 935
```

```
CCC TTG TAT GCC CCT GCG TCG GAG CAC GTG AAT GTA CTG CTG ACG CGC    2945
Pro Leu Tyr Ala Pro Ala Ser Glu His Val Asn Val Leu Leu Thr Arg
        940             945                 950

ACT GAG GAT AGG CTG GTG TGG AAA ACG CTG GCC GGC GAT CCC TGG ATT    2993
Thr Glu Asp Arg Leu Val Trp Lys Thr Leu Ala Gly Asp Pro Trp Ile
955                 960                 965

AAG GTC CTA TCA AAC ATT CCA CAG GGT AAC TTT ACG GCC ACA TTG GAA    3041
Lys Val Leu Ser Asn Ile Pro Gln Gly Asn Phe Thr Ala Thr Leu Glu
970                 975                 980                 985

GAA TGG CAA GAA GAA CAC GAC AAA ATA ATG AAG GTG ATT GAA GGA CCG    3089
Glu Trp Gln Glu Glu His Asp Lys Ile Met Lys Val Ile Glu Gly Pro
                990                 995                 1000

GCT GCG CCT GTG GAC GCG TTC CAG AAC AAA GCG AAC GTG TGT TGG GCG    3137
Ala Ala Pro Val Asp Ala Phe Gln Asn Lys Ala Asn Val Cys Trp Ala
            1005                1010                1015

AAA AGC CTG GTG CCT GTC CTG GAC ACT GCC GGA ATC AGA TTG ACA GCA    3185
Lys Ser Leu Val Pro Val Leu Asp Thr Ala Gly Ile Arg Leu Thr Ala
        1020                1025                1030

GAG GAG TGG AGC ACC ATA ATT ACA GCA TTT AAG GAG GAC AGA GCT TAC    3233
Glu Glu Trp Ser Thr Ile Ile Thr Ala Phe Lys Glu Asp Arg Ala Tyr
1035                1040                1045

TCT CCA GTG GTG GCC TTG AAT GAA ATT TGC ACC AAG TAC TAT GGA GTT    3281
Ser Pro Val Val Ala Leu Asn Glu Ile Cys Thr Lys Tyr Tyr Gly Val
1050                1055                1060                1065

GAC CTG GAC AGT GGC CTG TTT TCT GCC CCG AAG GTG TCC CTG TAT TAC    3329
Asp Leu Asp Ser Gly Leu Phe Ser Ala Pro Lys Val Ser Leu Tyr Tyr
            1070                1075                1080

GAG AAC AAC CAC TGG GAT AAC AGA CCT GGT GGA AGG ATG TAT GGA TTC    3377
Glu Asn Asn His Trp Asp Asn Arg Pro Gly Gly Arg Met Tyr Gly Phe
        1085                1090                1095

AAT GCC GCA ACA GCT GCC AGG CTG GAA GCT AGA CAT ACC TTC CTG AAG    3425
Asn Ala Ala Thr Ala Ala Arg Leu Glu Ala Arg His Thr Phe Leu Lys
1100                1105                1110

GGG CAG TGG CAT ACG GGC AAG CAG GCA GTT ATC GCA GAA AGA AAA ATC    3473
Gly Gln Trp His Thr Gly Lys Gln Ala Val Ile Ala Glu Arg Lys Ile
1115                1120                1125

CAA CCG CTT TCT GTG CTG GAC AAT GTA ATT CCT ATC AAC CGC AGG CTG    3521
Gln Pro Leu Ser Val Leu Asp Asn Val Ile Pro Ile Asn Arg Arg Leu
1130                1135                1140                1145

CCG CAC GCC CTG GTG GCT GAG TAC AAG ACG GTT AAA GGC AGT AGG GTT    3569
Pro His Ala Leu Val Ala Glu Tyr Lys Thr Val Lys Gly Ser Arg Val
            1150                1155                1160

GAG TGG CTG GTC AAT AAA GTA AGA GGG TAC CAC GTC CTG CTG GTG AGT    3617
Glu Trp Leu Val Asn Lys Val Arg Gly Tyr His Val Leu Leu Val Ser
        1165                1170                1175

GAG TAC AAC CTG GCT TTG CCT CGA CGC AGG GTC ACT TGG TTG TCA CCG    3665
Glu Tyr Asn Leu Ala Leu Pro Arg Arg Arg Val Thr Trp Leu Ser Pro
1180                1185                1190

CTG AAT GTC ACA GGC GCC GAT AGG TGC TAC GAC CTA AGT TTA GGA CTG    3713
Leu Asn Val Thr Gly Ala Asp Arg Cys Tyr Asp Leu Ser Leu Gly Leu
1195                1200                1205

CCG GCT GAC GCC GGC AGG TTC GAC TTG GTC TTT GTG AAC ATT CAC ACG    3761
Pro Ala Asp Ala Gly Arg Phe Asp Leu Val Phe Val Asn Ile His Thr
1210                1215                1220                1225

GAA TTC AGA ATC CAC CAC TAC CAG CAG TGT GTC GAC CAC GCC ATG AAG    3809
Glu Phe Arg Ile His His Tyr Gln Gln Cys Val Asp His Ala Met Lys
            1230                1235                1240

CTG CAG ATG CTT GGG GGA GAT GCG CTA CGA CTG CTA AAA CCC GGC GGC    3857
Leu Gln Met Leu Gly Gly Asp Ala Leu Arg Leu Leu Lys Pro Gly Gly
```

```
                    1245                1250                1255
ATC TTG ATG AGA GCT TAC GGA TAC GCC GAT AAA ATC AGC GAA GCC GTT          3905
Ile Leu Met Arg Ala Tyr Gly Tyr Ala Asp Lys Ile Ser Glu Ala Val
        1260                1265                1270

GTT TCC TCC TTA AGC AGA AAG TTC TCG TCT GCA AGA GTG TTG CGC CCG          3953
Val Ser Ser Leu Ser Arg Lys Phe Ser Ser Ala Arg Val Leu Arg Pro
        1275                1280                1285

GAT TGT GTC ACC AGC AAT ACA GAA GTG TTC TTG CTG TTC TCC AAC TTT          4001
Asp Cys Val Thr Ser Asn Thr Glu Val Phe Leu Leu Phe Ser Asn Phe
1290                1295                1300                1305

GAC AAC GGA AAG AGA CCC TCT ACG CTA CAC CAG ATG AAT ACC AAG CTG          4049
Asp Asn Gly Lys Arg Pro Ser Thr Leu His Gln Met Asn Thr Lys Leu
                1310                1315                1320

AGT GCC GTG TAT GCC GGA GAA GCC ATG CAC ACG GCC GGG TGT GCA CCA          4097
Ser Ala Val Tyr Ala Gly Glu Ala Met His Thr Ala Gly Cys Ala Pro
        1325                1330                1335

TCC TAC AGA GTT AAG AGA GCA GAC ATA GCC ACG TGC ACA GAA GCG GCT          4145
Ser Tyr Arg Val Lys Arg Ala Asp Ile Ala Thr Cys Thr Glu Ala Ala
            1340                1345                1350

GTG GTT AAC GCA GCT AAC GCC CGT GGA ACT GTA GGG GAT GGC GTA TGC          4193
Val Val Asn Ala Ala Asn Ala Arg Gly Thr Val Gly Asp Gly Val Cys
        1355                1360                1365

AGG GCC GTG GCG AAG AAA TGG CCG TCA GCC TTT AAG GGA GCA GCA ACA          4241
Arg Ala Val Ala Lys Lys Trp Pro Ser Ala Phe Lys Gly Ala Ala Thr
1370                1375                1380                1385

CCA GTG GGC ACA ATT AAA ACA GTC ATG TGC GGC TCG TAC CCC GTC ATC          4289
Pro Val Gly Thr Ile Lys Thr Val Met Cys Gly Ser Tyr Pro Val Ile
                1390                1395                1400

CAC GCT GTA GCG CCT AAT TTC TCT GCC ACG ACT GAA GCG GAA GGG GAC          4337
His Ala Val Ala Pro Asn Phe Ser Ala Thr Thr Glu Ala Glu Gly Asp
            1405                1410                1415

CGC GAA TTG GCC GCT GTC TAC CGG GCA GTG GCC GCC GAA GTA AAC AGA          4385
Arg Glu Leu Ala Ala Val Tyr Arg Ala Val Ala Ala Glu Val Asn Arg
        1420                1425                1430

CTG TCA CTG AGC AGC GTA GCC ATC CCG CTG CTG TCC ACA GGA GTG TTC          4433
Leu Ser Leu Ser Ser Val Ala Ile Pro Leu Leu Ser Thr Gly Val Phe
        1435                1440                1445

AGC GGC GGA AGA GAT AGG CTG CAG CAA TCC CTC AAC CAT CTA TTC ACA          4481
Ser Gly Gly Arg Asp Arg Leu Gln Gln Ser Leu Asn His Leu Phe Thr
1450                1455                1460                1465

GCA ATG GAC GCC ACG GAC GCT GAC GTG ACC ATC TAC TGC AGA GAC AAA          4529
Ala Met Asp Ala Thr Asp Ala Asp Val Thr Ile Tyr Cys Arg Asp Lys
                1470                1475                1480

AGT TGG GAG AAG AAA ATC CAG GAA GCC ATT GAC ATG AGG ACG GCT GTG          4577
Ser Trp Glu Lys Lys Ile Gln Glu Ala Ile Asp Met Arg Thr Ala Val
            1485                1490                1495

GAG TTG CTC AAT GAT GAC GTG GAG CTG ACC ACA GAC TTG GTG AGA GTG          4625
Glu Leu Leu Asn Asp Asp Val Glu Leu Thr Thr Asp Leu Val Arg Val
        1500                1505                1510

CAC CCG GAC AGC AGC CTG GTG GGT CGT AAG GGC TAC AGT ACC ACT GAC          4673
His Pro Asp Ser Ser Leu Val Gly Arg Lys Gly Tyr Ser Thr Thr Asp
        1515                1520                1525

GGG TCG CTG TAC TCG TAC TTT GAA GGT ACG AAA TTC AAC CAG GCT GCT          4721
Gly Ser Leu Tyr Ser Tyr Phe Glu Gly Thr Lys Phe Asn Gln Ala Ala
1530                1535                1540                1545

ATT GAT ATG GCA GAG ATA CTG ACG TTG TGG CCC AGA CTG CAA GAG GCA          4769
Ile Asp Met Ala Glu Ile Leu Thr Leu Trp Pro Arg Leu Gln Glu Ala
                1550                1555                1560

AAC GAA CAG ATA TGC CTA TAC GCG CTG GGC GAA ACA ATG GAC AAC ATC          4817
Asn Glu Gln Ile Cys Leu Tyr Ala Leu Gly Glu Thr Met Asp Asn Ile
```

```
Asn Glu Gln Ile Cys Leu Tyr Ala Leu Gly Glu Thr Met Asp Asn Ile
            1565                1570                1575

AGA TCC AAA TGT CCG GTG AAC GAT TCC GAT TCA TCA ACA CCT CCC AGG        4865
Arg Ser Lys Cys Pro Val Asn Asp Ser Asp Ser Ser Thr Pro Pro Arg
        1580                1585                1590

ACA GTG CCC TGC CTG TGC CGC TAC GCA ATG ACA GCA GAA CGG ATC GCC        4913
Thr Val Pro Cys Leu Cys Arg Tyr Ala Met Thr Ala Glu Arg Ile Ala
    1595                1600                1605

CGC CTT AGG TCA CAC CAA GTT AAA AGC ATG GTG GTT TGC TCA TCT TTT        4961
Arg Leu Arg Ser His Gln Val Lys Ser Met Val Val Cys Ser Ser Phe
1610                1615                1620                1625

CCC CTC CCG AAA TAC CAT GTA GAT GGG GTG CAG AAG GTA AAG TGC GAG        5009
Pro Leu Pro Lys Tyr His Val Asp Gly Val Gln Lys Val Lys Cys Glu
            1630                1635                1640

AAG GTT CTC CTG TTC GAC CCG ACG GTA CCT TCA GTG GTT AGT CCG CGG        5057
Lys Val Leu Leu Phe Asp Pro Thr Val Pro Ser Val Val Ser Pro Arg
        1645                1650                1655

AAG TAT GCC GCA TCT ACG ACG GAC CAC TCA GAT CGG TCG TTA CGA GGG        5105
Lys Tyr Ala Ala Ser Thr Thr Asp His Ser Asp Arg Ser Leu Arg Gly
    1660                1665                1670

TTT GAC TTG GAC TGG ACC ACC GAC TCG TCT TCC ACT GCC AGC GAT ACC        5153
Phe Asp Leu Asp Trp Thr Thr Asp Ser Ser Ser Thr Ala Ser Asp Thr
1675                1680                1685

ATG TCG CTA CCC AGT TTG CAG TCG TGT GAC ATC GAC TCG ATC TAC GAG        5201
Met Ser Leu Pro Ser Leu Gln Ser Cys Asp Ile Asp Ser Ile Tyr Glu
1690                1695                1700                1705

CCA ATG GCT CCC ATA GTA GTG ACG GCT GAC GTA CAC CCT GAA CCC GCA        5249
Pro Met Ala Pro Ile Val Val Thr Ala Asp Val His Pro Glu Pro Ala
            1710                1715                1720

GGC ATC GCG GAC CTG GCG GCA GAT GTG CAC CCT GAA CCC GCA GAC CAT        5297
Gly Ile Ala Asp Leu Ala Ala Asp Val His Pro Glu Pro Ala Asp His
        1725                1730                1735

GTG GAC CTC GAG AAC CCG ATT CCT CCA CCG CGC CCG AAG AGA GCT GCA        5345
Val Asp Leu Glu Asn Pro Ile Pro Pro Pro Arg Pro Lys Arg Ala Ala
    1740                1745                1750

TAC CTT GCC TCC CGC GCG GCG GAG CGA CCG GTG CCG GCG CCG AGA AAG        5393
Tyr Leu Ala Ser Arg Ala Ala Glu Arg Pro Val Pro Ala Pro Arg Lys
1755                1760                1765

CCG ACG CCT GCC CCA AGG ACT GCG TTT AGG AAC AAG CTG CCT TTG ACG        5441
Pro Thr Pro Ala Pro Arg Thr Ala Phe Arg Asn Lys Leu Pro Leu Thr
1770                1775                1780                1785

TTC GGC GAC TTT GAC GAG CAC GAG GTC GAT GCG TTG GCC TCC GGG ATT        5489
Phe Gly Asp Phe Asp Glu His Glu Val Asp Ala Leu Ala Ser Gly Ile
            1790                1795                1800

ACT TTC GGA GAC TTC GAC GAC GTC CTG CGA CTA GGC CGC GCG GGT GCA        5537
Thr Phe Gly Asp Phe Asp Asp Val Leu Arg Leu Gly Arg Ala Gly Ala
        1805                1810                1815

TAT ATT TTC TCC TCG GAC ACT GGC AGC GGA CAT TTA CAA CAA AAA TCC        5585
Tyr Ile Phe Ser Ser Asp Thr Gly Ser Gly His Leu Gln Gln Lys Ser
    1820                1825                1830

GTT AGG CAG CAC AAT CTC CAG TGC GCA CAA CTG GAT GCG GTC CAG GAG        5633
Val Arg Gln His Asn Leu Gln Cys Ala Gln Leu Asp Ala Val Gln Glu
1835                1840                1845

GAG AAA ATG TAC CCG CCA AAA TTG GAT ACT GAG AGG GAG AAG CTG TTG        5681
Glu Lys Met Tyr Pro Pro Lys Leu Asp Thr Glu Arg Glu Lys Leu Leu
1850                1855                1860                1865

CTG CTG AAA ATG CAG ATG CAC CCA TCG GAG GCT AAT AAG AGT CGA TAC        5729
Leu Leu Lys Met Gln Met His Pro Ser Glu Ala Asn Lys Ser Arg Tyr
            1870                1875                1880
```

```
CAG TCT CGC AAA GTG GAG AAC ATG AAA GCC ACG GTG GTG GAC AGG CTC         5777
Gln Ser Arg Lys Val Glu Asn Met Lys Ala Thr Val Val Asp Arg Leu
            1885            1890            1895

ACA TCG GGG GCC AGA TTG TAC ACG GGA GCG GAC GTA GGC CGC ATA CCA         5825
Thr Ser Gly Ala Arg Leu Tyr Thr Gly Ala Asp Val Gly Arg Ile Pro
        1900            1905            1910

ACA TAC GCG GTT CGG TAC CCC CGC CCC GTG TAC TCC CCT ACC GTG ATC         5873
Thr Tyr Ala Val Arg Tyr Pro Arg Pro Val Tyr Ser Pro Thr Val Ile
        1915            1920            1925

GAA AGA TTC TCA AGC CCC GAT GTA GCA ATC GCA GCG TGC AAC GAA TAC         5921
Glu Arg Phe Ser Ser Pro Asp Val Ala Ile Ala Ala Cys Asn Glu Tyr
1930            1935            1940            1945

CTA TCC AGA AAT TAC CCA ACA GTG GCG TCG TAC CAG ATA ACA GAT GAA         5969
Leu Ser Arg Asn Tyr Pro Thr Val Ala Ser Tyr Gln Ile Thr Asp Glu
            1950            1955            1960

TAC GAC GCA TAC TTG GAC ATG GTT GAC GGG TCG GAT AGT TGC TTG GAC         6017
Tyr Asp Ala Tyr Leu Asp Met Val Asp Gly Ser Asp Ser Cys Leu Asp
        1965            1970            1975

AGA GCG ACA TTC TGC CCG GCG AAG CTC CGG TGC TAC CCG AAA CAT CAT         6065
Arg Ala Thr Phe Cys Pro Ala Lys Leu Arg Cys Tyr Pro Lys His His
        1980            1985            1990

GCG TAC CAC CAG CCG ACT GTA CGC AGT GCC GTC CCG TCA CCC TTT CAG         6113
Ala Tyr His Gln Pro Thr Val Arg Ser Ala Val Pro Ser Pro Phe Gln
        1995            2000            2005

AAC ACA CTA CAG AAC GTG CTA GCG GCC GCC ACC AAG AGA AAC TGC AAC         6161
Asn Thr Leu Gln Asn Val Leu Ala Ala Ala Thr Lys Arg Asn Cys Asn
2010            2015            2020            2025

GTC ACG CAA ATG CGA GAA CTA CCC ACC ATG GAC TCG GCA GTG TTC AAC         6209
Val Thr Gln Met Arg Glu Leu Pro Thr Met Asp Ser Ala Val Phe Asn
            2030            2035            2040

GTG GAG TGC TTC AAG CGC TAT GCC TGC TCC GGA GAA TAT TGG GAA GAA         6257
Val Glu Cys Phe Lys Arg Tyr Ala Cys Ser Gly Glu Tyr Trp Glu Glu
        2045            2050            2055

TAT GCT AAA CAA CCT ATC CGG ATA ACC ACT GAG AAC ATC ACT ACC TAT         6305
Tyr Ala Lys Gln Pro Ile Arg Ile Thr Thr Glu Asn Ile Thr Thr Tyr
        2060            2065            2070

GTG ACC AAA TTG AAA GGC CCG AAA GCT GCT GCC TTG TTC GCT AAG ACC         6353
Val Thr Lys Leu Lys Gly Pro Lys Ala Ala Ala Leu Phe Ala Lys Thr
        2075            2080            2085

CAC AAC TTG GTT CCG CTG CAG GAG GTT CCC ATG GAC AGA TTC ACG GTC         6401
His Asn Leu Val Pro Leu Gln Glu Val Pro Met Asp Arg Phe Thr Val
2090            2095            2100            2105

GAC ATG AAA CGA GAT GTC AAA GTC ACT CCA GGG ACG AAA CAC ACA GAG         6449
Asp Met Lys Arg Asp Val Lys Val Thr Pro Gly Thr Lys His Thr Glu
            2110            2115            2120

GAA AGA CCC AAA GTC CAG GTA ATT CAA GCA GCG GAG CCA TTG GCG ACC         6497
Glu Arg Pro Lys Val Gln Val Ile Gln Ala Ala Glu Pro Leu Ala Thr
        2125            2130            2135

GCT TAC CTG TGC GGC ATC CAC AGG GAA TTA GTA AGG AGA CTA AAT GCT         6545
Ala Tyr Leu Cys Gly Ile His Arg Glu Leu Val Arg Arg Leu Asn Ala
        2140            2145            2150

GTG TTA CGC CCT AAC GTG CAC ACA TTG TTT GAT ATG TCG GCC GAA GAC         6593
Val Leu Arg Pro Asn Val His Thr Leu Phe Asp Met Ser Ala Glu Asp
2155            2160            2165

TTT GAC GCG ATC ATC GCC TCT CAC TTC CAC CCA GGA GAC CCG GTT CTA         6641
Phe Asp Ala Ile Ile Ala Ser His Phe His Pro Gly Asp Pro Val Leu
2170            2175            2180            2185

GAG ACG GAC ATT GCA TCA TTC GAC AAA AGC CAG GAC GAC TCC TTG GCT         6689
Glu Thr Asp Ile Ala Ser Phe Asp Lys Ser Gln Asp Asp Ser Leu Ala
            2190            2195            2200
```

```
CTT ACA GGT TTA ATG ATC CTC GAA GAT CTA GGG GTG GAT CAG TAC CTG       6737
Leu Thr Gly Leu Met Ile Leu Glu Asp Leu Gly Val Asp Gln Tyr Leu
            2205                2210                2215

CTG GAC TTG ATC GAG GCA GCC TTT GGG GAA ATA TCC AGC TGT CAC CTA       6785
Leu Asp Leu Ile Glu Ala Ala Phe Gly Glu Ile Ser Ser Cys His Leu
        2220                2225                2230

CCA ACT GGC ACG CGC TTC AAG TTC GGA GCT ATG ATG AAA TCG GGC ATG       6833
Pro Thr Gly Thr Arg Phe Lys Phe Gly Ala Met Met Lys Ser Gly Met
        2235                2240                2245

TTT CTG ACT TTG TTT ATT AAC ACT GTT TTG AAC ATC ACC ATA GCA AGC       6881
Phe Leu Thr Leu Phe Ile Asn Thr Val Leu Asn Ile Thr Ile Ala Ser
2250                2255                2260                2265

AGG GTA CTG GAG CAG AGA CTC ACT GAC TCC GCC TGT GCG GCC TTC ATC       6929
Arg Val Leu Glu Gln Arg Leu Thr Asp Ser Ala Cys Ala Ala Phe Ile
            2270                2275                2280

GGC GAC GAC AAC ATC GTT CAC GGA GTG ATC TCC GAC AAG CTG ATG GCG       6977
Gly Asp Asp Asn Ile Val His Gly Val Ile Ser Asp Lys Leu Met Ala
        2285                2290                2295

GAG AGG TGC GCG TCG TGG GTC AAC ATG GAG GTG AAG ATC ATT GAC GCT       7025
Glu Arg Cys Ala Ser Trp Val Asn Met Glu Val Lys Ile Ile Asp Ala
        2300                2305                2310

GTC ATG GGC GAA AAA CCC CCA TAT TTT TGT GGG GGA TTC ATA GTT TTT       7073
Val Met Gly Glu Lys Pro Pro Tyr Phe Cys Gly Gly Phe Ile Val Phe
        2315                2320                2325

GAC AGC GTC ACA CAG ACC GCC TGC CGT GTT TCA GAC CCA CTT AAG CGC       7121
Asp Ser Val Thr Gln Thr Ala Cys Arg Val Ser Asp Pro Leu Lys Arg
2330                2335                2340                2345

CTG TTC AAG TTG GGT AAG CCG CTA ACA GCT GAA GAC AAG CAG GAC GAA       7169
Leu Phe Lys Leu Gly Lys Pro Leu Thr Ala Glu Asp Lys Gln Asp Glu
            2350                2355                2360

GAC AGG CGA CGA GCA CTG AGT GAC GAG GTT AGC AAG TGG TTC CGG ACA       7217
Asp Arg Arg Arg Ala Leu Ser Asp Glu Val Ser Lys Trp Phe Arg Thr
            2365                2370                2375

GGC TTG GGG GCC GAA CTG GAG GTG GCA CTA ACA TCT AGG TAT GAG GTA       7265
Gly Leu Gly Ala Glu Leu Glu Val Ala Leu Thr Ser Arg Tyr Glu Val
            2380                2385                2390

GAG GGC TGC AAA AGT ATC CTC ATA GCC ATG ACC ACC TTG GCG AGG GAC       7313
Glu Gly Cys Lys Ser Ile Leu Ile Ala Met Thr Thr Leu Ala Arg Asp
        2395                2400                2405

ATT AAG GCG TTT AAG AAA TTG AGA GGA CCT GTT ATA CAC CTC TAC GGC       7361
Ile Lys Ala Phe Lys Lys Leu Arg Gly Pro Val Ile His Leu Tyr Gly
2410                2415                2420                2425

GGT CCT AGA TTG GTG CGT TAATACACAG AATTCTGATT ATAGCGCACT              7409
Gly Pro Arg Leu Val Arg
            2430

ATTATAGCAC C ATG AAT TAC ATC CCT ACG CAA ACG TTT TAC GGC CGC CGG      7459
             Met Asn Tyr Ile Pro Thr Gln Thr Phe Tyr Gly Arg Arg
              1               5                   10

TGG CGC CCG CGC CCG GCG GCC CGT CCT TGG CCG TTG CAG GCC ACT CCG       7507
Trp Arg Pro Arg Pro Ala Ala Arg Pro Trp Pro Leu Gln Ala Thr Pro
        15                  20                  25

GTG GCT CCC GTC GTC CCC GAC TTC CAG GCC CAG CAG ATG CAG CAA CTC       7555
Val Ala Pro Val Val Pro Asp Phe Gln Ala Gln Gln Met Gln Gln Leu
30                  35                  40                  45

ATC AGC GCC GTA AAT GCG CTG ACA ATG AGA CAG AAC GCA ATT GCT CCT       7603
Ile Ser Ala Val Asn Ala Leu Thr Met Arg Gln Asn Ala Ile Ala Pro
            50                  55                  60

GCT AGG CCT CCC AAA CCA AAG AAG AAG AAG ACA ACC AAA CCA AAG CCG       7651
Ala Arg Pro Pro Lys Pro Lys Lys Lys Lys Thr Thr Lys Pro Lys Pro
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 65  |     |     |     |     | 70  |     |     |     |     | 75  |     |      |
| AAA | ACG | CAG | CCC | AAG | AAG | ATC | AAC | GGA | AAA | ACG | CAG | CAG | CAA | AAG | AAG | 7699 |
| Lys | Thr | Gln | Pro | Lys | Lys | Ile | Asn | Gly | Lys | Thr | Gln | Gln | Gln | Lys | Lys |      |
|     |     |     | 80  |     |     |     |     | 85  |     |     |     |     | 90  |     |     |      |
| AAA | GAC | AAG | CAA | GCC | GAC | AAG | AAG | AAG | AAA | CCC | GGA | AAA | AGA | GAA |     | 7747 |
| Lys | Asp | Lys | Gln | Ala | Asp | Lys | Lys | Lys | Lys | Pro | Gly | Lys | Arg | Glu |     |      |
|     | 95  |     |     |     |     | 100 |     |     |     |     | 105 |     |     |     |     |      |
| AGA | ATG | TGC | ATG | AAG | ATT | GAA | AAT | GAC | TGT | ATC | TTC | GAA | GTC | AAA | CAC | 7795 |
| Arg | Met | Cys | Met | Lys | Ile | Glu | Asn | Asp | Cys | Ile | Phe | Glu | Val | Lys | His |      |
| 110 |     |     |     |     | 115 |     |     |     |     | 120 |     |     |     |     | 125 |      |
| GAA | GGA | AAG | GTC | ACT | GGG | TAC | GCC | TGC | CTG | GTG | GGC | GAC | AAA | GTC | ATG | 7843 |
| Glu | Gly | Lys | Val | Thr | Gly | Tyr | Ala | Cys | Leu | Val | Gly | Asp | Lys | Val | Met |      |
|     |     |     |     | 130 |     |     |     |     | 135 |     |     |     |     | 140 |     |      |
| AAA | CCT | GCC | CAC | GTG | AAA | GGA | GTC | ATC | GAC | AAC | GCG | GAC | CTG | GCA | AAG | 7891 |
| Lys | Pro | Ala | His | Val | Lys | Gly | Val | Ile | Asp | Asn | Ala | Asp | Leu | Ala | Lys |      |
|     |     |     | 145 |     |     |     |     | 150 |     |     |     |     | 155 |     |     |      |
| CTA | GCT | TTC | AAG | AAA | TCG | AGC | AAG | TAT | GAC | CTT | GAG | TGT | GCC | CAG | ATA | 7939 |
| Leu | Ala | Phe | Lys | Lys | Ser | Ser | Lys | Tyr | Asp | Leu | Glu | Cys | Ala | Gln | Ile |      |
|     |     | 160 |     |     |     |     | 165 |     |     |     |     | 170 |     |     |     |      |
| CCA | GTT | CAC | ATG | AGG | TCG | GAT | GCC | TCA | AAG | TAC | ACG | CAT | GAG | AAG | CCC | 7987 |
| Pro | Val | His | Met | Arg | Ser | Asp | Ala | Ser | Lys | Tyr | Thr | His | Glu | Lys | Pro |      |
|     | 175 |     |     |     |     | 180 |     |     |     |     | 185 |     |     |     |     |      |
| GAG | GGA | CAC | TAT | AAC | TGG | CAC | CAC | GGG | GCT | GTT | CAG | TAC | AGC | GGA | GGT | 8035 |
| Glu | Gly | His | Tyr | Asn | Trp | His | His | Gly | Ala | Val | Gln | Tyr | Ser | Gly | Gly |      |
| 190 |     |     |     |     | 195 |     |     |     |     | 200 |     |     |     |     | 205 |      |
| AGG | TTC | ACT | ATA | CCG | ACA | GGA | GCG | GGC | AAA | CCG | GGA | GAC | AGT | GGC | CGG | 8083 |
| Arg | Phe | Thr | Ile | Pro | Thr | Gly | Ala | Gly | Lys | Pro | Gly | Asp | Ser | Gly | Arg |      |
|     |     |     |     | 210 |     |     |     |     | 215 |     |     |     |     | 220 |     |      |
| CCC | ATC | TTT | GAC | AAC | AAG | GGG | AGG | GTA | GTC | GCT | ATC | GTC | CTG | GGC | GGG | 8131 |
| Pro | Ile | Phe | Asp | Asn | Lys | Gly | Arg | Val | Val | Ala | Ile | Val | Leu | Gly | Gly |      |
|     |     |     | 225 |     |     |     |     | 230 |     |     |     |     | 235 |     |     |      |
| GCC | AAC | GAG | GGC | TCA | CGC | ACA | GCA | CTG | TCG | GTG | GTC | ACC | TGG | AAC | AAA | 8179 |
| Ala | Asn | Glu | Gly | Ser | Arg | Thr | Ala | Leu | Ser | Val | Val | Thr | Trp | Asn | Lys |      |
|     |     | 240 |     |     |     |     | 245 |     |     |     |     | 250 |     |     |     |      |
| GAT | ATG | GTG | ACT | AGA | GTG | ACC | CCC | GAG | GGG | TCC | GAA | GAG | TGG | TCC | GCC | 8227 |
| Asp | Met | Val | Thr | Arg | Val | Thr | Pro | Glu | Gly | Ser | Glu | Glu | Trp | Ser | Ala |      |
|     | 255 |     |     |     |     | 260 |     |     |     |     | 265 |     |     |     |     |      |
| CCG | CTG | ATT | ACT | GCC | ATG | TGT | GTC | CTT | GCC | AAT | GCT | ACC | TTC | CCG | TGC | 8275 |
| Pro | Leu | Ile | Thr | Ala | Met | Cys | Val | Leu | Ala | Asn | Ala | Thr | Phe | Pro | Cys |      |
| 270 |     |     |     |     | 275 |     |     |     |     | 280 |     |     |     |     | 285 |      |
| TTC | CAG | CCC | CCG | TGT | GTA | CCT | TGC | TGC | TAT | GAA | AAC | AAC | GCA | GAG | GCC | 8323 |
| Phe | Gln | Pro | Pro | Cys | Val | Pro | Cys | Cys | Tyr | Glu | Asn | Asn | Ala | Glu | Ala |      |
|     |     |     |     | 290 |     |     |     |     | 295 |     |     |     |     | 300 |     |      |
| ACA | CTA | CGG | ATG | CTC | GAG | GAT | AAC | GTG | GAT | AGG | CCA | GGG | TAC | TAC | GAC | 8371 |
| Thr | Leu | Arg | Met | Leu | Glu | Asp | Asn | Val | Asp | Arg | Pro | Gly | Tyr | Tyr | Asp |      |
|     |     |     | 305 |     |     |     |     | 310 |     |     |     |     | 315 |     |     |      |
| CTC | CTT | CAG | GCA | GCC | TTG | ACG | TGC | CGA | AAC | GGA | ACA | AGA | CAC | CGG | CGC | 8419 |
| Leu | Leu | Gln | Ala | Ala | Leu | Thr | Cys | Arg | Asn | Gly | Thr | Arg | His | Arg | Arg |      |
|     |     | 320 |     |     |     |     | 325 |     |     |     |     | 330 |     |     |     |      |
| AGC | GTG | TCG | CAA | CAC | TTC | AAC | GTG | TAT | AAG | GCT | ACA | CGC | CCT | TAC | ATC | 8467 |
| Ser | Val | Ser | Gln | His | Phe | Asn | Val | Tyr | Lys | Ala | Thr | Arg | Pro | Tyr | Ile |      |
|     | 335 |     |     |     |     | 340 |     |     |     |     | 345 |     |     |     |     |      |
| GCG | TAC | TGC | GCC | GAC | TGC | GGA | GCA | GGG | CAC | TCG | TGT | CAT | AGC | CCC | GTA | 8515 |
| Ala | Tyr | Cys | Ala | Asp | Cys | Gly | Ala | Gly | His | Ser | Cys | His | Ser | Pro | Val |      |
| 350 |     |     |     |     | 355 |     |     |     |     | 360 |     |     |     |     | 365 |      |
| GCA | ATT | GAA | GCG | GTC | AGG | TCC | GAA | GCT | ACC | GAC | GGG | ATG | CTG | AAG | ATT | 8563 |
| Ala | Ile | Glu | Ala | Val | Arg | Ser | Glu | Ala | Thr | Asp | Gly | Met | Leu | Lys | Ile |      |
|     |     |     |     | 370 |     |     |     |     | 375 |     |     |     |     | 380 |     |      |
| CAG | TTC | TCG | GCA | CAA | ATT | GGC | ATA | GAT | AAG | AGT | GAC | AAT | CAT | GAC | TAC | 8611 |

-continued

```
Gln Phe Ser Ala Gln Ile Gly Ile Asp Lys Ser Asp Asn His Asp Tyr
            385                 390                 395

ACG AAG ATA AGG TAC GCA GAC GGG CAC GCC ATT GAG AAT GCC GTC CGG      8659
Thr Lys Ile Arg Tyr Ala Asp Gly His Ala Ile Glu Asn Ala Val Arg
            400                 405                 410

TCA TCT TTG AAG GTA GCC ACC TCC GGA GAC TGT TTC GTC CAT GGC ACA      8707
Ser Ser Leu Lys Val Ala Thr Ser Gly Asp Cys Phe Val His Gly Thr
            415                 420                 425

ATG GGA CAT TTC ATA CTG GCA AAG TGC CCA CCG GGT GAA TTC CTG CAG      8755
Met Gly His Phe Ile Leu Ala Lys Cys Pro Pro Gly Glu Phe Leu Gln
430                 435                 440                 445

GTC TCG ATC CAG GAC ACC AGA AAC GCG GTC CGT GCC TGC AGA ATA CAA      8803
Val Ser Ile Gln Asp Thr Arg Asn Ala Val Arg Ala Cys Arg Ile Gln
                450                 455                 460

TAT CAT CAT GAC CCT CAA CCG GTG GGT AGA GAA AAA TTT ACA ATT AGA      8851
Tyr His His Asp Pro Gln Pro Val Gly Arg Glu Lys Phe Thr Ile Arg
                465                 470                 475

CCA CAC TAT GGA AAA GAG ATC CCT TGC ACC ACT TAT CAA CAG ACC ACA      8899
Pro His Tyr Gly Lys Glu Ile Pro Cys Thr Thr Tyr Gln Gln Thr Thr
                480                 485                 490

GCG AAG ACC GTG GAG GAA ATC GAC ATG CAT ATG CCG CCA GAT ACG CCG      8947
Ala Lys Thr Val Glu Glu Ile Asp Met His Met Pro Pro Asp Thr Pro
            495                 500                 505

GAC AGG ACG TTG CTA TCA CAG CAA TCT GGC AAT GTA AAG ATC ACA GTC      8995
Asp Arg Thr Leu Leu Ser Gln Gln Ser Gly Asn Val Lys Ile Thr Val
510                 515                 520                 525

GGA GGA AAG AAG GTG AAA TAC AAC TGC ACC TGT GGA ACC GGA AAC GTT      9043
Gly Gly Lys Lys Val Lys Tyr Asn Cys Thr Cys Gly Thr Gly Asn Val
                530                 535                 540

GGC ACT ACT AAT TCG GAC ATG ACG ATC AAC ACG TGT CTA ATA GAG CAG      9091
Gly Thr Thr Asn Ser Asp Met Thr Ile Asn Thr Cys Leu Ile Glu Gln
                545                 550                 555

TGC CAC GTC TCA GTG ACG GAC CAT AAG AAA TGG CAG TTC AAC TCA CCT      9139
Cys His Val Ser Val Thr Asp His Lys Lys Trp Gln Phe Asn Ser Pro
            560                 565                 570

TTC GTC CCG AGA GCC GAC GAA CCG GCT AGA AAA GGC AAA GTC CAT ATC      9187
Phe Val Pro Arg Ala Asp Glu Pro Ala Arg Lys Gly Lys Val His Ile
575                 580                 585

CCA TTC CCG TTG GAC AAC ATC ACA TGC AGA GTT CCA ATG GCG CGC GAA      9235
Pro Phe Pro Leu Asp Asn Ile Thr Cys Arg Val Pro Met Ala Arg Glu
590                 595                 600                 605

CCA ACC GTC ATC CAC GGC AAA AGA GAA GTG ACA CTG CAC CTT CAC CCA      9283
Pro Thr Val Ile His Gly Lys Arg Glu Val Thr Leu His Leu His Pro
                610                 615                 620

GAT CAT CCC ACG CTC TTT TCC TAC CGC ACA CTG GGT GAG GAC CCG CAG      9331
Asp His Pro Thr Leu Phe Ser Tyr Arg Thr Leu Gly Glu Asp Pro Gln
                625                 630                 635

TAT CAC GAG GAA TGG GTG ACA GCG GCG GTG GAA CGG ACC ATA CCC GTA      9379
Tyr His Glu Glu Trp Val Thr Ala Ala Val Glu Arg Thr Ile Pro Val
            640                 645                 650

CCA GTG GAC GGG ATG GAG TAC CAC TGG GGA AAC AAC GAC CCA GTG AGG      9427
Pro Val Asp Gly Met Glu Tyr His Trp Gly Asn Asn Asp Pro Val Arg
            655                 660                 665

CTT TGG TCT CAA CTC ACC ACT GAA GGG AAA CCG CAC GGC TGG CCG CAT      9475
Leu Trp Ser Gln Leu Thr Thr Glu Gly Lys Pro His Gly Trp Pro His
670                 675                 680                 685

CAG ATC GTA CAG TAC TAC TAT GGG CTT TAC CCG GCC GCT ACA GTA TCC      9523
Gln Ile Val Gln Tyr Tyr Tyr Gly Leu Tyr Pro Ala Ala Thr Val Ser
                690                 695                 700
```

```
                                           -continued
GCG GTC GTC GGG ATG AGC TTA CTG GCG TTG ATA TCG ATC TTC GCG TCG      9571
Ala Val Val Gly Met Ser Leu Leu Ala Leu Ile Ser Ile Phe Ala Ser
            705                 710                 715

TGC TAC ATG CTG GTT GCG GCC CGC AGT AAG TGC TTG ACC CCT TAT GCT      9619
Cys Tyr Met Leu Val Ala Ala Arg Ser Lys Cys Leu Thr Pro Tyr Ala
        720                 725                 730

TTA ACA CCA GGA GCT GCA GTT CCG TGG ACG CTG GGA ATA CTC TGC TGC      9667
Leu Thr Pro Gly Ala Ala Val Pro Trp Thr Leu Gly Ile Leu Cys Cys
    735                 740                 745

GCC CCG CGG GCG CAC GCA GCT AGT GTG GCA GAG ACT ATG GCC TAC TTG      9715
Ala Pro Arg Ala His Ala Ala Ser Val Ala Glu Thr Met Ala Tyr Leu
750                 755                 760                 765

TGG GAC CAA AAC CAA GCG TTG TTC TGG TTG GAG TTT GCG GCC CCT GTT      9763
Trp Asp Gln Asn Gln Ala Leu Phe Trp Leu Glu Phe Ala Ala Pro Val
                770                 775                 780

GCC TGC ATC CTC ATC ATC ACG TAT TGC CTC AGA AAC GTG CTG TGT TGC      9811
Ala Cys Ile Leu Ile Ile Thr Tyr Cys Leu Arg Asn Val Leu Cys Cys
            785                 790                 795

TGT AAG AGC CTT TCT TTT TTA GTG CTA CTG AGC CTC GGG GCA ACC GCC      9859
Cys Lys Ser Leu Ser Phe Leu Val Leu Leu Ser Leu Gly Ala Thr Ala
        800                 805                 810

AGA GCT TAC GAA CAT TCG ACA GTA ATG CCG AAC GTG GTG GGG TTC CCG      9907
Arg Ala Tyr Glu His Ser Thr Val Met Pro Asn Val Val Gly Phe Pro
    815                 820                 825

TAT AAG GCT CAC ATT GAA AGG CCA GGA TAT AGC CCC CTC ACT TTG CAG      9955
Tyr Lys Ala His Ile Glu Arg Pro Gly Tyr Ser Pro Leu Thr Leu Gln
830                 835                 840                 845

ATG CAG GTT GTT GAA ACC AGC CTC GAA CCA ACC CTT AAT TTG GAA TAC     10003
Met Gln Val Val Glu Thr Ser Leu Glu Pro Thr Leu Asn Leu Glu Tyr
                850                 855                 860

ATA ACC TGT GAG TAC AAG ACG GTC GTC CCG TCG CCG TAC GTG AAG TGC     10051
Ile Thr Cys Glu Tyr Lys Thr Val Val Pro Ser Pro Tyr Val Lys Cys
            865                 870                 875

TGC GGC GCC TCA GAG TGC TCC ACT AAA GAG AAG CCT GAC TAC CAA TGC     10099
Cys Gly Ala Ser Glu Cys Ser Thr Lys Glu Lys Pro Asp Tyr Gln Cys
        880                 885                 890

AAG GTT TAC ACA GGC GTG TAC CCG TTC ATG TGG GGA GGG GCA TAT TGC     10147
Lys Val Tyr Thr Gly Val Tyr Pro Phe Met Trp Gly Gly Ala Tyr Cys
    895                 900                 905

TTC TGC GAC TCA GAA AAC ACG CAA CTC AGC GAG GCG TAC GTC GAT CGA     10195
Phe Cys Asp Ser Glu Asn Thr Gln Leu Ser Glu Ala Tyr Val Asp Arg
910                 915                 920                 925

TCG GAC GTA TGC AGG CAT GAT CAC GCA TCT GCT TAC AAA GCC CAT ACA     10243
Ser Asp Val Cys Arg His Asp His Ala Ser Ala Tyr Lys Ala His Thr
                930                 935                 940

GCA TCG CTG AAG GCC AAA GTG AGG GTT ATG TAC GGC AAC GTA AAC CAG     10291
Ala Ser Leu Lys Ala Lys Val Arg Val Met Tyr Gly Asn Val Asn Gln
            945                 950                 955

ACT GTG GAT GTT TAC GTG AAC GGA GAC CAT GCC GTC ACG ATA GGG GGT     10339
Thr Val Asp Val Tyr Val Asn Gly Asp His Ala Val Thr Ile Gly Gly
        960                 965                 970

ACT CAG TTC ATA TTC GGG CCG CTG TCA TCG GCC TGG ACC CCG TTC GAC     10387
Thr Gln Phe Ile Phe Gly Pro Leu Ser Ser Ala Trp Thr Pro Phe Asp
    975                 980                 985

AAC AAG ATA GTC GTG TAC AAA GAC GAA GTG TTC AAT CAG GAC TTC CCG     10435
Asn Lys Ile Val Val Tyr Lys Asp Glu Val Phe Asn Gln Asp Phe Pro
990                 995                 1000                1005

CCG TAC GGA TCT GGG CAA CCA GGG CGC TTC GGC GAC ATC CAA AGC AGA     10483
Pro Tyr Gly Ser Gly Gln Pro Gly Arg Phe Gly Asp Ile Gln Ser Arg
                1010                1015                1020
```

```
ACA GTG GAG AGT AAC GAC CTG TAC GCG AAC ACG GCA CTG AAG CTG GCA        10531
Thr Val Glu Ser Asn Asp Leu Tyr Ala Asn Thr Ala Leu Lys Leu Ala
            1025                1030                1035

CGC CCT TCA CCC GGC ATG GTC CAT GTA CCG TAC ACA CAG ACA CCT TCA        10579
Arg Pro Ser Pro Gly Met Val His Val Pro Tyr Thr Gln Thr Pro Ser
            1040                1045                1050

GGG TTC AAA TAT TGG CTA AAG GAA AAA GGG ACA GCC CTA AAT ACG AAG        10627
Gly Phe Lys Tyr Trp Leu Lys Glu Lys Gly Thr Ala Leu Asn Thr Lys
            1055                1060                1065

GCT CCT TTT GGC TGC CAA ATC AAA ACG AAC CCT GTC AGG GCC ATG AAC        10675
Ala Pro Phe Gly Cys Gln Ile Lys Thr Asn Pro Val Arg Ala Met Asn
1070                1075                1080                1085

TGC GCC GTG GGA AAC ATC CCT GTC TCC ATG AAT TTG CCT GAC AGC GCC        10723
Cys Ala Val Gly Asn Ile Pro Val Ser Met Asn Leu Pro Asp Ser Ala
                1090                1095                1100

TTT ACC CGC ATT GTC GAG GCG CCG ACC ATC ATT GAC CTG ACT TGC ACA        10771
Phe Thr Arg Ile Val Glu Ala Pro Thr Ile Ile Asp Leu Thr Cys Thr
            1105                1110                1115

GTG GCT ACC TGT ACG CAC TCC TCG GAT TTC GGC GGC GTC TTG ACA CTG        10819
Val Ala Thr Cys Thr His Ser Ser Asp Phe Gly Gly Val Leu Thr Leu
            1120                1125                1130

ACG TAC AAG ACC AAC AAG AAC GGG GAC TGC TCT GTA CAC TCG CAC TCT        10867
Thr Tyr Lys Thr Asn Lys Asn Gly Asp Cys Ser Val His Ser His Ser
            1135                1140                1145

AAC GTA GCT ACT CTA CAG GAG GCC ACA GCA AAA GTG AAG ACA GCA GGT        10915
Asn Val Ala Thr Leu Gln Glu Ala Thr Ala Lys Val Lys Thr Ala Gly
1150                1155                1160                1165

AAG GTG ACC TTA CAC TTC TCC ACG GCA AGC GCA TCA CCT TCT TTT GTG        10963
Lys Val Thr Leu His Phe Ser Thr Ala Ser Ala Ser Pro Ser Phe Val
                1170                1175                1180

GTG TCG CTA TGC AGT GCT AGG GCC ACC TGT TCA GCG TCG TGT GAG CCC        11011
Val Ser Leu Cys Ser Ala Arg Ala Thr Cys Ser Ala Ser Cys Glu Pro
            1185                1190                1195

CCG AAA GAC CAC ATA GTC CCA TAT GCG GCT AGC CAC AGT AAC GTA GTG        11059
Pro Lys Asp His Ile Val Pro Tyr Ala Ala Ser His Ser Asn Val Val
            1200                1205                1210

TTT CCA GAC ATG TCG GGC ACC GCA CTA TCA TGG GTG CAG AAA ATC TCG        11107
Phe Pro Asp Met Ser Gly Thr Ala Leu Ser Trp Val Gln Lys Ile Ser
            1215                1220                1225

GGT GGT CTG GGG GCC TTC GCA ATC GGC GCT ATC CTG GTG CTG GTT GTG        11155
Gly Gly Leu Gly Ala Phe Ala Ile Gly Ala Ile Leu Val Leu Val Val
1230                1235                1240                1245

GTC ACT TGC ATT GGG CTC CGC AGA TAAGTTAGGG TAGGCAATGG CATTGATATA       11209
Val Thr Cys Ile Gly Leu Arg Arg
            1250

GCAAGAAAAT TGAAAACAGA AAAAGTTAGG GTAAGCAATG GCATATAACC ATAACTGTAT      11269

AACTTGTAAC AAAGCGCAAC AAGACCTGCG CAATTGGCCC CGTGGTCCGC CTCACGGAAA      11329

CTCGGGGCAA CTCATATTGA CACATTAATT GGCAATAATT GGAAGCTTAC ATAAGCTTAA      11389

TTCGACGAAT AATTGGATTT TTATTTTATT TTGCAATTGG TTTTTAATAT TTCCAAAAAA      11449

AAAAAAAAAA AAAAAAAAAA AAAAAAAAAA AAAAAAAAAA AAAAAAAAAA AAAAAAAAAA      11509

AAAACTAG                                                               11517

(2) INFORMATION FOR SEQ ID NO: 2:

(i) SEQUENCE CHARACTERISTICS:
        (A) LENGTH: 2431 amino acids
        (B) TYPE: amino acid
```

-continued (D) TOPOLOGY: linear (ii) MOLECULE TYPE: protein (xi) SEQUENCE DESCRIPTION: SEQ ID NO: 2:

```
Met Ala Ala Lys Val His Val Asp Ile Glu Ala Asp Ser Pro Phe Ile
 1               5                  10                  15

Lys Ser Leu Gln Lys Ala Phe Pro Ser Phe Glu Val Glu Ser Leu Gln
                20                  25                  30

Val Thr Pro Asn Asp His Ala Asn Ala Arg Ala Phe Ser His Leu Ala
            35                  40                  45

Thr Lys Leu Ile Glu Gln Glu Thr Asp Lys Asp Thr Leu Ile Leu Asp
        50                  55                  60

Ile Gly Ser Ala Pro Ser Arg Arg Met Met Ser Thr His Lys Tyr His
 65                 70                  75                  80

Cys Val Cys Pro Met Arg Ser Ala Glu Asp Pro Glu Arg Leu Asp Ser
                85                  90                  95

Tyr Ala Lys Lys Leu Ala Ala Ala Ser Gly Lys Val Leu Asp Arg Glu
                100                 105                 110

Ile Ala Gly Lys Ile Thr Asp Leu Gln Thr Val Met Ala Thr Pro Asp
                115                 120                 125

Ala Glu Ser Pro Thr Phe Cys Leu His Thr Asp Val Thr Cys Arg Thr
            130                 135                 140

Ala Ala Glu Val Ala Val Tyr Gln Asp Val Tyr Ala Val His Ala Pro
145                 150                 155                 160

Thr Ser Leu Tyr His Gln Ala Met Lys Gly Val Arg Thr Ala Tyr Trp
                165                 170                 175

Ile Gly Phe Asp Thr Thr Pro Phe Met Phe Asp Ala Leu Ala Gly Ala
                180                 185                 190

Tyr Pro Thr Tyr Ala Thr Asn Trp Ala Asp Glu Gln Val Leu Gln Ala
                195                 200                 205

Arg Asn Ile Gly Leu Cys Ala Ala Ser Leu Thr Glu Gly Arg Leu Gly
        210                 215                 220

Lys Leu Ser Ile Leu Arg Lys Lys Gln Leu Lys Pro Cys Asp Thr Val
225                 230                 235                 240

Met Phe Ser Val Gly Ser Thr Leu Tyr Thr Glu Ser Arg Lys Leu Leu
                245                 250                 255

Arg Ser Trp His Leu Pro Ser Val Phe His Leu Lys Gly Lys Gln Ser
                260                 265                 270

Phe Thr Cys Arg Cys Asp Thr Ile Val Ser Cys Glu Gly Tyr Val Val
                275                 280                 285

Lys Lys Ile Thr Met Cys Pro Gly Leu Tyr Gly Lys Thr Val Gly Tyr
                290                 295                 300

Ala Val Thr Tyr His Ala Glu Gly Phe Leu Val Cys Lys Thr Thr Asp
305                 310                 315                 320

Thr Val Lys Gly Glu Arg Val Ser Phe Pro Val Cys Thr Tyr Val Pro
                325                 330                 335

Ser Thr Ile Cys Asp Gln Met Thr Gly Ile Leu Ala Thr Asp Val Thr
                340                 345                 350

Pro Glu Asp Ala Gln Lys Leu Leu Val Gly Leu Asn Gln Arg Ile Val
            355                 360                 365

Val Asn Gly Arg Thr Gln Arg Asn Thr Asn Thr Met Lys Asn Tyr Leu
370                 375                 380
```

```
Leu Pro Ile Val Ala Val Ala Phe Ser Lys Trp Ala Arg Glu Tyr Lys
385                 390                 395                 400

Ala Asp Leu Asp Asp Glu Lys Pro Leu Gly Val Arg Glu Arg Ser Leu
                405                 410                 415

Thr Cys Cys Cys Leu Trp Ala Phe Lys Thr Arg Lys Met His Thr Met
            420                 425                 430

Tyr Lys Lys Pro Asp Thr Gln Thr Ile Val Lys Val Pro Ser Glu Phe
        435                 440                 445

Asn Ser Phe Val Ile Pro Ser Leu Trp Ser Thr Gly Leu Ala Ile Pro
450                 455                 460

Val Arg Ser Arg Ile Lys Met Leu Leu Ala Lys Lys Thr Lys Arg Glu
465                 470                 475                 480

Leu Ile Pro Val Leu Asp Ala Ser Ser Ala Arg Asp Ala Glu Gln Glu
                485                 490                 495

Glu Lys Glu Arg Leu Glu Ala Glu Leu Thr Arg Glu Ala Leu Pro Pro
            500                 505                 510

Leu Val Pro Ile Ala Pro Ala Glu Thr Gly Val Val Asp Val Asp Val
        515                 520                 525

Glu Glu Leu Glu Tyr His Ala Gly Ala Gly Val Val Glu Thr Pro Arg
530                 535                 540

Ser Ala Leu Lys Val Thr Ala Gln Pro Asn Asp Val Leu Leu Gly Asn
545                 550                 555                 560

Tyr Val Val Leu Ser Pro Gln Thr Val Leu Lys Ser Ser Lys Leu Ala
                565                 570                 575

Pro Val His Pro Leu Ala Glu Gln Val Lys Ile Ile Thr His Asn Gly
            580                 585                 590

Arg Ala Gly Gly Tyr Gln Val Asp Gly Tyr Asp Gly Arg Val Leu Leu
        595                 600                 605

Pro Cys Gly Ser Ala Ile Pro Val Pro Glu Phe Gln Ala Leu Ser Glu
610                 615                 620

Ser Ala Thr Met Val Tyr Asn Glu Arg Glu Phe Val Asn Arg Lys Leu
625                 630                 635                 640

Tyr His Ile Ala Val His Gly Pro Ser Leu Asn Thr Asp Glu Glu Asn
                645                 650                 655

Tyr Glu Lys Val Arg Ala Glu Arg Thr Asp Ala Glu Tyr Val Phe Asp
            660                 665                 670

Val Asp Lys Lys Cys Cys Val Lys Arg Glu Glu Ala Ser Gly Leu Val
        675                 680                 685

Leu Val Gly Glu Leu Thr Asn Pro Pro Phe His Glu Phe Ala Tyr Glu
690                 695                 700

Gly Leu Lys Ile Arg Pro Ser Ala Pro Tyr Lys Thr Thr Val Val Gly
705                 710                 715                 720

Val Phe Gly Val Pro Gly Ser Gly Lys Ser Ala Ile Ile Lys Ser Leu
                725                 730                 735

Val Thr Lys His Asp Leu Val Thr Ser Gly Lys Lys Glu Asn Cys Gln
            740                 745                 750

Glu Ile Val Asn Asp Val Lys Lys His Arg Gly Lys Gly Thr Ser Arg
        755                 760                 765

Glu Asn Ser Asp Ser Ile Leu Leu Asn Gly Cys Arg Arg Ala Val Asp
770                 775                 780

Ile Leu Tyr Val Asp Glu Ala Phe Ala Cys His Ser Gly Thr Leu Leu
785                 790                 795                 800
```

```
Ala Leu Ile Ala Leu Val Lys Pro Arg Ser Lys Val Val Leu Cys Gly
                805                 810                 815

Asp Pro Lys Gln Cys Gly Phe Phe Asn Met Met Gln Leu Lys Val Asn
            820                 825                 830

Phe Asn His Asn Ile Cys Thr Glu Val Cys His Lys Ser Ile Ser Arg
        835                 840                 845

Arg Cys Thr Arg Pro Val Thr Ala Ile Val Ser Thr Leu His Tyr Gly
    850                 855                 860

Gly Lys Met Arg Thr Thr Asn Pro Cys Asn Lys Pro Ile Ile Ile Asp
865                 870                 875                 880

Thr Thr Gly Gln Thr Lys Pro Lys Pro Gly Asp Ile Val Leu Thr Cys
                885                 890                 895

Phe Arg Gly Trp Ala Lys Gln Leu Gln Leu Asp Tyr Arg Gly His Glu
            900                 905                 910

Val Met Thr Ala Ala Ser Gln Gly Leu Thr Arg Lys Gly Val Tyr
        915                 920                 925

Ala Val Arg Gln Lys Val Asn Glu Asn Pro Leu Tyr Ala Pro Ala Ser
    930                 935                 940

Glu His Val Asn Val Leu Leu Thr Arg Thr Glu Asp Arg Leu Val Trp
945                 950                 955                 960

Lys Thr Leu Ala Gly Asp Pro Trp Ile Lys Val Leu Ser Asn Ile Pro
                965                 970                 975

Gln Gly Asn Phe Thr Ala Thr Leu Glu Glu Trp Gln Glu Glu His Asp
            980                 985                 990

Lys Ile Met Lys Val Ile Glu Gly Pro Ala Ala Pro Val Asp Ala Phe
        995                 1000                1005

Gln Asn Lys Ala Asn Val Cys Trp Ala Lys Ser Leu Val Pro Val Leu
    1010                1015                1020

Asp Thr Ala Gly Ile Arg Leu Thr Ala Glu Glu Trp Ser Thr Ile Ile
1025                1030                1035                1040

Thr Ala Phe Lys Glu Asp Arg Ala Tyr Ser Pro Val Val Ala Leu Asn
                1045                1050                1055

Glu Ile Cys Thr Lys Tyr Tyr Gly Val Asp Leu Asp Ser Gly Leu Phe
            1060                1065                1070

Ser Ala Pro Lys Val Ser Leu Tyr Tyr Glu Asn Asn His Trp Asp Asn
        1075                1080                1085

Arg Pro Gly Gly Arg Met Tyr Gly Phe Asn Ala Ala Thr Ala Ala Arg
    1090                1095                1100

Leu Glu Ala Arg His Thr Phe Leu Lys Gly Gln Trp His Thr Gly Lys
1105                1110                1115                1120

Gln Ala Val Ile Ala Glu Arg Lys Ile Gln Pro Leu Ser Val Leu Asp
                1125                1130                1135

Asn Val Ile Pro Ile Asn Arg Arg Leu Pro His Ala Leu Val Ala Glu
            1140                1145                1150

Tyr Lys Thr Val Lys Gly Ser Arg Val Glu Trp Leu Val Asn Lys Val
        1155                1160                1165

Arg Gly Tyr His Val Leu Leu Val Ser Glu Tyr Asn Leu Ala Leu Pro
    1170                1175                1180

Arg Arg Arg Val Thr Trp Leu Ser Pro Leu Asn Val Thr Gly Ala Asp
1185                1190                1195                1200

Arg Cys Tyr Asp Leu Ser Leu Gly Leu Pro Ala Asp Ala Gly Arg Phe
                1205                1210                1215

Asp Leu Val Phe Val Asn Ile His Thr Glu Phe Arg Ile His His Tyr
```

-continued

```
                 1220                1225                1230
Gln Gln Cys Val Asp His Ala Met Lys Leu Gln Met Leu Gly Gly Asp
    1235                1240                1245
Ala Leu Arg Leu Leu Lys Pro Gly Gly Ile Leu Met Arg Ala Tyr Gly
    1250                1255                1260
Tyr Ala Asp Lys Ile Ser Glu Ala Val Val Ser Ser Leu Ser Arg Lys
1265                1270                1275                1280
Phe Ser Ser Ala Arg Val Leu Arg Pro Asp Cys Val Thr Ser Asn Thr
            1285                1290                1295
Glu Val Phe Leu Leu Phe Ser Asn Phe Asp Asn Gly Lys Arg Pro Ser
        1300                1305                1310
Thr Leu His Gln Met Asn Thr Lys Leu Ser Ala Val Tyr Ala Gly Glu
    1315                1320                1325
Ala Met His Thr Ala Gly Cys Ala Pro Ser Tyr Arg Val Lys Arg Ala
    1330                1335                1340
Asp Ile Ala Thr Cys Thr Glu Ala Ala Val Val Asn Ala Ala Asn Ala
1345                1350                1355                1360
Arg Gly Thr Val Gly Asp Gly Val Cys Arg Ala Val Ala Lys Lys Trp
            1365                1370                1375
Pro Ser Ala Phe Lys Gly Ala Ala Thr Pro Val Gly Thr Ile Lys Thr
        1380                1385                1390
Val Met Cys Gly Ser Tyr Pro Val Ile His Ala Val Ala Pro Asn Phe
    1395                1400                1405
Ser Ala Thr Thr Glu Ala Glu Gly Asp Arg Glu Leu Ala Ala Val Tyr
    1410                1415                1420
Arg Ala Val Ala Ala Glu Val Asn Arg Leu Ser Leu Ser Ser Val Ala
1425                1430                1435                1440
Ile Pro Leu Leu Ser Thr Gly Val Phe Ser Gly Gly Arg Asp Arg Leu
            1445                1450                1455
Gln Gln Ser Leu Asn His Leu Phe Thr Ala Met Asp Ala Thr Asp Ala
        1460                1465                1470
Asp Val Thr Ile Tyr Cys Arg Asp Lys Ser Trp Glu Lys Lys Ile Gln
    1475                1480                1485
Glu Ala Ile Asp Met Arg Thr Ala Val Glu Leu Leu Asn Asp Asp Val
    1490                1495                1500
Glu Leu Thr Thr Asp Leu Val Arg Val His Pro Asp Ser Ser Leu Val
1505                1510                1515                1520
Gly Arg Lys Gly Tyr Ser Thr Thr Asp Gly Ser Leu Tyr Ser Tyr Phe
            1525                1530                1535
Glu Gly Thr Lys Phe Asn Gln Ala Ala Ile Asp Met Ala Glu Ile Leu
        1540                1545                1550
Thr Leu Trp Pro Arg Leu Gln Glu Ala Asn Glu Gln Ile Cys Leu Tyr
    1555                1560                1565
Ala Leu Gly Glu Thr Met Asp Asn Ile Arg Ser Lys Cys Pro Val Asn
    1570                1575                1580
Asp Ser Asp Ser Ser Thr Pro Pro Arg Thr Val Pro Cys Leu Cys Arg
1585                1590                1595                1600
Tyr Ala Met Thr Ala Glu Arg Ile Ala Arg Leu Arg Ser His Gln Val
            1605                1610                1615
Lys Ser Met Val Val Cys Ser Ser Phe Pro Leu Pro Lys Tyr His Val
        1620                1625                1630
Asp Gly Val Gln Lys Val Lys Cys Glu Lys Val Leu Leu Phe Asp Pro
    1635                1640                1645
```

-continued

```
Thr Val Pro Ser Val Val Ser Pro Arg Lys Tyr Ala Ala Ser Thr Thr
    1650                1655                1660
Asp His Ser Asp Arg Ser Leu Arg Gly Phe Asp Leu Asp Trp Thr Thr
1665                1670                1675                1680
Asp Ser Ser Ser Thr Ala Ser Asp Thr Met Ser Leu Pro Ser Leu Gln
                1685                1690                1695
Ser Cys Asp Ile Asp Ser Ile Tyr Glu Pro Met Ala Pro Ile Val Val
                1700                1705                1710
Thr Ala Asp Val His Pro Glu Pro Ala Gly Ile Ala Asp Leu Ala Ala
            1715                1720                1725
Asp Val His Pro Glu Pro Ala Asp His Val Asp Leu Glu Asn Pro Ile
        1730                1735                1740
Pro Pro Pro Arg Pro Lys Arg Ala Ala Tyr Leu Ala Ser Arg Ala Ala
1745                1750                1755                1760
Glu Arg Pro Val Pro Ala Pro Arg Lys Pro Thr Pro Ala Pro Arg Thr
                1765                1770                1775
Ala Phe Arg Asn Lys Leu Pro Leu Thr Phe Gly Asp Phe Asp Glu His
            1780                1785                1790
Glu Val Asp Ala Leu Ala Ser Gly Ile Thr Phe Gly Asp Phe Asp Asp
        1795                1800                1805
Val Leu Arg Leu Gly Arg Ala Gly Ala Tyr Ile Phe Ser Ser Asp Thr
    1810                1815                1820
Gly Ser Gly His Leu Gln Gln Lys Ser Val Arg Gln His Asn Leu Gln
1825                1830                1835                1840
Cys Ala Gln Leu Asp Ala Val Gln Glu Glu Lys Met Tyr Pro Pro Lys
                1845                1850                1855
Leu Asp Thr Glu Arg Glu Lys Leu Leu Leu Leu Lys Met Gln Met His
            1860                1865                1870
Pro Ser Glu Ala Asn Lys Ser Arg Tyr Gln Ser Arg Lys Val Glu Asn
        1875                1880                1885
Met Lys Ala Thr Val Val Asp Arg Leu Thr Ser Gly Ala Arg Leu Tyr
    1890                1895                1900
Thr Gly Ala Asp Val Gly Arg Ile Pro Thr Tyr Ala Val Arg Tyr Pro
1905                1910                1915                1920
Arg Pro Val Tyr Ser Pro Thr Val Ile Glu Arg Phe Ser Ser Pro Asp
                1925                1930                1935
Val Ala Ile Ala Ala Cys Asn Glu Tyr Leu Ser Arg Asn Tyr Pro Thr
            1940                1945                1950
Val Ala Ser Tyr Gln Ile Thr Asp Glu Tyr Asp Ala Tyr Leu Asp Met
        1955                1960                1965
Val Asp Gly Ser Asp Ser Cys Leu Asp Arg Ala Thr Phe Cys Pro Ala
    1970                1975                1980
Lys Leu Arg Cys Tyr Pro Lys His His Ala Tyr His Gln Pro Thr Val
1985                1990                1995                2000
Arg Ser Ala Val Pro Ser Pro Phe Gln Asn Thr Leu Gln Asn Val Leu
                2005                2010                2015
Ala Ala Ala Thr Lys Arg Asn Cys Asn Val Thr Gln Met Arg Glu Leu
            2020                2025                2030
Pro Thr Met Asp Ser Ala Val Phe Asn Val Glu Cys Phe Lys Arg Tyr
        2035                2040                2045
Ala Cys Ser Gly Glu Tyr Trp Glu Glu Tyr Ala Lys Gln Pro Ile Arg
    2050                2055                2060
```

Ile Thr Thr Glu Asn Ile Thr Thr Tyr Val Thr Lys Leu Lys Gly Pro
2065                2070                2075                2080

Lys Ala Ala Ala Leu Phe Ala Lys Thr His Asn Leu Val Pro Leu Gln
            2085                2090                2095

Glu Val Pro Met Asp Arg Phe Thr Val Asp Met Lys Arg Asp Val Lys
        2100                2105                2110

Val Thr Pro Gly Thr Lys His Thr Glu Glu Arg Pro Lys Val Gln Val
    2115                2120                2125

Ile Gln Ala Ala Glu Pro Leu Ala Thr Ala Tyr Leu Cys Gly Ile His
2130                2135                2140

Arg Glu Leu Val Arg Arg Leu Asn Ala Val Leu Arg Pro Asn Val His
2145                2150                2155                2160

Thr Leu Phe Asp Met Ser Ala Glu Asp Phe Asp Ala Ile Ile Ala Ser
            2165                2170                2175

His Phe His Pro Gly Asp Pro Val Leu Glu Thr Asp Ile Ala Ser Phe
        2180                2185                2190

Asp Lys Ser Gln Asp Asp Ser Leu Ala Leu Thr Gly Leu Met Ile Leu
    2195                2200                2205

Glu Asp Leu Gly Val Asp Gln Tyr Leu Leu Asp Leu Ile Glu Ala Ala
2210                2215                2220

Phe Gly Glu Ile Ser Ser Cys His Leu Pro Thr Gly Thr Arg Phe Lys
2225                2230                2235                2240

Phe Gly Ala Met Met Lys Ser Gly Met Phe Leu Thr Leu Phe Ile Asn
            2245                2250                2255

Thr Val Leu Asn Ile Thr Ile Ala Ser Arg Val Leu Glu Gln Arg Leu
        2260                2265                2270

Thr Asp Ser Ala Cys Ala Ala Phe Ile Gly Asp Asn Ile Val His
    2275                2280                2285

Gly Val Ile Ser Asp Lys Leu Met Ala Glu Arg Cys Ala Ser Trp Val
2290                2295                2300

Asn Met Glu Val Lys Ile Ile Asp Ala Val Met Gly Glu Lys Pro Pro
2305                2310                2315                2320

Tyr Phe Cys Gly Gly Phe Ile Val Phe Asp Ser Val Thr Gln Thr Ala
            2325                2330                2335

Cys Arg Val Ser Asp Pro Leu Lys Arg Leu Phe Lys Leu Gly Lys Pro
        2340                2345                2350

Leu Thr Ala Glu Asp Lys Gln Asp Glu Asp Arg Arg Arg Ala Leu Ser
    2355                2360                2365

Asp Glu Val Ser Lys Trp Phe Arg Thr Gly Leu Gly Ala Glu Leu Glu
    2370                2375                2380

Val Ala Leu Thr Ser Arg Tyr Glu Val Glu Gly Cys Lys Ser Ile Leu
2385                2390                2395                2400

Ile Ala Met Thr Thr Leu Ala Arg Asp Ile Lys Ala Phe Lys Lys Leu
            2405                2410                2415

Arg Gly Pro Val Ile His Leu Tyr Gly Gly Pro Arg Leu Val Arg
        2420                2425                2430

(2) INFORMATION FOR SEQ ID NO: 3:

(i) SEQUENCE CHARACTERISTICS:
        (A) LENGTH: 1253 amino acids
        (B) TYPE: amino acid
        (D) TOPOLOGY: linear (ii) MOLECULE TYPE: protein (xi) SEQUENCE DESCRIPTION: SEQ ID NO: 3:

| | | | | | | | | | | | | | | |
|---|---|---|---|---|---|---|---|---|---|---|---|---|---|---|
|Met|Asn|Tyr|Ile|Pro|Thr|Gln|Thr|Phe|Tyr|Gly|Arg|Arg|Trp|Arg|Pro
|1| | | |5| | | | |10| | | | |15|

Arg Pro Ala Ala Arg Pro Trp Pro Leu Gln Ala Thr Pro Val Ala Pro
          20              25              30

Val Val Pro Asp Phe Gln Ala Gln Gln Met Gln Gln Leu Ile Ser Ala
        35              40              45

Val Asn Ala Leu Thr Met Arg Gln Asn Ala Ile Ala Pro Ala Arg Pro
50              55              60

Pro Lys Pro Lys Lys Lys Thr Thr Lys Pro Lys Pro Lys Thr Gln
65          70              75            80

Pro Lys Lys Ile Asn Gly Lys Thr Gln Gln Lys Lys Asp Lys
        85              90            95

Gln Ala Asp Lys Lys Lys Lys Pro Gly Lys Arg Glu Arg Met Cys
       100           105          110

Met Lys Ile Glu Asn Asp Cys Ile Phe Glu Val Lys His Glu Gly Lys
    115              120           125

Val Thr Gly Tyr Ala Cys Leu Val Gly Asp Lys Val Met Lys Pro Ala
130              135            140

His Val Lys Gly Val Ile Asp Asn Ala Asp Leu Ala Lys Leu Ala Phe
145          150            155           160

Lys Lys Ser Ser Lys Tyr Asp Leu Glu Cys Ala Gln Ile Pro Val His
         165           170           175

Met Arg Ser Asp Ala Ser Lys Tyr Thr His Glu Lys Pro Glu Gly His
       180           185          190

Tyr Asn Trp His His Gly Ala Val Gln Tyr Ser Gly Gly Arg Phe Thr
    195            200           205

Ile Pro Thr Gly Ala Gly Lys Pro Gly Asp Ser Gly Arg Pro Ile Phe
       210           215          220

Asp Asn Lys Gly Arg Val Val Ala Ile Val Leu Gly Gly Ala Asn Glu
225              230            235           240

Gly Ser Arg Thr Ala Leu Ser Val Val Thr Trp Asn Lys Asp Met Val
         245           250          255

Thr Arg Val Thr Pro Glu Gly Ser Glu Glu Trp Ser Ala Pro Leu Ile
       260           265          270

Thr Ala Met Cys Val Leu Ala Asn Ala Thr Phe Pro Cys Phe Gln Pro
    275            280           285

Pro Cys Val Pro Cys Cys Tyr Glu Asn Asn Ala Glu Ala Thr Leu Arg
290              295            300

Met Leu Glu Asp Asn Val Asp Arg Pro Gly Tyr Tyr Asp Leu Leu Gln
305          310            315           320

Ala Ala Leu Thr Cys Arg Asn Gly Thr Arg His Arg Arg Ser Val Ser
         325           330          335

Gln His Phe Asn Val Tyr Lys Ala Thr Arg Pro Tyr Ile Ala Tyr Cys
       340           345          350

Ala Asp Cys Gly Ala Gly His Ser Cys His Ser Pro Val Ala Ile Glu
    355            360           365

Ala Val Arg Ser Glu Ala Thr Asp Gly Met Leu Lys Ile Gln Phe Ser
370              375            380

Ala Gln Ile Gly Ile Asp Lys Ser Asp Asn His Asp Tyr Thr Lys Ile
385          390            395           400

Arg Tyr Ala Asp Gly His Ala Ile Glu Asn Ala Val Arg Ser Ser Leu
         405           410          415

-continued

```
Lys Val Ala Thr Ser Gly Asp Cys Phe Val His Gly Thr Met Gly His
            420                 425                 430

Phe Ile Leu Ala Lys Cys Pro Gly Glu Phe Leu Gln Val Ser Ile
            435                 440                 445

Gln Asp Thr Arg Asn Ala Val Arg Ala Cys Arg Ile Gln Tyr His His
            450                 455                 460

Asp Pro Gln Pro Val Gly Arg Glu Lys Phe Thr Ile Arg Pro His Tyr
465                 470                 475                 480

Gly Lys Glu Ile Pro Cys Thr Thr Tyr Gln Gln Thr Thr Ala Lys Thr
                    485                 490                 495

Val Glu Glu Ile Asp Met His Met Pro Pro Asp Thr Pro Asp Arg Thr
                    500                 505                 510

Leu Leu Ser Gln Gln Ser Gly Asn Val Lys Ile Thr Val Gly Gly Lys
            515                 520                 525

Lys Val Lys Tyr Asn Cys Thr Cys Gly Thr Gly Asn Val Gly Thr Thr
            530                 535                 540

Asn Ser Asp Met Thr Ile Asn Thr Cys Leu Ile Glu Gln Cys His Val
545                 550                 555                 560

Ser Val Thr Asp His Lys Lys Trp Gln Phe Asn Ser Pro Phe Val Pro
                    565                 570                 575

Arg Ala Asp Glu Pro Ala Arg Lys Gly Lys Val His Ile Pro Phe Pro
                    580                 585                 590

Leu Asp Asn Ile Thr Cys Arg Val Pro Met Ala Arg Glu Pro Thr Val
            595                 600                 605

Ile His Gly Lys Arg Glu Val Thr Leu His Leu His Pro Asp His Pro
610                 615                 620

Thr Leu Phe Ser Tyr Arg Thr Leu Gly Glu Asp Pro Gln Tyr His Glu
625                 630                 635                 640

Glu Trp Val Thr Ala Ala Val Glu Arg Thr Ile Pro Val Pro Val Asp
                    645                 650                 655

Gly Met Glu Tyr His Trp Gly Asn Asn Asp Pro Val Arg Leu Trp Ser
                    660                 665                 670

Gln Leu Thr Thr Glu Gly Lys Pro His Gly Trp Pro His Gln Ile Val
            675                 680                 685

Gln Tyr Tyr Tyr Gly Leu Tyr Pro Ala Ala Thr Val Ser Ala Val Val
            690                 695                 700

Gly Met Ser Leu Leu Ala Leu Ile Ser Ile Phe Ala Ser Cys Tyr Met
705                 710                 715                 720

Leu Val Ala Ala Arg Ser Lys Cys Leu Thr Pro Tyr Ala Leu Thr Pro
                    725                 730                 735

Gly Ala Ala Val Pro Trp Thr Leu Gly Ile Leu Cys Cys Ala Pro Arg
                    740                 745                 750

Ala His Ala Ala Ser Val Ala Glu Thr Met Ala Tyr Leu Trp Asp Gln
            755                 760                 765

Asn Gln Ala Leu Phe Trp Leu Glu Phe Ala Ala Pro Val Ala Cys Ile
            770                 775                 780

Leu Ile Ile Thr Tyr Cys Leu Arg Asn Val Leu Cys Cys Cys Lys Ser
785                 790                 795                 800

Leu Ser Phe Leu Val Leu Leu Ser Leu Gly Ala Thr Ala Arg Ala Tyr
                    805                 810                 815

Glu His Ser Thr Val Met Pro Asn Val Val Gly Phe Pro Tyr Lys Ala
                    820                 825                 830
```

```
His Ile Glu Arg Pro Gly Tyr Ser Pro Leu Thr Leu Gln Met Gln Val
        835                 840                 845

Val Glu Thr Ser Leu Glu Pro Thr Leu Asn Leu Glu Tyr Ile Thr Cys
        850                 855                 860

Glu Tyr Lys Thr Val Val Pro Ser Pro Tyr Val Lys Cys Cys Gly Ala
865                 870                 875                 880

Ser Glu Cys Ser Thr Lys Glu Lys Pro Asp Tyr Gln Cys Lys Val Tyr
                    885                 890                 895

Thr Gly Val Tyr Pro Phe Met Trp Gly Gly Ala Tyr Cys Phe Cys Asp
                900                 905                 910

Ser Glu Asn Thr Gln Leu Ser Glu Ala Tyr Val Asp Arg Ser Asp Val
                915                 920                 925

Cys Arg His Asp His Ala Ser Ala Tyr Lys Ala His Thr Ala Ser Leu
        930                 935                 940

Lys Ala Lys Val Arg Val Met Tyr Gly Asn Val Asn Gln Thr Val Asp
945                 950                 955                 960

Val Tyr Val Asn Gly Asp His Ala Val Thr Ile Gly Thr Gln Phe
                    965                 970                 975

Ile Phe Gly Pro Leu Ser Ser Ala Trp Thr Pro Phe Asp Asn Lys Ile
                980                 985                 990

Val Val Tyr Lys Asp Glu Val Phe Asn Gln Asp Phe Pro Pro Tyr Gly
                995                 1000                1005

Ser Gly Gln Pro Gly Arg Phe Gly Asp Ile Gln Ser Arg Thr Val Glu
        1010                1015                1020

Ser Asn Asp Leu Tyr Ala Asn Thr Ala Leu Lys Leu Ala Arg Pro Ser
1025                1030                1035                1040

Pro Gly Met Val His Val Pro Tyr Thr Gln Thr Pro Ser Gly Phe Lys
                    1045                1050                1055

Tyr Trp Leu Lys Glu Lys Gly Thr Ala Leu Asn Thr Lys Ala Pro Phe
                1060                1065                1070

Gly Cys Gln Ile Lys Thr Asn Pro Val Arg Ala Met Asn Cys Ala Val
            1075                1080                1085

Gly Asn Ile Pro Val Ser Met Asn Leu Pro Asp Ser Ala Phe Thr Arg
        1090                1095                1100

Ile Val Glu Ala Pro Thr Ile Ile Asp Leu Thr Cys Thr Val Ala Thr
1105                1110                1115                1120

Cys Thr His Ser Ser Asp Phe Gly Gly Val Leu Thr Leu Thr Tyr Lys
                1125                1130                1135

Thr Asn Lys Asn Gly Asp Cys Ser Val His Ser His Ser Asn Val Ala
            1140                1145                1150

Thr Leu Gln Glu Ala Thr Ala Lys Val Lys Thr Ala Gly Lys Val Thr
        1155                1160                1165

Leu His Phe Ser Thr Ala Ser Ala Ser Pro Ser Phe Val Val Ser Leu
    1170                1175                1180

Cys Ser Ala Arg Ala Thr Cys Ser Ala Ser Cys Glu Pro Pro Lys Asp
1185                1190                1195                1200

His Ile Val Pro Tyr Ala Ala Ser His Ser Asn Val Val Phe Pro Asp
                1205                1210                1215

Met Ser Gly Thr Ala Leu Ser Trp Val Gln Lys Ile Ser Gly Gly Leu
        1220                1225                1230

Gly Ala Phe Ala Ile Gly Ala Ile Leu Val Leu Val Val Val Thr Cys
        1235                1240                1245

Ile Gly Leu Arg Arg
```

```
                                     1250

(2) INFORMATION FOR SEQ ID NO: 4:

(i) SEQUENCE CHARACTERISTICS:
         (A) LENGTH: 115 base pairs
         (B) TYPE: nucleic acid
         (C) STRANDEDNESS: single
         (D) TOPOLOGY: linear (ii) MOLECULE TYPE: RNA (genomic)

(iii) HYPOTHETICAL: NO (iv) ANTI-SENSE: NO (ix) FEATURE:
         (A) NAME/KEY: -
         (B) LOCATION: 1..115
         (D) OTHER INFORMATION: /label= 26S_region
             /note= "26S promoter and transcription start and
             proximal downstream region of pSFV1; Figure 8."

(ix) FEATURE:
         (A) NAME/KEY: misc_feature
         (B) LOCATION: 1..24
         (D) OTHER INFORMATION: /product= "26S promoter region"

(xi) SEQUENCE DESCRIPTION: SEQ ID NO: 4:

ACCTCTACGG CGGTCCTAGA TTGGTGCGTT AATACACAGA ATCTGATTGG ATCCCGGGTA        60

ATTAATTGAA TTACATCCCT ACGCAAACGT TTTACGGCCG CCGGTGGCGC CCGCG          115

(2) INFORMATION FOR SEQ ID NO: 5:

(i) SEQUENCE CHARACTERISTICS:
         (A) LENGTH: 127 base pairs
         (B) TYPE: nucleic acid
         (C) STRANDEDNESS: single
         (D) TOPOLOGY: linear (ii) MOLECULE TYPE: RNA (genomic)

(iii) HYPOTHETICAL: NO (iv) ANTI-SENSE: NO (ix) FEATURE:
         (A) NAME/KEY: -
         (B) LOCATION: 1..127
         (D) OTHER INFORMATION: /label= 26S_region
             /note= "26S promoter and transcription start and
             proximal downstream region of pSFV2; Figure 8."

(ix) FEATURE:
         (A) NAME/KEY: misc_feature
         (B) LOCATION: 1..24
         (D) OTHER INFORMATION: /product= "26S promoter region"

(xi) SEQUENCE DESCRIPTION: SEQ ID NO: 5:

ACCTCTACGG CGGTCCTAGA TTGGTGCGTT AATACACAGA ATTCTGATTA TAGCGCACTA        60

TTATATAGCA CCGGATCCCG GGTAATTAAT TGACGCAAAC GTTTTACGGC CGCCGGTGGC      120

GCCCGCG                                                                127

(2) INFORMATION FOR SEQ ID NO: 6:

(i) SEQUENCE CHARACTERISTICS:
         (A) LENGTH: 123 base pairs
         (B) TYPE: nucleic acid
         (C) STRANDEDNESS: single
         (D) TOPOLOGY: linear
```

```
      (ii) MOLECULE TYPE: RNA (genomic)

(iii) HYPOTHETICAL: NO (iv) ANTI-SENSE: NO (ix) FEATURE:
           (A) NAME/KEY: -
           (B) LOCATION: 1..123
           (D) OTHER INFORMATION: /label= 26S_region
                 /note= "26S promoter and transcription start and
                 proximal downstream region of pSFV3; Figure 8."

(ix) FEATURE:
           (A) NAME/KEY: misc_feature
           (B) LOCATION: 1..24
           (D) OTHER INFORMATION: /product= "26S promoter region"

(xi) SEQUENCE DESCRIPTION: SEQ ID NO: 6:

ACCTCTACGG CGGTCCTAGA TTGGTGCGTT AATACACAGA ATTCTGATTA TAGCGCACTA     60

TTATATAGCA CCATGGATCC CGGGTAATTA ATTGACGTTT TACGGCCGCC GGTGGCGCCC    120

GCG                                                                  123

(2) INFORMATION FOR SEQ ID NO: 7:

(i) SEQUENCE CHARACTERISTICS:
           (A) LENGTH: 54 base pairs
           (B) TYPE: nucleic acid
           (C) STRANDEDNESS: single
           (D) TOPOLOGY: linear (ii) MOLECULE TYPE: RNA (genomic)

(iii) HYPOTHETICAL: NO (vi) ORIGINAL SOURCE:
           (A) ORGANISM: Semliki Forest Virus (ix) FEATURE:
           (A) NAME/KEY: -
           (B) LOCATION: 1..54
           (D) OTHER INFORMATION: /label= restrict_site
                 /note= "sequence of SFV E2 genome in vicinity of Bam HI
                 site vector E2; Figure 12."

(ix) FEATURE:
           (A) NAME/KEY: CDS
           (B) LOCATION: 1..54

(xi) SEQUENCE DESCRIPTION: SEQ ID NO: 7:

AAC TCA CCT TTC GTC CCG AGA GCC GAC GAA CCG GCT AGA AAA GGC AAA      48
Asn Ser Pro Phe Val Pro Arg Ala Asp Glu Pro Ala Arg Lys Gly Lys
 1               5                  10                  15

GTC CAT                                                              54
Val His (2) INFORMATION FOR SEQ ID NO: 8:

(i) SEQUENCE CHARACTERISTICS:
           (A) LENGTH: 18 amino acids
           (B) TYPE: amino acid
           (D) TOPOLOGY: linear (ii) MOLECULE TYPE: protein (xi) SEQUENCE DESCRIPTION: SEQ ID NO: 8:

Asn Ser Pro Phe Val Pro Arg Ala Asp Glu Pro Ala Arg Lys Gly Lys
 1               5                  10                  15

Val His
```

(2) INFORMATION FOR SEQ ID NO: 9:

(i) SEQUENCE CHARACTERISTICS:
        (A) LENGTH: 46 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: HIV (ix) FEATURE:
        (A) NAME/KEY: -
        (B) LOCATION: 1..46
        (D) OTHER INFORMATION: /label= fragment
            /note= "HIV gp120 epitope introduced into SFV
            vector E2; Figure 12."

(ix) FEATURE:
        (A) NAME/KEY: CDS
        (B) LOCATION: 1..45

(xi) SEQUENCE DESCRIPTION: SEQ ID NO: 9:

```
GAT CCG CGT ATC CAG AGA GGA CCA GGA AGA GCA TTT GTT GAG CTA            45
Asp Pro Arg Ile Gln Arg Gly Pro Gly Arg Ala Phe Val Glu Leu
 1               5                  10                  15

G                                                                       46
```

(2) INFORMATION FOR SEQ ID NO: 10:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO: 10:

```
Asp Pro Arg Ile Gln Arg Gly Pro Gly Arg Ala Phe Val Glu Leu
 1               5                  10                  15
```

(2) INFORMATION FOR SEQ ID NO: 11:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (ix) FEATURE:
        (A) NAME/KEY: -
        (B) LOCATION: 1..51
        (D) OTHER INFORMATION: /label= chimaeric_seq
            /note= "SFV-HIV chimaeric sequence shown in Figure
            12."

(ix) FEATURE:
        (A) NAME/KEY: CDS
        (B) LOCATION: 1..51
        (D) OTHER INFORMATION: /product= "SFV-HIV chimaeric
            sequence"

(xi) SEQUENCE DESCRIPTION: SEQ ID NO: 11:

```
GAG GAT CCG CGT ATC CAG AGA GGA CCA GGA AGA GCA TTT GTT GAG GAT     48
Glu Asp Pro Arg Ile Gln Arg Gly Pro Gly Arg Ala Phe Val Glu Asp
 1               5                  10                  15

CCG                                                                 51
Pro
```

(2) INFORMATION FOR SEQ ID NO: 12:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO: 12:

```
Glu Asp Pro Arg Ile Gln Arg Gly Pro Gly Arg Ala Phe Val Glu Asp
 1               5                  10                  15
Pro
```

(2) INFORMATION FOR SEQ ID NO: 13:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: -
        (B) LOCATION: 1..60
        (D) OTHER INFORMATION: /label= oligonucleotide
            /note= "used to introduce new linker site"

(xi) SEQUENCE DESCRIPTION: SEQ ID NO: 13:

```
CGGCCAGTGA ATTCTGATTG GATCCCGGGT AATTAATTGA ATTACATCCC TACGCAAACG     60
```

(2) INFORMATION FOR SEQ ID NO: 14:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: -
        (B) LOCATION: 1..62
        (D) OTHER INFORMATION: /label= oligonucleotide
            /note= "used to introduce new linker site"

(xi) SEQUENCE DESCRIPTION: SEQ ID NO: 14:

```
GCGCACTATT ATAGCACCGG CTCCCGGGTA ATTAATTGAC GCAAACGTTT TACGGCCGCC     60
GG                                                                   62
```

(2) INFORMATION FOR SEQ ID NO: 15:

```
        (i) SEQUENCE CHARACTERISTICS:
            (A) LENGTH: 62 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: -
            (B) LOCATION: 1..62
            (D) OTHER INFORMATION: /label= oligonucleotide
                /note= "used to introduce new linker site"

(xi) SEQUENCE DESCRIPTION: SEQ ID NO: 15:

GCGCACTATT ATAGCACCAT GGATCCGGGT AATTAATTGA CGTTTTACGG CCGCCGGTGG      60

CG                                                                    62

(2) INFORMATION FOR SEQ ID NO: 16:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: -
            (B) LOCATION: 1..21
            (D) OTHER INFORMATION: /label= primer
                /note= "SP1 upstream sequencing primer"

(xi) SEQUENCE DESCRIPTION: SEQ ID NO: 16:

CGGCGGTCCT AGATTGGTGC G                                               21

(2) INFORMATION FOR SEQ ID NO: 17:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (ix) FEATURE:
            (A) NAME/KEY: -
            (B) LOCATION: 1..21
            (D) OTHER INFORMATION: /label= primer
                /note= "SP2 downstream sequencing primer"

(xi) SEQUENCE DESCRIPTION: SEQ ID NO: 17:

CGCGGGCGCC ACCGGCGGCC G                                               21

(2) INFORMATION FOR SEQ ID NO: 18:

(i) SEQUENCE CHARACTERISTICS:
```

```
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (ix) FEATURE:
            (A) NAME/KEY: -
            (B) LOCATION: 1..21
            (D) OTHER INFORMATION: /label= primer
                /note= "primer-1 for first strand cDNA synthesis"

(xi) SEQUENCE DESCRIPTION: SEQ ID NO: 18:

TTTCTCGTAG TTCTCCTCGT C                                              21

(2) INFORMATION FOR SEQ ID NO: 19:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (ix) FEATURE:
            (A) NAME/KEY: -
            (B) LOCATION: 1..27
            (D) OTHER INFORMATION: /label= primer
                /note= "primer-2 for first strand cDNA synthesis"

(xi) SEQUENCE DESCRIPTION: SEQ ID NO: 19:

GTTATCCCAG TGGTTGTTCT CGTAATA                                        27

(2) INFORMATION FOR SEQ ID NO: 20:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: -
            (B) LOCATION: 1..28
            (D) OTHER INFORMATION: /label= primer
                /note= "5' most primer for second strand cDNA
                synthesis, equals bp 1-28 of SFV sequence"

(xi) SEQUENCE DESCRIPTION: SEQ ID NO: 20:

ATGGCGGATG TGTGACATAC ACGACGCC                                       28

(2) INFORMATION FOR SEQ ID NO: 21:

(i) SEQUENCE CHARACTERISTICS:
            (A) LENGTH: 46 base pairs
            (B) TYPE: nucleic acid
            (C) STRANDEDNESS: double
```

(D) TOPOLOGY: linear (ii) MOLECULE TYPE: DNA (genomic)

(iii) HYPOTHETICAL: NO (ix) FEATURE:
         (A) NAME/KEY: -
         (B) LOCATION: 1..46
         (D) OTHER INFORMATION: /label= adaptor/note= "5'-sticky end
             (EcoRI-HindIII-NotI-XmaIII-SpeI) blunt end-3' adaptor"

(xi) SEQUENCE DESCRIPTION: SEQ ID NO: 21:

AATTCAAGCT TGCGGCCGCA CTAGTGTTCG AACGCCGGCG TGATCA                46

(2) INFORMATION FOR SEQ ID NO: 22:

(i) SEQUENCE CHARACTERISTICS:
         (A) LENGTH: 8 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (ix) FEATURE:
         (A) NAME/KEY: -
         (B) LOCATION: 1..8
         (D) OTHER INFORMATION: /label= oligonucleotide
             /note= "NcoI oligonucleotide"

(xi) SEQUENCE DESCRIPTION: SEQ ID NO: 22:

GCCATGGC                                                         8

(2) INFORMATION FOR SEQ ID NO: 23:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (ix) FEATURE:
         (A) NAME/KEY: -
         (B) LOCATION: 1..20
         (D) OTHER INFORMATION: /label= oligonucleotide
             /note= "oligonucleotide used for screening by
             colony hybridization"

(xi) SEQUENCE DESCRIPTION: SEQ ID NO: 23:

GGTGACACTA TAGCCATGGC                                            20

(2) INFORMATION FOR SEQ ID NO: 24:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (ix) FEATURE:
             (A) NAME/KEY: -
             (B) LOCATION: 1..24
             (D) OTHER INFORMATION: /label= oligonucleotide
                 /note= "site-directed mutagenic oligonucleotide
                 used to introduce a BamHI site into the SFV
                 genome"

(xi) SEQUENCE DESCRIPTION: SEQ ID NO: 24:

GATCGGCCTA GGAGCCGAGA GCCC                                              24

(2) INFORMATION FOR SEQ ID NO: 25:

(i) SEQUENCE CHARACTERISTICS:
             (A) LENGTH: 80 base pairs
             (B) TYPE: nucleic acid
             (C) STRANDEDNESS: single
             (D) TOPOLOGY: linear (ii) MOLECULE TYPE: RNA (genomic)

(iii) HYPOTHETICAL: NO (iv) ANTI-SENSE: NO (vi) ORIGINAL SOURCE:
             (A) ORGANISM: Semliki Forest Virus (ix) FEATURE:
             (A) NAME/KEY: -
             (B) LOCATION: 1..80
             (D) OTHER INFORMATION: /label= terminator
                 /note= "3' terminal sequence of cDNA expression
                 vector complementary to alphavirus genomic RNA"

(xi) SEQUENCE DESCRIPTION: SEQ ID NO: 25:

TTTCCAAAAA AAAAAAAAAA AAAAAAAAAA AAAAAAAAAA AAAAAAAAAA AAAAAAAAAA       60

AAAAAAAAAA AAAAACTAGT                                                   80

(2) INFORMATION FOR SEQ ID NO: 26:

(i) SEQUENCE CHARACTERISTICS:
             (A) LENGTH: 54 base pairs
             (B) TYPE: nucleic acid
             (C) STRANDEDNESS: single
             (D) TOPOLOGY: linear (ii) MOLECULE TYPE: RNA (genomic)

(iii) HYPOTHETICAL: NO (vi) ORIGINAL SOURCE:
             (A) ORGANISM: Semliki Forest Virus (ix) FEATURE:
             (A) NAME/KEY: -
             (B) LOCATION: 1..54
             (D) OTHER INFORMATION: /label= restrict_site
                 /note= "sequence of SFV vector E2 in vicinity of Bam HI
                 site; 12."

(ix) FEATURE:
             (A) NAME/KEY: mutation
             (B) LOCATION: 27..32
             (D) OTHER INFORMATION: /label= restriction_sit
                 /note= "BamHI recognition sequence introduced into
                 SFV E2 genome in SFV vector E2."

(ix) FEATURE:
             (A) NAME/KEY: CDS
             (B) LOCATION: 1..54

```
        (xi) SEQUENCE DESCRIPTION: SEQ ID NO: 26:

AAC TCA CCT TTC GTC CCG AGA GCC GAG GAT CCG GCT AGA AAA GGC AAA          48
Asn Ser Pro Phe Val Pro Arg Ala Glu Asp Pro Ala Arg Lys Gly Lys
  1               5                  10                  15

GTC CAT                                                                  54
Val His (2) INFORMATION FOR SEQ ID NO: 27:

(i) SEQUENCE CHARACTERISTICS:
         (A) LENGTH: 18 amino acids
         (B) TYPE: amino acid
         (D) TOPOLOGY: linear (ii) MOLECULE TYPE: protein (xi) SEQUENCE DESCRIPTION: SEQ ID NO: 27:

Asn Ser Pro Phe Val Pro Arg Ala Glu Asp Pro Ala Arg Lys Gly Lys
  1               5                  10                  15

Val His
```